United States Patent
Gilligan et al.

(10) Patent No.: US 6,365,589 B1
(45) Date of Patent: Apr. 2, 2002

(54) IMIDAZO-PYRIDINES, -PYRIDAZINES, AND -TRIAZINES AS CORTICOTROPIN RELEASING FACTOR ANTAGONISTS

(75) Inventors: Paul Joseph Gilligan; Richard Eric Olson, both of Wilmington, DE (US); William Eric Frietze, Kennett Square, PA (US)

(73) Assignee: Bristol-Myers Squibb Pharma Company, Princeton, NJ (US)

(*) Notice: Subject to any disclaimer, the term of this patent is extended or adjusted under 35 U.S.C. 154(b) by 0 days.

(21) Appl. No.: 09/344,257

(22) Filed: Jun. 25, 1999

Related U.S. Application Data

(60) Provisional application No. 60/091,515, filed on Jul. 2, 1998.

(51) Int. Cl.[7] .................... C07D 487/04; A61K 31/4188
(52) U.S. Cl. ......................................... 514/248; 544/236
(58) Field of Search ........................... 544/236; 514/248

(56) References Cited

U.S. PATENT DOCUMENTS

| | | | |
|---|---|---|---|
| 3,244,715 A * | 4/1966 | Castle | 260/250 |
| 4,797,399 A | 1/1989 | Ueda et al. | 514/253 |
| 5,015,473 A | 5/1991 | Chen | 514/192 |
| 5,075,311 A | 12/1991 | Hubsch et al. | 514/258 |
| 5,102,880 A | 4/1992 | Chakravarty et al. | 514/212 |
| 5,128,327 A | 7/1992 | Chakravarty et al. | 514/81 |
| 5,145,959 A | 9/1992 | Hubsch et al. | 544/279 |
| 5,157,026 A | 10/1992 | Chakravarty et al. | 514/81 |
| 5,171,353 A | 12/1992 | Fischer et al. | 71/92 |
| 5,176,991 A | 1/1993 | Jones et al. | 430/569 |
| 5,178,997 A | 1/1993 | Maskasky | 430/569 |
| 5,183,732 A | 2/1993 | Maskasky | 430/569 |
| 5,185,239 A | 2/1993 | Maskasky | 430/569 |
| 5,187,159 A | 2/1993 | Greenlee et al. | 514/81 |
| 5,250,408 A | 10/1993 | Chang et al. | 430/569 |
| 5,250,531 A | 10/1993 | Cooper | 514/256 |
| 5,260,322 A | 11/1993 | Nakasima et al. | 514/341 |
| 5,272,052 A | 12/1993 | Maskasky | 430/569 |
| 5,312,820 A | 5/1994 | Ashton et al. | 514/227.5 |
| 5,319,080 A | 6/1994 | Leumann | 536/27.1 |
| 5,330,989 A | 7/1994 | Soll et al. | 514/258 |
| 5,332,814 A | 7/1994 | Moser | 544/229 |
| 5,332,820 A | 7/1994 | Duncia | 546/118 |
| 5,338,740 A | 8/1994 | Carpino et al. | 514/259 |
| 5,338,756 A | 8/1994 | Fortin et al. | 514/394 |
| 5,374,638 A | 12/1994 | Dhanoa et al. | 514/326 |
| 5,376,665 A | 12/1994 | Miyata et al. | 514/301 |
| 5,376,666 A | 12/1994 | Duncia | 514/303 |
| 5,385,925 A | 1/1995 | Narr et al. | 514/382 |
| 5,389,509 A | 2/1995 | Maskasky | 430/567 |
| 5,389,634 A | 2/1995 | Fortin et al. | 514/248 |
| 5,389,641 A | 2/1995 | Naka et al. | 514/303 |
| 5,393,878 A | 2/1995 | Leumann | 536/28.2 |
| 5,395,840 A | 3/1995 | Miiler et al. | 514/300 |
| 5,424,432 A | 6/1995 | Fredenburgh et al. | 546/118 |
| 5,428,168 A | 6/1995 | Whittaker et al. | 546/118 |
| 5,434,150 A | 7/1995 | Austel et al. | 514/228.5 |
| 5,444,068 A | 8/1995 | Heitsch et al. | 514/303 |
| 5,446,159 A | 8/1995 | Stucky et al. | 546/119 |
| 5,446,160 A | 8/1995 | Stucky et al. | 546/118 |
| 5,459,147 A | 10/1995 | Hauel et al. | 514/303 |
| 5,470,867 A | 11/1995 | Fortin et al. | 514/393 |
| 5,498,715 A | 3/1996 | Kuo et al. | 546/118 |
| 5,514,682 A | 5/1996 | Street | 514/266 |
| 5,541,324 A | 7/1996 | TenBrink et al. | 544/346 |
| 5,565,437 A | 10/1996 | Marquez et al. | 514/45 |
| 5,580,981 A | 12/1996 | Carpino | 544/262 |
| 5,587,393 A | 12/1996 | Narr et al. | 514/381 |
| 5,587,470 A | 12/1996 | Cook et al. | 536/28.1 |
| 5,597,826 A | 1/1997 | Howard et al. | 514/255 |
| 5,635,525 A | 6/1997 | Heitsch et al. | 514/394 |
| 5,656,649 A | 8/1997 | Lunkenheimer et al. | 514/394 |
| 5,684,029 A | 11/1997 | Narr et al. | 514/394 |

FOREIGN PATENT DOCUMENTS

| | | |
|---|---|---|
| DE | 3921271 A | 1/1991 |
| DE | 4208535 A | 9/1992 |
| DE | 4230464 A1 | 9/1992 |
| EP | 0251760 | 6/1987 |
| EP | 0345747 A2 | 12/1989 |
| EP | 0399731 B1 | 11/1990 |
| EP | 0400974 A2 | 12/1990 |
| EP | 0416740 A2 | 3/1991 |
| EP | 0434038 A1 | 6/1991 |
| EP | 0445467 A1 | 9/1991 |

(List continued on next page.)

OTHER PUBLICATIONS

Mataka et al, *Reduction of 4,7–Diphenyl–1,2,5–thia (oxa) diazolo [3,4–c]pyridines Affording 2,5–Diphenyl–3,4–diaminopyridines and Ring Closure of the Diamines to Fluorescent Azaheterocycles*, Jrnl of Heterocyclic Chem., 19/6, 1481–1488, (1982).

Kiyama et al., *Synthesis and Evaluation of Novel Nonpeptide Angiotensin II Receptor Antagonists . . .* , Chem. Pharm Bull., 43/3, 450–460, (1995).

*Primary Examiner*—Bruck Kifle
*Assistant Examiner*—Deepak R. Rao
(74) *Attorney, Agent, or Firm*—Monte R. Browder; Kenneth B. Rubin; Kalim S. Fuzail

(57) ABSTRACT

The present invention describes novel imidazo-pyridines, -pyridazines, and -triazines of formula I:

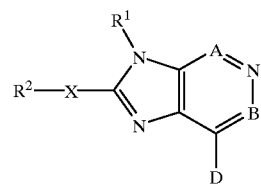

wherein A and B can be C or N and D is aryl or heteroaryl or pharmaceutically acceptable salt forms thereof, which are useful as CRF antagonists.

4 Claims, No Drawings

FOREIGN PATENT DOCUMENTS

| | | |
|---|---|---|
| EP | 0480204 A1 | 4/1992 |
| EP | 0533189 A1 | 9/1992 |
| EP | 0520423 A2 | 12/1992 |
| EP | 0353902 B1 | 5/1993 |
| EP | 0542681 A1 | 5/1993 |
| EP | 0574174 A2 | 12/1993 |
| EP | 0577558 A2 | 1/1994 |
| EP | 0616807 A1 | 3/1994 |
| EP | 0584817 B1 | 4/1996 |
| EP | 0706795 A2 | 4/1996 |
| EP | 0718674 A1 | 6/1996 |
| EP | 0584811 B1 | 10/1996 |
| EP | 0773023 A1 | 5/1997 |
| EP | 0812831 A1 | 12/1997 |
| EP | 0839813 A1 | 5/1998 |
| GB | 2263637 A | 8/1993 |
| GB | 2272899 A | 6/1994 |
| WO | WO93/03033 | 2/1993 |
| WO | WO93/23396 | 11/1993 |
| WO | WO94/10171 | 5/1994 |
| WO | WO94/12461 | 6/1994 |
| WO | WO94/18215 | 8/1994 |
| WO | WO94/22859 | 10/1994 |
| WO | WO95/10506 | 4/1995 |
| WO | WO95/20597 | 8/1995 |
| WO | WO95/21836 | 8/1995 |
| WO | WO95/21838 | 8/1995 |
| WO | WO95/33727 | 12/1995 |
| WO | WO95/33750 | 12/1995 |
| WO | WO95/34563 | 12/1995 |
| WO | WO95/34564 | 12/1995 |
| WO | WO96/01624 | 1/1996 |
| WO | WO96/02535 A1 | 2/1996 |
| WO | WO96/17076 | 6/1996 |
| WO | WO96/17077 | 6/1996 |
| WO | WO96/19478 | 6/1996 |
| WO | WO96/24338 | 8/1996 |
| WO | WO96/24375 | 8/1996 |
| WO | WO97/08150 | 3/1997 |
| WO | WO97/37993 | 10/1997 |
| WO | WO98/08847 | 3/1998 |
| WO | WO98/35967 | 8/1998 |

\* cited by examiner

IMIDAZO-PYRIDINES, -PYRIDAZINES, AND -TRIAZINES AS CORTICOTROPIN RELEASING FACTOR ANTAGONISTS

This application claims the benefit of Provisional Application No. 60/091,515, filed on Jul. 2, 1998.

FIELD OF THE INVENTION

This invention relates to novel imidazo-pyridines, pyridazines, and -triazines, pharmaceutical compositions containing the same and methods of using same in the treatment of psychiatric disorders and neurological diseases including affective disorder, anxiety, depression, headache, irritable bowel syndrome, post-traumatic stress disorder, supranuclear palsy, immune suppression, Alzheimer's disease, gastrointestinal diseases, anorexia nervosa or other feeding disorder, drug addiction, drug or alcohol withdrawal symptoms, inflammatory diseases, cardiovascular or heart-related diseases, fertility problems, human immunodeficiency virus infections, hemorrhagic stress, obesity, infertility, head and spinal cord traumas, epilepsy, stroke, ulcers, amyotrophic lateral sclerosis, hypoglycemia or a disorder the treatment of which can be effected or facilitated by antagonizing corticotropin releasing factor (CRF), including but not limited to disorders induced or facilitated by CRF.

BACKGROUND OF THE INVENTION

Corticotropin releasing factor, a 41 amino acid peptide, is the primary physiological regulator of proopiomelanocortin (POMC)-derived peptide secretion from the anterior pituitary gland [J. Rivier et al., Proc. Nat. Acad. Sci. (USA) 80:4851 (1983); W. Vale et al., Science 213:1394 (1981)]. In addition to its endocrine role at the pituitary gland, immunohistochemical localization of CRF has demonstrated that the hormone has a broad extrahypothalamic distribution in the central nervous system and produces a wide spectrum of autonomic, electrophysiological and behavioral effects consistent with a neurotransmitter or neuromodulator role in brain [W. Vale et al., Rec. Prog. Horm. Res. 39:245 (1983); G. F. Koob, Persp. Behav. Med. 2:39 (1985); E. B. De Souza et al., J. Neurosci. 5:3189 (1985)]. There is also evidence that CRF plays a significant role in integrating the response of the immune system to physiological, psychological, and immunological stressors [J. E. Blalock, Physiological Reviews 69:1 (1989); J. E. Morley, Life Sci. 41:527 (1987)].

Clinical data provides evidence that CRF has a role in psychiatric disorders and neurological diseases including depression, anxiety-related disorders and feeding disorders. A role for CRF has also been postulated in the etiology and pathophysiology of Alzheimer's disease, Parkinson's disease, Huntington's disease, progressive supranuclear palsy and amyotrophic lateral sclerosis as they relate to the dysfunction of CRF neurons in the central nervous system [for review see E. B. De Souza, Hosp. Practice 23:59 (1988)].

In affective disorder, or major depression, the concentration of CRF is significantly increased in the cerebral spinal fluid (CSF) of drug-free individuals [C. B. Nemeroff et al., Science 226:1342 (1984); C. M. Banki et al., Am. J. Psychiatry 144:873 (1987); R. D. France et al., Biol. Psychiatry 28:86 (1988); M. Arato et al., Biol Psychiatry 25:355 (1989)]. Furthermore, the density of CRF receptors is significantly decreased in the frontal cortex of suicide victims, consistent with a hypersecretion of CRF [C. B. Nemeroff et al., Arch. Gen. Psychiatry 45:577 (1988)]. In addition, there is a blunted adrenocorticotropin (ACTH) response to CRF (i.v. administered) observed in depressed patients [P. W. Gold et al., Am J. Psychiatry 141:619 (1984); F. Holsboer et al., Psychoneuroendocrinology 9:147 (1984); P. W. Gold et al., New Eng. J. Med. 314:1129 (1986)]. Preclinical studies in rats and non-human primates provide additional support for the hypothesis that hypersecretion of CRF may be involved in the symptoms seen in human depression [R. M. Sapolsky, Arch. Gen. Psychiatry 46:1047 (1989)]. There is preliminary evidence that tricyclic antidepressants can alter CRF levels and thus modulate the numbers of CRF receptors in brain [Grigoriadis et al., Neuropsychopharmacology 2:53 (1989)].

There has also been a role postulated for CRF in the etiology of anxiety-related disorders. CRF produces anxiogenic effects in animals and interactions between benzodiazepine/non-benzodiazepine anxiolytics and CRF have been demonstrated in a variety of behavioral anxiety models [D. R. Britton et al., Life Sci. 31:363 (1982); C. W. Berridge and A. J. Dunn Regul. Peptides 16:83 (1986)]. Preliminary studies using the putative CRF receptor antagonist α-helical ovine CRF (9–41) in a variety of behavioral paradigms demonstrate that the antagonist produces "anxiolytic-like" effects that are qualitatively similar to the benzodiazepines [C. W. Berridge and A. J. Dunn, Horm. Behav. 21:393 (1987), Brain Research Reviews 15:71 (1990)]. Neurochemical, endocrine and receptor binding studies have all demonstrated interactions between CRF and benzodiazepine anxiolytics providing further evidence for the involvement of CRF in these disorders. Chlordiazepoxide attenuates the "anxiogenic" effects of CRF in both the conflict test [K. T. Britton et al., Psychopharmacology 86:170 (1995); K. T. Britton et al., Psychopharmacology 94:306 (1988)] and in the acoustic startle test [N. R. Swerdlow et al., Psychopharmacology 88:147 (1986)] in rats. The benzodiazepine receptor antagonist (Ro15–1788), which was without behavioral activity alone in the operant conflict test, reversed the effects of CRF in a dose-dependent manner while the benzodiazepine inverse agonist (FG7142) enhanced the actions of CRF [K. T. Britton et al., Psychopharmacology 94:306 (1988)].

The mechanisms and sites of action through which the standard anxiolytics and antidepressants produce their therapeutic effects remain to be elucidated. It has been hypothesized however, that they are involved in the suppression of the CRF hypersecretion that is observed in these disorders. Of particular interest is that preliminary studies examining the effects of a CRF receptor antagonist (α-helical $CRF_{9-41}$) in a variety of behavioral paradigms have demonstrated that the CRF antagonist produces "anxiolytic-like" effects qualitatively similar to the benzodiazepines [for review see G. F. Koob and K. T. Britton, In: Corticotropin-Releasing Factor: Basic and Clinical Studies of a Neuropeptide, E. B. De Souza and C. B. Nemeroff eds., CRC Press p221 (1990)].

In view of the above, efficacious and specific antagonists of CRF are desired as potentially valuable therapeutic agents for the treatment of psychiatric disorders and neurological diseases. It is thus desirable to discover new CRF antagonists.

SUMMARY OF THE INVENTION

Accordingly, one object of the present invention is to provide novel imidazo-pyridines, -pyridazines, and triazines, which are useful as CRF antagonists or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt form thereof.

It is another object of the present invention to provide a method for treating psychiatric disorders and neurological diseases comprising administering to a host in need of such treatment a therapeutically effective amount of at least one of the compounds of the present invention or a pharmaceutically acceptable salt form thereof.

These and other objects, which will become apparent during the following detailed description, have been achieved by the inventors' discovery that compounds of formula I:

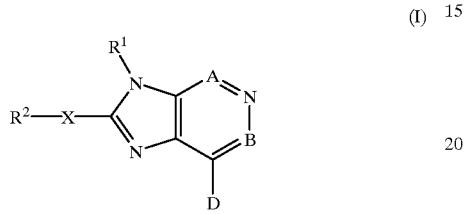

or pharmaceutically acceptable salt forms thereof, wherein $R^1$, $R^2$, $R^3$, and $R^4$ are defined below, are CRF antagonists.

DETAILED DESCRIPTION OF THE INVENTION

[1] Thus, in a first embodiment, the present invention provides a novel compound of formula I:

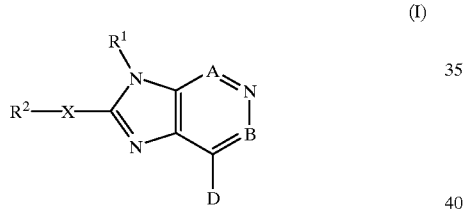

or a stereoisomer or pharmaceutically acceptable salt form thereof, wherein:

A is N or C—$R^7$;

B is N or C—$R^8$;

D is an aryl or heteroaryl group attached through an unsaturated carbon atom;

X is selected from the group CH—$R^9$, N—$R^{10}$, O, $S(O)_n$ and a bond;

n is 0, 1 or 2;

$R^1$ is selected from the group $C_{1-10}$ alkyl, $C_{2-10}$ alkenyl, $C_{2-10}$ alkynyl, $C_{3-8}$ cycloalkyl, $C_{3-6}$ cycloalkyl-$C_{1-6}$ alkyl, $C_{1-4}$ alkoxy-$C_{1-4}$ alkyl, —$SO_2$-$C_{1-10}$ alkyl, —$SO_2$—$R^{1a}$, and —$SO_2$—$R^{1b}$;

$R^1$ is substituted with 0–1 substituents selected from the group —CN, $^{13}$ $^{S(O)}{}_n R^{14b}$, —$COR^{13a}$, —$CO_2R^{13a}$, —$NR^{15a}COR^{13a}$, —$N(COR^{13a})_2$, —$NR^{15a}CONR_{13a}R^{16a}$, —$NR^{15a}CO_2R^{14b}$, —$CONR^{13a}R^{16a}$, 1-morpholinyl, 1-piperidinyl, 1-piperazinyl, and $C_{3-8}$ cycloalkyl, wherein 0–1 carbon atoms in the $C_{4-8}$ cycloalkyl is replaced by a group selected from the group —O—, —$S(O)_n$—, —$NR^{13a}$—, —$NCO_2R^{14b}$—, —$NCOR^{14b}$— and —$NSO_2R^{14b}$—, and wherein $N_4$ in 1-piperazinyl is substituted with 0–1 substituents selected from the group $R^{13a}$, $CO_2R^{14b}$, $COR^{14b}$ and $SO_2R^{14b}$;

$R^1$ is also substituted with 0–3 substituents independently selected at each occurrence from the group $R^{1a}$, $R^{1b}$, $R^{1c}$, $C_{1-6}$ alkyl, $C_{2-8}$ alkenyl, $C_{2-8}$ alkynyl, Br, Cl, F, I, $C_{1-4}$ haloalkyl, —$OR^{13a}$, —$NR^{13a}R^{16a}$, $C_{1-4}$ alkoxy-$C_{1-4}$ alkyl, and $C_{3-8}$ cycloalkyl which is substituted with 0–1 $R^9$ and in which 0–1 carbons of $C_{4-8}$ cycloalkyl is replaced by —O—;

provided that $R^1$ is other than a cyclohexyl-$(CH_2)_2$- group;

$R^{1a}$ is aryl and is selected from the group phenyl, naphthyl, indanyl and indenyl, each $R^{1a}$ being substituted with 0–1 —$OR^{17}$ and 0–5 substituents independently selected at each occurrence from the group $C_{1-6}$ alkyl, $C_{3-6}$ cycloalkyl, Br, Cl, F, I, $C_{1-4}$ haloalkyl, —CN, nitro, SH, —$S(O)_n R^{18}$, —$COR^{17}$, —$OC(O)R^{18}$, —$NR^{15a}COR^{17}$, —$N(COR^{17})_2$, —$NR^{15a}CONR^{17a}R^{19a}$, —$NR^{15a}CO_2R^{18}$, —$NR^{17a}R^{19a}$, and —$CONR^{17a}R^{19a}$;

$R^{1b}$ is heteroaryl and is selected from the group pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, pyrazolyl, triazolyl, tetrazolyl, indazolyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, benzoxazolin-2-onyl, benzodioxolanyl and benzodioxane, each heteroaryl being substituted on 0–4 carbon atoms with a substituent independently selected at each occurrence from the group $C_{1-6}$ alkyl, $C_{3-6}$ cycloalkyl, Br, Cl, F, I, $C_{1-4}$ haloalkyl, —CN, nitro, —$OR^{17}$, SH, —$S(O)_m R^{18}$, —$COR^{17}$, —$OC(O)R^{18}$, —$NR^{15a}COR^{17}$, —$N(COR^{17})_2$, —$NR^{15a}CONR^{17a}R^{19a}$, —$NR^{15a}CO_2R^{18}$, —$NR^{17a}R^{19a}$, and —$CONR^{17a}R^{19a}$ and each heteroaryl being substituted on any nitrogen atom with 0–1 substituents selected from the group $R^{15a}$, $CO_2R^{14b}$, $COR^{14b}$ and $SO_2R^{14b}$;

$R^{1c}$ is heterocyclyl and is a saturated or partially saturated heteroaryl, each heterocyclyl being substituted on 0–4 carbon atoms with a substituent independently selected at each occurrence from the group $C_{1-6}$ alkyl, $C_{3-6}$ cycloalkyl, Br, Cl, F, I, $C_{1-4}$ haloalkyl, —CN, nitro, —$OR^{13a}$, SH, —$S(O)_n R^{14b}$, —$COR^{13a}$, —$OC(O)R^{14b}$, —$NR^{15a}COR^{13a}$, —$N(COR^{13a})_2$, —$NR^{15a}CONR^{13a}R^{16a}$, —$NR^{15a}CO_2R^{14b}$, —$NR^{13a}R^{16a}$, and —$CONR^{13a}R^{16a}$ and each heterocyclyl being substituted on any nitrogen atom with 0–1 substituents selected from the group $R^{13a}$, $CO_2R^{14b}$, $COR^{14b}$ and $SO_2R^{14b}$ and wherein any sulfur atom is optionally monooxidized or dioxidized;

provided that $R^1$ is other than a —$(CH_2)_{1-4}$-aryl, —$(CH_2)_{1-4}$-heteroaryl, or —$(CH_2)_{1-4}$-heterocycle, wherein the aryl, heteroaryl, or heterocycle group is substituted or unsubstituted;

$R^2$ is selected from the group $C_{1-4}$ alkyl, $C_{3-8}$ cycloalkyl, $C_{2-4}$ alkenyl, and $C_{2-4}$ alkynyl and is substituted with 0–3 substituents selected from the group —CN, hydroxy, halo and $C_{1-4}$ alkoxy;

alternatively $R^2$, in the case where X is a bond, is selected from the group —CN, $CF_3$ and $C_2F_5$;

$R^7$ and $R^8$ are independently selected at each occurrence from the group H, Br, Cl, F, I, —CN, $C_{1-4}$ alkyl, $C_{3-8}$ cycloalkyl, $C_{1-4}$ alkoxy, $C_{1-4}$ alkylthio, $C_{1-4}$ alkylsulfinyl, $C_{1-4}$ alkylsulfonyl, amino, $C_{1-4}$ alkylamino, $(C_{1-4}$ alkyl)$_2$amino and phenyl, each phenyl is substituted with 0–3 groups selected from the group $C_{1-7}$ alkyl, $C_{3-8}$ cycloalkyl, Br, Cl, F, I, $C_{1-4}$ haloalkyl, nitro, $C_{1-4}$ alkoxy, $C_{1-4}$ haloalkoxy, $C_{1-4}$ alkylthio, $C_{1-4}$ alkyl sulfinyl, $C_{1-4}$ alkylsulfonyl, $C_{1-6}$ alkylamino and $(C_{1-4}$ alkyl)$_2$amino;

$R^9$ and $R^{10}$ are independently selected at each occurrence from the group H, $C_{1-4}$ alkyl, $C_{3-6}$ cycloalkyl-$C_{1-4}$ alkyl and $C_{3-8}$ cycloalkyl;

$R^{13}$ is selected from the group H, $C_{1-4}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl, aryl, aryl($C_{1-4}$ alkyl)-, heteroaryl and heteroaryl ($C_{1-4}$ alkyl)-;

$R^{13a}$ and $R^{16a}$ are independently selected at each occurrence from the group H, $C_{1-4}$ alkyl, $C_{1-4}$ haloalkyl, $C_{1-4}$ alkoxy-$C_{1-4}$ alkyl, $C_{3-6}$ cycloalkyl, and $C_{3-6}$ cycloalkyl-$C_{1-6}$ alkyl;

$R^{14}$ is selected from the group $C_{1-4}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl, aryl, aryl($C_{1-4}$ alkyl)-, heteroaryl and heteroaryl($C_{1-4}$ alkyl)- and benzyl, each benzyl being substituted on the aryl moiety with 0–1 substituents selected from the group $C_{1-4}$ alkyl, Br, Cl, F, I, $C_{1-4}$ haloalkyl, nitro, $C_{1-4}$ alkoxy $C_{1-4}$ haloalkoxy, and dimethylamino;

$R^{14a}$ is selected from the group $C_{1-4}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl and benzyl, each benzyl being substituted on the aryl moiety with 0–1 substituents selected from the group $C_{1-4}$ alkyl, Br, Cl, F, I, $C_{1-4}$ haloalkyl, nitro, $C_{1-4}$ alkoxy, $C_{1-4}$ haloalkoxy, and dimethylamino;

$R^{14b}$ is selected from the group $C_{1-4}$ alkyl, $C_{1-4}$ haloalkyl, $C_{1-4}$ alkoxy-$C_{1-4}$ alkyl, $C_{3-6}$ cycloalkyl, and $C_{3-6}$ cycloalkyl-$C_{1-6}$ alkyl;

$R^{15}$ is independently selected at each occurrence from the group H, $C_{1-4}$ alkyl, $C_{3-7}$ cycloalkyl, $C_{3-6}$ cycloalkyl-$C_{1-6}$ alkyl, phenyl and benzyl, each phenyl or benzyl being substituted on the aryl moiety with 0–3 groups chosen from the group $C_{1-4}$ alkyl, Br, Cl, F, I, $C_{1-4}$ haloalkyl, nitro, $C_{1-4}$ alkoxy, $C_{1-4}$ haloalkoxy, and dimethylamino;

$R^{15a}$ is independently selected at each occurrence from the group H, $C_{1-4}$ alkyl, $C_{3-7}$ cycloalkyl, and $C_{3-6}$ cycloalkyl-$C_{1-6}$ alkyl;

$R^{17}$ is selected at each occurrence from the group H, $C_{1-6}$ alkyl, $C_{3-10}$ cycloalkyl, $C_{3-6}$ cycloalkyl-$C_{1-6}$ alkyl, $C_{1-2}$ alkoxy-$C_{1-2}$ alkyl, $C_{1-4}$ haloalkyl, $R^{14}S(O)_n$-$C_{1-4}$ alkyl, and $R^{17b}R^{19b}N$-$C_{2-4}$ alkyl;

$R^{18}$ and $R^{19}$ are independently selected at each occurrence from the group H, $C_{1-6}$ alkyl, $C_{3-10}$ cycloalkyl, $C_{3-6}$ cycloalkyl-$C_{1-6}$ alkyl, $C_{1-2}$ alkoxy-$C_{1-2}$ alkyl, and $C_{1-4}$ haloalkyl;

alternatively, in an $NR^{17}R^{19}$ moiety, $R^{17}$ and $R^{19}$ taken together form 1-pyrrolidinyl, 1-morpholinyl, 1-piperidinyl or 1-piperazinyl, wherein $N_4$ in 1-piperazinyl is substituted with 0–1 substituents selected from the group $R^{13}$, $CO_2R^{14}$, $OCR^{14}$ and $SO_2R^{14}$;

alternatively, in an $NR^{17b}R^{19b}$ moiety, $R^{17b}$ and $R^{19b}$ taken together form 1-pyrrolidinyl, 1-morpholinyl, 1-piperidinyl or 1-piperazinyl, wherein $N_4$ in 1-piperazinyl is substituted with 0–1 substituents selected from the group $R^{13}$, $CO_2R^{14}$, $COR^{14}$ and $SO_2R^{14}$;

$R^{17a}$ and $R^{19a}$ are independently selected at each occurrence from the group H, $C_{1-6}$ alkyl, $C_{3-10}$ cycloalkyl, $C_{3-6}$ cycloalkyl-$C_{1-6}$ alkyl and $C_{1-4}$ haloalkyl;

aryl is independently selected at each occurrence from the group phenyl, naphthyl, indanyl and indenyl, each aryl being substituted with 0–5 substituents independently selected at each occurrence from the group $C_{1-6}$ alkyl, $C_{3-6}$ cycloalkyl, methylenedioxy, $C_{1-4}$ alkoxy-$C_{1-4}$ alkoxy, —$OR^{17}$, Br, Cl, F, I, $C_{1-4}$ haloalkyl, —CN, —$NO_2$, SH, —$S(O)_nR^{18}$, —$COR^{17}$, —$CO_2R^{17}$, —$OC(O)R^{18}$, —$NR^{15}COR^{17}$, —$N(COR^{17})_2$, —$NR^{15}CONR^{17}R^{19}$, —$NR^{15}CO_2R^{18}$, —$NR^{17}R^{19}$, and —$CONR^{17}R^{19}$ and up to 1 phenyl, each phenyl substituent being substituted with 0–4 substituents selected from the group $C_{1-3}$ alkyl, $C_{1-3}$ alkoxy, Br, Cl, F, I, —CN, dimethylamino, $CF_3$, $C_2F_5$, $OCF_3$, $SO_2Me$ and acetyl;

heteroaryl is independently selected at each occurence from the group pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, triazolyl, tetrazolyl, indazolyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, benzoxazolin-2-on-yl, benzodioxolanyl and benzodioxane, each heteroaryl being substituted 0–4 carbon atoms with a substituent independently selected at each occurrence from the group $C_{1-6}$ alkyl, $C_{3-6}$ cycloalkyl, Br, Cl, F, I, $C_{1-4}$ haloalkyl, —CN, nitro, —$OR^{17}$, SH, —$S(O)_mR^{18}$, —$COR^{17}$, —$CO_2R^{17}$, —$OC(O)R^{18}$, —$NR^{15}COR^{17}$, —$N(COR^{17})_2$, —$NR^{15}CONR^{17}R^{19}$, —$NR^{15}CO_2R^{18}$, —$NR^{17}R^{19}$, and —$CONR^{17}R^{19}$ and each heteroaryl being substituted on any nitrogen atom with 0–1 substituents selected from the group $R^{15}$, $CO_2R^{14a}$, $COR^{14a}$ and $SO_2R^{14a}$; and, provided that when D is imidazole or triazole, $R^1$ is other than unsubstituted $C_{1-6}$ linear or branched alkyl or $C_{3-6}$ cycloalkyl.

[2] In a preferred embodiment, the present invention provides a novel compound of formula Ia:

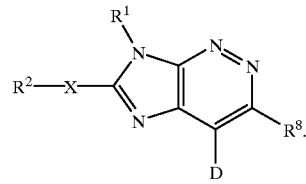

(Ia)

[3] In another preferred embodiment, the present invention provides a novel compound of formula Ib:

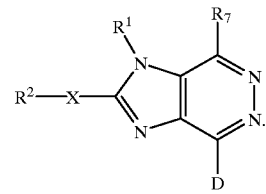

(Ib)

[4] In another preferred embodiment, the present invention provides a novel compound of formula Ic:

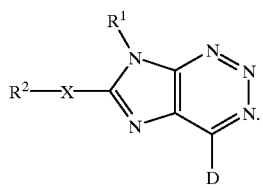

(Ic)

[5] In another preferred embodiment, the present invention provides a novel compound of formula Id:

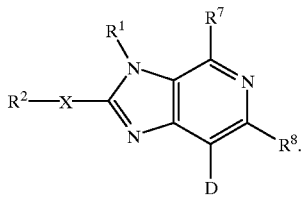

(Id)

[5a] In a more preferred embodiment, the present invention provides a novel compound of formula Id, wherein:
x is selected from the group O, S(O)$_n$ and a bond;
n is 0, 1 or 2;
$R^1$ is selected from the group $C_{1-6}$ alkyl, $C_{2-6}$ alkenyl, $C_{2-6}$ alkynyl, and $C_{3-8}$ cycloalkyl;
$R^1$ is substituted with 0–1 substituents selected from the group —CN, —S(O)$_n R^{14b}$, —COR$^{13a}$, —CO$_2 R^{13a}$, and $C_{3-8}$ cycloalkyl, wherein 0–1 carbon atoms in the $C_{4-8}$ cycloalkyl is replaced by a group selected from the group —O—, —S(O))$_n$—, —NR$^{13a}$—, —NCO$_2 R^{14b}$—, —NCOR$^{14b}$— and —NSO$_2 R^{14b}$-;
$R^1$ is also substituted with 0–2 substituents independently selected at each occurrence from the group $R^{1a}$, $R^{1b}$, $C_{1-6}$ alkyl, $C_{2-8}$ alkenyl, $C_{2-8}$ alkynyl, Br, Cl, F, CF$_3$, CF$_2$CF$_3$, —OR$^{13a}$, —NR$^{13a}R^{16a}$, $C_{1-2}$ alkoxy-$C_{1-2}$ alkyl, and $C_{3-8}$ cycloalkyl which is substituted with 0–1 $R^9$ and in which 0–1 carbons of $C_{4-8}$ cycloalkyl is replaced by —O—;
provided that $R^1$ is other than a cyclohexyl-(CH$_2$)$_2$-group;
$R^{1a}$ is aryl and is selected from the group phenyl and indanyl, each $R^{1a}$ being substituted with 0–1 —OR$^{17}$ and 0–5 substituents independently selected at each occurrence from the group $C_{114}$ alkyl, $C_{3-6}$ cycloalkyl, Br, Cl, F, $C_{1-4}$ haloalkyl, —CN, —S(O)$_n R^{18}$, —COR$^{17}$, —NR$^{17a}R^{19a}$, and —CONR$^{17a}R^{19a}$;
$R^{1b}$ is heteroaryl and is selected from the group pyridyl, pyrimidinyl, furanyl, thienyl, imidazolyl, thiazolyl, pyrrolyl, oxazolyl, isoxazolyl, pyrazolyl, triazolyl, tetrazolyl, and indazolyl, each heteroaryl being substituted on 0–4 carbon atoms with a substituent independently selected at each occurrence from the group $C_{1-4}$ alkyl, $C_{3-6}$ cycloalkyl, Br, Cl, F, CF$_3$, —CN, —OR$^{17}$, —S(O)$_m R^{18}$, —COR$^{17}$, —NR$^{17a}R^{19a}$, and —CONR$^{17a}R^{19a}$ and each heteroaryl being substituted on any nitrogen atom with 0–1 substituents selected from the group $R^{15a}$, CO$_2 R^{14b}$, COR$^{14b}$ and SO$_2 R^{14b}$;
provided that $R^1$ is other than a —(CH$_2$)$_{1-4}$-aryl or —(CH$_2$)$_{1-4}$-heteroaryl wherein the aryl or heteroaryl group is substituted or unsubstituted;
$R^2$ is selected from the group $C_{1-4}$ alkyl, $C_{2-4}$ alkenyl, and $C_{2-4}$ alkynyl and is substituted with 0–1 substituents selected from the group —CN, OH, Cl, F, and $C_{1-4}$ alkoxy;

$R^7$ and $R^8$ are independently selected from the group H, Br, Cl, F, —CN, $C_{1-4}$ alkyl, $C_{3-6}$ cycloalkyl, $C_{1-4}$ alkoxy, NH$_2$, $C_{1-4}$ alkylamino, and (C$_{1-4}$ alkyl)$_2$-amino;
$R^9$ is independently selected at each occurrence from the group H, $C_{1-4}$ alkyl and $C_{3-8}$ cycloalkyl;
$R^{13}$ is selected from the group $C_{1-4}$ alkyl, $C_{1-2}$ haloalkyl, $C_{1-2}$ alkoxy-$C_{1-2}$ alkyl, $C_{3-6}$ cycloalkyl-$C_{1-2}$ alkyl, aryl (C$_{1-2}$ alkyl)-, and heteroaryl(C$_{1-2}$ alkyl)-;
$R^{13a}$ and $R^{16a}$ are independently selected at each occurrence from the group H. $C_{1-4}$ alkyl, $C_{1-4}$ haloalkyl, $C_{1-4}$ alkoxy-$C_{1-4}$ alkyl, $C_{3-6}$ cycloalkyl, and $C_{3-6}$ cycloalkyl-$C_{1-6}$ alkyl;
$R^{14}$ is selected from the group $C_{1-4}$ alkyl, $C_{1-2}$ haloalkyl, $C_{1-2}$ alkoxy-$C_{1-2}$ alkyl, $C_{3-6}$ cycloalkyl-$C_{1-2}$ alkyl, aryl (C$_{1-2}$ alkyl)-, and heteroaryl(C$_{1-2}$ alkyl)-;
$R^{14a}$ is selected from the group $C_{1-4}$ alkyl, $C_{1-2}$ haloalkyl, $C_{1-2}$ alkoxy-$C_{1-2}$ alkyl, and $C_{3-6}$ cycloalkyl-$C_{1-2}$ alkyl;
$R^{14b}$ is selected from the group $C_{1-4}$ alkyl, $C_{1-2}$ haloalkyl, $C_{1-2}$ alkoxy-$C_{1-2}$ alkyl, $C_{3-6}$ cycloalkyl, and $C_{3-6}$ cycloalkyl-$C_{1-2}$ alkyl;
$R^{15}$ is independently selected at each occurrence from the group H, $C_{1-4}$ alkyl, $C_{3-7}$ cycloalkyl, $C_{3-6}$ cycloalkyl-$C_{1-6}$ alkyl, phenyl and benzyl, each phenyl or benzyl being substituted on the aryl moiety with 0–3 groups chosen from the group $C_{1-4}$ alkyl, Br, Cl, F, $C_{1-4}$ haloalkyl, $C_{1-4}$ alkoxy, $C_{1-4}$ haloalkoxy, and dimethylamino;
$R^{15a}$ is independently selected at each occurrence from the group H, $C_{1-4}$ alkyl, $C_{3-7}$ cycloalkyl, and $C_{3-6}$ cycloalkyl-$C_{1-6}$ alkyl;
$R^{17}$, $R^{18}$ and $R^{19}$ are independently selected at each occurrence from the group H, $C_{1-6}$ alkyl, $C_{3-10}$ cycloalkyl, $C_{3-6}$ cycloalkyl-$C_{1-6}$ alkyl, $C_{1-2}$ alkoxy-$C_{1-2}$ alkyl, and $C_{1-4}$ haloalkyl;
alternatively, in an NR$^{17}R^{19}$ moiety, $R^{17}$ and $R^{19}$ taken together form 1-pyrrolidinyl, 1-morpholinyl, 1-piperidinyl or 1-piperazinyl, wherein N$_4$ in 1-piperazinyl is substituted with 0–1 substituents selected from the group $R^{13}$, CO$_2 R^{14}$, COR$^{14}$ and SO$_2 R^{14}$;
$R^{17a}$ and $R^{19a}$ are independently selected at each occurrence from the group H, $C_{1-6}$ alkyl, $C_{3-10}$ cycloalkyl, $C_{3-6}$ cycloalkyl-$C_{1-6}$ alkyl and $C_{1-4}$ haloalkyl;
aryl is phenyl substituted with 1–4 substituents independently selected at each occurrence from the group $C_{1-4}$ alkyl, $C_{3-6}$ cycloalkyl, —OR$^{17}$, Br, Cl, F, $C_{1-4}$ haloalkyl, —CN, —S(O)$_n R^{18}$, —COR$^{17}$, —CO$_2 R^{17}$, —NR$^{15}$COR$^{17}$, —NR$^{15}$CO$_2 R^{18}$, —NR$^{17}R^{19}$, and —CONR$^{17}R^{19}$; and,
heteroaryl is independently selected at each occurence from the group pyridyl, pyrimidinyl, triazinyl, furanyl, quinolinyl, isoquinolinyl, thienyl, thiazolyl, indolyl, pyrrolyl, oxazolyl, benzofuranyl, benzothienyl, benzothiazolyl, benzoxazolyl, isoxazolyl, tetrazolyl, indazolyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, benzoxazolin-2-on-yl, benzodioxolanyl and benzodioxane, each heteroaryl being substituted 1-4 carbon atoms with a substituent independently selected at each occurrence from the group $C_{1-6}$ alkyl, $C_{3-6}$ cycloalkyl, Br, Cl, F, $C_{1-4}$ haloalkyl, —CN, —OR$^{17}$, —S(O)$_m R^{18}$, —COR$^{17}$, —CO$_2 R^{17}$, —OC(O)R$^{18}$, —NR$^{15}$COR$^{17}$, —N(COR$^{17}$)$_2$, —NR$^{15}$CO$_2 R^{18}$, —NR$^{17}R^{19}$, and —CONR$^{17}R^{19}$ and each heteroaryl being substituted on any nitrogen atom with 0–1 substituents selected from the group $R^{15}$, $CO_2R^{14a}$, $COR^{14a}$ and $SO_2R^{14a}$.

[5b] In an even more preferred embodiment, the present invention provides a novel compound of formula Id, wherein:

X is selected from the group O, S and a bond $R^1$ is substituted $C_{1-6}$ alkyl;

$R^1$ is substituted with 0–1 substituents selected from the group —CN, —$CO_2R^{13a}$, and $C_{3-8}$ cycloalkyl, wherein 0–1 carbon atoms in the $C_{4-8}$ cycloalkyl is replaced by a group selected from the group —O—, —S(O)$_n$—, and —$NR^{13a}$—;

$R^1$ is also substituted with 0–2 substituents independently selected at each occurrence from the group $R^{1a}$, $R^{1b}$, $C_{1-6}$ alkyl, $C_{2-8}$ alkenyl, $C_{2-8}$ alkynyl, Br, Cl, F, $CF_3$, —$OR^{13a}$, —$NR^{13a}R^{16a}$, $C_{1-2}$ alkoxy-$C_{1-2}$ alkyl, and $C_{3-6}$ cycloalkyl which is substituted with 0–1 $CH_3$ and in which 0–1 carbons of $C_{4-8}$ cycloalkyl is replaced by —O—;

provided that $R^1$ is other than a cyclohexyl-$(CH_2)_2$- group;

$R^{1a}$ is aryl and is phenyl substituted with 0–1 substituents selected from $OCH_3$, $OCH_2CH_3$, $OCH(CH_3)_2$, $OCH_2CH_2CH_3$, and $OCF_3$, and 0–3 substituents independently selected at each occurrence from the group $CH_3$, $CH_2CH_3$, $CH(CH_3)_2$, $CH_2CH_2CH_3$, cyclopropyl, Br, Cl, F, $CF_3$, —CN, $SCH_3$, —$NH_2$, —$NHCH_3$, —$N(CH_3)_2$, —$C(O)NH_2$, —$C(O)NHCH_3$, and —$C(O)N(CH_3)_2$;

$R^{1b}$ is heteroaryl and is selected from the group furanyl, thienyl, imidazolyl, thiazolyl, oxazolyl, isoxazolyl, pyrazolyl, triazolyl, tetrazolyl, and indazolyl, each heteroaryl being substituted on 0–3 carbon atoms with a substituent independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, —$NH_2$, —$NHCH_3$, —$N(CH_3)_2$, —$C(O)NH_2$, —$C(O)NHCH_3$, and —$C(O)N(CH_3)_2$ and each heteroaryl being substituted on any nitrogen atom with 0–1 substituents selected from the group $CH_3$, $CO_2CH_3$, $COCH_3$ and $SO_2CH_3$;

provided that $R^1$ is other than a —$(CH_2)_{1-4}$-aryl or —$(CH_2)_{1-4}$-heteroaryl wherein the aryl or heteroaryl group is substituted or unsubstituted;

$R^2$ is selected from the group $CH_3$, $CH_2CH_3$, $CH(CH_3)_2$, and $CH_2CH_2CH_3$;

$R^7$ and $R^8$ are independently selected from the group H, $CH_3$, $CH_2CH_3$, $CH(CH_3)_2$, and $CH_2CH_2CH_3$;

aryl is phenyl substituted with 2–4 substituents independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, $SO_2CH_3$, —$NH_2$, —$NHCH_3$, —$N(CH_3)_2$, —$C(O)NH_2$, —$C(O)NHCH_3$, and —$C(O)N(CH_3)_2$; and, heteroaryl is independently selected at each occurence from the group pyridyl, indolyl, benzothienyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, and benzoxazolin-2-on-yl, each heteroaryl being substituted on 2–4 carbon atoms with a substituent independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, $SO_2CH_3$, —$NH_2$, —$NHCH_3$, —$N(CH_3)_2$, —$C(O)NH_2$, —$C(O)NHCH_3$, and —$C(O)N(CH_3)_2$ and each heteroaryl being substituted on any nitrogen atom with 0–1 substituents selected from the group $CH_3$, $CO_2CH_3$, $COCH_3$ and $SO_2CH_3$.

[5c] In a still more preferred embodiment, the present invention provides a novel compound of formula Id, wherein:

$R^1$ is substituted $C_1$;

$R^1$ is substituted with 0–1 substituents selected from the group —CN, —$CO_2CH_3$, and —$CO_2CH_2CH_3$;

$R^1$ is also substituted with 0–2 substituents independently selected at each occurrence from the group $R^{1a}$, $R^{1b}$, $CH_3$, $CH_2CH_3$, $CH(CH_3)2$, $CH_2CH_2CH_3$, —$(CH_2)_3CH_3$, —CH=$CH_2$, —CH=CH ($CH_3$), —CH≡CH, —CH≡C($CH_3$), $CH_2OCH_3$, —$CH_2CH_2OCH_3$, F, $CF_3$, cyclopropyl, $CH_3$-cyclopropyl, cyclobutyl, $CH_3$-cyclobutyl, cyclopentyl, $CH_3$-cyclopentyl;

$R^{1a}$ is phenyl substituted with 0–1 substituents selected from $OCH_3$, $OCH_2CH_3$, and $OCF_3$, and 0–2 substituents independently selected at each occurrence from the group $CH_3$, $CH_2CH_3$, $CH(CH_3)_2$, $CH_2CH_2CH_3$, Br, Cl, F, $CF_3$, —CN, and $SCH_3$;

$R^{1b}$ is heteroaryl and is selected from the group furanyl, thienyl, imidazolyl, thiazolyl, oxazolyl, isoxazolyl, pyrazolyl, triazolyl, and tetrazolyl, each heteroaryl being substituted on 0–3 carbon atoms with a substituent independently selected at each occurrence from the group $CH_3$, $CH_2CH_3$, $CH(CH_3)_2$, $CH_2CH_2CH_3$, $OCH_3$, $OCH_2CH_3$, $OCF_3$, Br, Cl, F, $CF_3$, —CN, and $SCH_3$ and each heteroaryl being substituted on any nitrogen atom with 0–1 substituents selected from the group $CH_3$, $CO_2CH_3$, $COCH_3$ and $SO_2CH_3$;

provided that $R^1$ is other than a —$(CH_2)_{1-4}$-aryl or —$(CH_2)_{1-4}$-heteroaryl wherein the aryl or heteroaryl group is substituted or unsubstituted;

$R^2$ is selected from the group $CH_3$, $CH_2CH_3$, and $CH(CH_3)_2$;

$R^7$ and $R^8$ are independently selected from the group H and $CH_3$;

aryl is phenyl substituted with 2–4 substituents independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, $SO_2CH_3$, —$NH_2$, —$NHCH_3$, —$N(CH_3)_2$, —$C(O)NH_2$, —$C(O)NHCH_3$, and —$C(O)N(CH_3)_2$; and, heteroaryl is pyridyl substituted on 2–4 carbon atoms with a substituent independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, $SO_2CH_3$, —$NH_2$, —$NHCH_3$, —$N(CH_3)_2$, —$C(O)NH_2$, —$C(O)NHCH_3$, and —$C(O)N(CH_3)_2$.

[5d] In a further preferred embodiment, the present invention provides a novel compound of formula Id, wherein:

$R^1$ is substituted (cyclopropyl)-$C_1$ alkyl or (cyclobutyl)-$C_1$ alkyl;

$R^1$ is substituted with 0–1 —CN;

$R^1$ is also substituted with 0–1 substituents independently selected at each occurrence from the group $R^{1a}$, $R^{1b}$, $CH_3$, $CH_2CH_3$, $CH(CH_3)_2$, $CH_2CH_2CH_3$, —$(CH_2)$ $_3CH_3$, —CH=$CH_2$, —CH=CH($CH_3$), —CH≡CH, —CH≡C($CH_3$), —$CH_2OCH_3$, —$CH_2CH_2OCH_3$, F, $CF_3$, cyclopropyl, and $CH_3$-cyclopropyl;

$R^{1a}$ is phenyl substituted with 0–1 substituents selected from $OCH_3$, $OCH_2CH_3$, and $OCF_3$, and 0–2 substituents independently selected at each occurrence from the group $CH_3$, $CH_2CH_3$, $CH(CH_3)_2$, $CH_2CH_2CH_3$, Br, Cl, F, $CF_3$, —CN, and $SCH_3$;

$R^{1b}$ is heteroaryl and is selected from the group furanyl, thienyl, imidazolyl, thiazolyl, oxazolyl, isoxazolyl, and pyrazolyl, each heteroaryl being substituted on 0–3 carbon atoms with a substituent independently selected at each occurrence from the group $CH_3$, $CH_2CH_3$, $CH(CH_3)_2$, $CH_2CH_2CH_3$, $OCH_3$, $OCH_2CH_3$, $OCF_3$, Br, Cl, F, $CF_3$, —CN, and $SCH_3$.

[5e] In another further preferred embodiment, the present invention provides a novel compound of formula Id, wherein:

$R^1$ is (cyclopropyl)$C_1$ alkyl or (cyclobutyl)-$C_1$ alkyl substituted with 1 substituent independently selected at each occurrence from the group $R^{1a}$, $R^{1b}$, $CH_3$, $CH_2CH_3$, $CH(CH_3)_2$, $CH_2CH_2CH_3$, —$(CH_2)_3CH_3$, —CH=$CH_2$, —CH=CH($CH_3$), —CH≡CH, —CH≡C($CH_3$), —$CH_2OCH_3$, —$CH_2CH_2OCH_3$, F, $CF_3$, cyclopropyl, and $CH_3$-cyclopropyl;

$R^{1a}$ is phenyl substituted with 0–2 substituents independently selected at each occurrence from the group $CH_3$, $CH_2CH_3$, Cl, F, and $CF_3$;

$R^{1b}$ is heteroaryl and is selected from the group furanyl, thienyl, and isoxazolyl, each heteroaryl being substituted on 0–2 carbon atoms with a substituent independently selected at each occurrence from the group $CH_3$, $OCH_3$, Cl, F, and $CF_3$.

[5f] In an even further preferred embodiment, the present invention provides a novel compound of formula Id, wherein:

$R^1$ is selected from the group $R^1$ is selected from the group (cyclopropyl)CH—$CH_3$, (cyclopropyl)CH—$CH_2CH_3$, (cyclopropyl)CH—$CH_2OCH_3$, (cyclopropyl)CH—$CH_2CH_2CH_3$, (cyclopropyl)CH—$CH_2CH_2OCH_3$, (cyclopropyl)$_2$CH, phenyl(cyclopropyl)CH, furanyl(cyclopropyl)CH, thienyl(cyclopropyl)CH, isoxazolyl(cyclopropyl)CH, ($CH_3$-furanyl)(cyclopropyl)CH, (cyclobutyl)CH—$CH_3$, (cyclobutyl)CH—$CH_2CH_3$, (cyclobutyl)CH—$CH_2OCH_3$, (cyclobutyl)CH—$CH_2CH_2CH_3$, (cyclobutyl)CH—$CH_2CH_2OCH_3$, (cyclobutyl)$_2$CH, phenyl(cyclobutyl)CH, furanyl(cyclobutyl)CH, thienyl(cyclobutyl)CH, isoxazolyl(cyclobutyl)CH, and ($CH_3$-furanyl)(cyclobutyl)CH;

[5g] In another further preferred embodiment, the present invention provides a novel compound of formula Id, wherein:

D is phenyl substituted with 2–4 substituents independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, and $CF_3$.

[5h] In another further preferred embodiment, the present invention provides a novel compound of formula Id, wherein:

D is pyridyl substituted on 2–4 carbon atoms with a substituent independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, and $CF_3$.

[5i] In another preferred embodiment, the present invention provides a novel compound of formula Id, wherein the compound is selected from the group:

4-(2,4-Dichlorophenyl)-2-ethyl-1-(1-ethyl)propyl-imidazo[4,5-c]pyridine;

4-(2,4-Dichlorophenyl)-2-ethyl-1-(1-cyclopropyl)propyl-imidazo[4,5-c]pyridine;

4-(2,4-Dichlorophenyl)-2-ethyl-1-(1-cyclopropyl)butyl-imidazo[4,5-c]pyridine;

4-(2,4-Dichlorophenyl)-2-ethyl-3-(1-methoxy)butyl-imidazo[4,5-c]pyridine;

4-(2-Chloro-4-trifluoromethylphenyl)-2-ethyl-1-(1-cyclopropyl)propyl-imidazo[4,5-c]pyridine;

4-(2-Chloro-4-trifluoromethylphenyl)-2-ethyl-1-(1-cyclopropyl)butyl-imidazo[4,5-c]pyridine;

4-(2-Chloro-4-trifluoromethylphenyl)-2-ethyl-3-(1-methoxy)butyl-imidazo[4,5-c]pyridine;

4-(2-Chloro-4-methoxyphenyl)-2-ethyl-i-(1-cyclopropyl)propyl-imidazo[4,5-c]pyridine;

4-(2-Chloro-4-methoxyphenyl)-2-ethyl-i-(1-cyclopropyl)butyl-imidazo[4,5-c]pyridine;

4-(2-Chloro-4-methoxyphenyl)-2-ethyl-3-(1-methoxy)butyl-imidazo[4,5-c]pyridine;

4-(2-Methyl-4-methoxy-5-fluorophenyl)-2-ethyl-1-(1-cyclopropyl)propyl-imidazo[4,5-c]pyridine;

4-(2-Methyl-4-methoxy-5-fluorophenyl)-2-ethyl-1-(1-cyclopropyl)butyl-imidazo[4,5-c]pyridine;

4-(2-Methyl-4-methoxy-5-fluorophenyl)-2-ethyl-3-(1-methoxy)butyl-imidazo[4,5-c]pyridine;

4-(2,4-Dichlorophenyl)-2-ethyl-1-(1-ethyl)propyl-imidazo[4,5-d]pyridazine;

4-(2,4-Dichlorophenyl)-2-ethyl-1-(1-cyclopropyl)propyl-imidazo[4,5-d]pyridazine;

4-(2,4-Dichlorophenyl)-2-ethyl-1-(1-cyclopropyl)butyl-imidazo[4,5-d]pyridazine;

4-(2,4-Dichlorophenyl)-2-ethyl-3-(1-methoxy)butyl-imidazo[4,5-d]pyridazine;

4-(2-Chloro-4-trifluoromethylphenyl)-2-ethyl-1-(1-cyclopropyl)propyl-imidazo[4,5-d]pyridazine;

4-(2-Chloro-4-trifluoromethylphenyl)-2-ethyl-1-(1-cyclopropyl)butyl-imidazo[4,5-d]pyridazine;

4-(2-Chloro-4-trifluoromethylphenyl)-2-ethyl-3-(1-methoxy)butyl-imidazo[4,5-d]pyridazine;

4-(2-Chloro-4-methoxyphenyl)-2-ethyl-1-(1-cyclopropyl)propyl-imidazo[4,5-d]pyridazine;

4-(2-Chloro-4-methoxyphenyl)-2-ethyl-1-(1-cyclopropyl)butyl-imidazo[4,5-d]pyridazine;

4-(2-Chloro-4-methoxyphenyl)-2-ethyl-3-(1-methoxy)butyl-imidazo[4,5-d]pyridazine;

4-(2-Methyl-4-methoxy-5-fluorophenyl)-2-ethyl-1-(1-cyclopropyl)propyl-imidazo[4,5-d]pyridazine;

4-(2-Methyl-4-methoxy-5-fluorophenyl)-2-ethyl-1-(1-cyclopropyl)butyl-imidazo[4,5-d]pyridazine;

4-(2-Methyl-4-methoxy-5-fluorophenyl)-2-ethyl-3-(1-methoxy)butyl-imidazo[4,5-d]pyridazine;

4-(2,4-Dichlorophenyl)-2-ethyl-1-(1-ethyl)propyl-imidazo[4,5-c]pyridazine;

4-(2,4-Dichlorophenyl)-2-ethyl-1-(1-cyclopropyl)propyl-imidazo[4,5-c]pyridazine;

4-(2,4-Dichlorophenyl)-2-ethyl-1-(1-cyclopropyl)butyl-imidazo[4,5-c]pyridazine;

4-(2,4-Dichlorophenyl)-2-ethyl-3-(1-methoxy)butyl-imidazo[4,5-c]pyridazine;

4-(2-Chloro-4-trifluoromethylphenyl)-2-ethyl-1-(1-cyclopropyl)propyl-imidazo[4,5-c]pyridazine;

4-(2-Chloro-4-trifluoromethylphenyl)-2-ethyl-1-(1-cyclopropyl)butyl-imidazo[4,5-c]pyridazine;

4-(2-Chloro-4-trifluoromethylphenyl)-2-ethyl-3-(1-methoxy)butyl-imidazo[4,5-c]pyridazine;

4-(2-Chloro-4-methoxyphenyl)-2-ethyl-1-(1-cyclopropyl)propyl-imidazo[4,5-c]pyridazine;

4-(2-Chloro-4-methoxyphenyl)-2-ethyl-1-(1-cyclopropyl)butyl-imidazo[4,5-c]pyridazine;

4-(2-Chloro-4-methoxyphenyl)-2-ethyl-3-(1-methoxy)butyl-imidazo[4,5-c]pyridazine;

4-(2-Methyl-4-methoxy-5-fluorophenyl)-2-ethyl-1-(1-cyclopropyl)propyl-imidazo[4,5-c]pyridazine;

4-(2-Methyl-4-methoxy-5-fluorophenyl)-2-ethyl-1-(1-cyclopropyl)butyl-imidazo[4,5-c]pyridazine;

4-(2-Methyl-4-methoxy-5-fluorophenyl)-2-ethyl-3-(1-methoxy)butyl-imidazo[4,5-c]pyridazine;

4-(2,4-Dichlorophenyl)-2-ethyl-1-(1-ethyl)propyl-imidazo[4,5-d]triazine;

4-(2,4-Dichlorophenyl)-2-ethyl-1-(1-cyclopropyl)propyl-imidazo[4,5-d]triazine;

4-(2,4-Dichlorophenyl)-2-ethyl-1-(1-cyclopropyl)butyl-imidazo[4,5-d]triazine;

4-(2,4-Dichlorophenyl)-2-ethyl-3-(1-methoxy)butyl-imidazo[4,5-d]triazine;

4-(2-Chloro-4-trifluoromethylphenyl)-2-ethyl-1-(1-cyclopropyl)propyl-imidazo[4,5-d]triazine;

4-(2-Chloro-4-trifluoromethylphenyl)-2-ethyl-1-(1-cyclopropyl)butyl-imidazo[4,5-d]triazine;

4-(2-Chloro-4-trifluoromethylphenyl)-2-ethyl-3-(1-methoxy)butyl-imidazo[4,5-d]triazine;

4-(2-Chloro-4-methoxyphenyl)-2-ethyl-1-(1-cyclopropyl)propyl-imidazo[4,5-d]triazine;

4-(2-Chloro-4-methoxyphenyl)-2-ethyl-1-(1-cyclopropyl)butyl-imidazo[4,5-d]triazine;

4-(2-Chloro-4-methoxyphenyl)-2-ethyl-3-(1-methoxy)butyl-imidazo[4,5-d]triazine;

4-(2-Methyl-4-methoxy-5-fluorophenyl)-2-ethyl-1-(1-cyclopropyl)propyl-imidazo[4,5-d]triazine;

4-(2-Methyl-4-methoxy-5-fluorophenyl)-2-ethyl-1-(1-cyclopropyl)butyl-imidazo[4,5-d]triazine; and, 4-(2-Methyl-4-methoxy-5-fluorophenyl)-2-ethyl-3-(1-methoxy)butyl-imidazo[4,5-d]triazine;

or a pharmaceutically acceptable salt form thereof.

[5j] In another more preferred embodiment, the present invention provides a novel compound of formula Id, wherein:

$R^1$ is $C_{3-8}$ cycloalkyl;

$R^1$ is substituted with 0–1 substituents selected from the group —CN, —S(O)$_n$R$^{14b}$, —COR$^{13a}$, —CO$_2$R$^{13a}$, —NR$^{15a}$COR$^{13a}$, —N(COR$^{13a}$)$_2$, —NR$^{15a}$CONR$^{13a}$R$^{16a}$, —NR$^{15a}$CO$_2$R$^{14b}$, —CONR$^{13a}$R$^{16a}$, 1-morpholinyl, 1-piperidinyl, 1-piperazinyl, and $C_{4-8}$ cycloalkyl, wherein 0–1 carbon atoms in the $C_{4-8}$ cycloalkyl is replaced by a group selected from the group —O—, —S(O)$_n$—, —NR$^{13a}$—, —NCO$_2$R$^{14b}$—, —NCOR$^{14b}$— and —NSO$_2$R$^{14b}$—, and wherein N$_4$ in 1-piperazinyl is substituted with 0–1 substituents selected from the group R$^{13a}$, CO$_2$R$^{14b}$, COR$^{14b}$ and SO$_2$R$^{14b}$; and, $R^1$ is also substituted with 0–3 substituents independently selected at each occurrence from the group R$^{1a}$, R$^{1b}$, R$^{1c}$, $C_{1-6}$ alkyl, $C_{2-8}$ alkenyl, $C_{2-8}$ alkynyl, Br, Cl, F, I, $C_{1-4}$ haloalkyl, —OR$^{13a}$, $C_{1-2}$ alkoxy-$C_{1-2}$ alkyl, and —NR$^{13a}$R$^{16a}$.

[5k] In another even more preferred embodiment, the present invention provides a novel compound of formula Id, wherein:

X is selected from the group O, S(O)$_n$ and a bond;

n is 0, 1 or 2;

$R^1$ is selected from the group cyclopropyl, cyclobutyl, and cyclopentyl;

$R^1$ is substituted with 0–1 substituents selected from the group —CN, —S(O)$_n$R$^{14b}$, —COR$^{13a}$, —CO$_2$R$^{13a}$, and $C_{4-8}$ cycloalkyl, wherein one carbon atom in the $C_{4-8}$ cycloalkyl is replaced by a group selected from the group —O—, —S(O)$_n$—, —NR$^{13a}$—, —NCO$_2$R$^{14b}$—, —NCOR$^{14b}$— and —NSO$_2$R$^{14b}$—;

$R^1$ is also substituted with 0–2 substituents independently selected at each occurrence from the group R$^{1a}$, R$^{1b}$, $C_{1-6}$ alkyl, $C_{2-8}$ alkenyl, $C_{2-8}$ alkynyl, Br, Cl, F, CF$_3$, CF$_2$CF$_3$, —OR$^{13a}$, $C_{1-2}$ alkoxy-$C_{1-2}$ alkyl, and —NR$^{13a}$R$^{16a}$;

$R^{1a}$ is aryl and is selected from the group phenyl and indanyl, each $R^{1a}$ being substituted with 0–1 —OR$^{17}$ and 0–5 substituents independently selected at each occurrence from the group $C_{1-4}$ alkyl, $C_{3-6}$ cycloalkyl, Br, Cl, F, $C_{1-4}$ haloalkyl, —CN, —S(O)$_n$R$^{18}$, —COR$^{17}$, —NR$^{17a}$R$^{19a}$, and —CONR$^{17a}$R$^{19a}$;

$R^{1b}$ is heteroaryl and is selected from the group pyridyl, pyrimidinyl, furanyl, thienyl, imidazolyl, thiazolyl, pyrrolyl, oxazolyl, isoxazolyl, pyrazolyl, triazolyl, tetrazolyl, and indazolyl, each heteroaryl being substituted on 0–4 carbon atoms with a substituent independently selected at each occurrence from the group $C_{1-4}$ alkyl, $C_{3-6}$ cycloalkyl, Br, Cl, F, CF$_3$, —CN, —OR$^{17}$, —S(O)$_m$R$^{18}$, —COR$^{17}$, —NR$^{17a}$R$^{19a}$, and —CONR$^{17a}$R$^{19a}$ and each heteroaryl being substituted on any nitrogen atom with 0–1 substituents selected from the group R$^{15a}$, CO$_2$R$^{14b}$, COR$^{14b}$ and SO$_2$R$^{14b}$;

$R^2$ is selected from the group $C_{1-4}$ alkyl, $C_{2-4}$ alkenyl, and $C_{2-4}$ alkynyl and is substituted with 0–1 substituents selected from the group —CN, OH, Cl, F, and $C_{1-4}$ alkoxy;

$R^9$ is independently selected at each occurrence from the group H, $C_{1-4}$ alkyl and $C_{3-8}$ cycloalkyl;

$R^7$ and $R^8$ are independently selected from the group H, Br, Cl, F, —CN, $C_{1-4}$ alkyl, $C_{3-6}$ cycloalkyl, $C_{1-4}$ alkoxy, NH$_2$, $C_{1-4}$ alkylamino, and ($C_{1-4}$ alkyl)$_2$-amino;

$R^{13}$ is selected from the group $C_{1-4}$ alkyl, $C_{1-2}$ haloalkyl, $C_{1-2}$ alkoxy-$C_{1-2}$ alkyl, $C_{3-6}$ cycloalkyl-$C_{1-2}$ alkyl, aryl ($C_{1-2}$ alkyl)-, and heteroaryl($C_{1-2}$ alkyl)-;

$R^{13a}$ and $R^{16a}$ are independently selected at each occurrence from the group H, $C_{1-4}$ alkyl, $C_{1-4}$ haloalkyl, $C_{1-4}$ alkoxy-$C_{1-4}$ alkyl, $C_{3-6}$ cycloalkyl, and $C_{3-6}$ cycloalkyl-$C_{1-6}$ alkyl;

$R^{14}$ is selected from the group $C_{1-4}$ alkyl, $C_{1-2}$ haloalkyl, $C_{1-2}$ alkoxy-$C_{1-2}$ alkyl, $C_{3-6}$ cycloalkyl-$C_{1-2}$ alkyl, aryl ($C_{1-2}$ alkyl)-, and heteroaryl($C_{1-2}$ alkyl)-;

$R^{14a}$ is selected from the group $C_{1-4}$ alkyl, $C_{1-2}$ haloalkyl, $C_{1-2}$ alkoxy-$C_{1-2}$ alkyl, and $C_{3-6}$ cycloalkyl-$C_{1-2}$ alkyl;

$R^{14b}$ is selected from the group $C_{1-4}$ alkyl, $C_{1-2}$ haloalkyl, $C_{1-2}$ alkoxy-$C_{1-2}$ alkyl, $C_{3-6}$ cycloalkyl, and $C_{3-6}$ cycloalkyl-$C_{1-2}$ alkyl;

$R^{15}$ is independently selected at each occurrence from the group H, $C_{1-4}$ alkyl, $C_{3-7}$ cycloalkyl, $C_{3-6}$ cycloalkyl- $C_{1-6}$ alkyl, phenyl and benzyl, each phenyl or benzyl being substituted on the aryl moiety with 0–3 groups chosen from the group $C_{1-4}$ alkyl, Br, Cl, F, $C_{1-4}$ haloalkyl, $C_{1-4}$ alkoxy, $C_{1-4}$ haloalkoxy, and dimethylamino;

$R^{15a}$ is independently selected at each occurrence from the group H, $C_{1-4}$ alkyl, $C_{3-7}$ cycloalkyl, and $C_{3-6}$ cycloalkyl-$C_{1-6}$ alkyl;

$R^{17}$, $R^{18}$ and $R^{19}$ are independently selected at each occurrence from the group H, $C_{1-6}$ alkyl, $C_{3-10}$ cycloalkyl, $C_{3-6}$ cycloalkyl-$C_{1-6}$ alkyl, $C_{1-2}$ alkoxy-$C_{1-2}$ alkyl, and $C_{1-4}$ haloalkyl;

alternatively, in an $NR^{17}R^{19}$ moiety, $R^{17}$ and $R^{19}$ taken together form 1-pyrrolidinyl, 1-morpholinyl, 1-piperidinyl or 1-piperazinyl, wherein $N_4$ in 1-piperazinyl is substituted with 0–1 substituents selected from the group $R^{13}$, $CO_2R^{14}$, $COR^{14}$ and $SO_2R^{14}$;

$R^{17a}$ and $R^{19a}$ are independently selected at each occurrence from the group H, $C_{1-6}$ alkyl, $C_{3-10}$ cycloalkyl, $C_{3-6}$ cycloalkyl-$C_{1-6}$ alkyl and $C_{1-4}$ haloalkyl;

aryl is phenyl substituted with 1–4 substituents independently selected at each occurrence from the group $C_{1-4}$ alkyl, $C_{3-6}$ cycloalkyl, $-OR^{17}$, Br, Cl, F, $C_{1-4}$ haloalkyl, $-CN$, $-S(O)_nR^{18}$, $-COR^{17}$, $-CO_2R^{17}$, $-NR^{15}COR^{17}$, $-NR^{15}CO_2R^{18}$, $-NR^{17}R^{19}$, and $-CONR^{17}R^{19}$; and, heteroaryl is independently selected at each occurence from the group pyridyl, pyrimidinyl, triazinyl, furanyl, quinolinyl, isoquinolinyl, thienyl, thiazolyl, indolyl, pyrrolyl, oxazolyl, benzofuranyl, benzothienyl, benzothiazolyl, benzoxazolyl, isoxazolyl, tetrazolyl, indazolyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, benzoxazolin-2-on-yl, benzodioxolanyl and benzodioxane, each heteroaryl being substituted 1–4 carbon atoms with a substituent independently selected at each occurrence from the group $C_{1-6}$ alkyl, $C_{3-6}$ cycloalkyl, Br, Cl, F, $C_{1-4}$ haloalkyl, $-CN$, $-OR^{17}$, $-S(O)_mR^{18}$, $-COR^{17}$, $-CO_2R^{17}$, $-OC(O)R^{18}$, $-NR^{15}COR^{17}$, $-N(COR^{17})_2$, $-NR^{15}CO_2R^{18}$, $-NR^{17}R^{19}$, and $-CONR^{17}R^{19}$ and each heteroaryl being substituted on any nitrogen atom with 0–1 substituents selected from the group $R^{15}$, $CO_2R^{14a}$, $COR^{14a}$ and $SO_2R^{14a}$.

[5l] In another still more preferred embodiment, the present invention provides a novel compound of formula Id, wherein:

X is selected from the group O, S and a bond $R^1$ is substituted with 0–1 substituents selected from the group $-CN$, $-CO_2R^{13a}$, and $C_{4-8}$ cycloalkyl, wherein 0–1 carbon atoms in the $C_{4-8}$ cycloalkyl is replaced by a group selected from the group $-O-$, $-S(O)_n-$, and $-NR^{13a}-$;

$R^1$ is also substituted with 0–2 substituents independently selected at each occurrence from the group $R^{1a}$, $R^{1b}$, $C_{1-6}$ alkyl, $C_{2-8}$ alkenyl, $C_{2-8}$ alkynyl, Br, Cl, F, $CF_3$, $CF_3$, $-OR^{13a}$, $-OH$, $-OCH_3$, $-OCH_2CH_3$, $-CH_2OCH_3$, $-CH_2CH_2OCH_3$, and $-NR^{13a}R^{16a}$;

$R^{1a}$ is aryl and is phenyl substituted with 0–1 substituents selected from $OCH_3$, $OCH_2CH_3$, $OCH(CH_3)_2$, $OCH_2CH_2CH_3$, and $OCF_3$, and 0–3 substituents independently selected at each occurrence from the group $CH_3$, $CH_2CH_3$, $CH(CH_3)_2$, $CH_2CH_2CH_3$, cyclopropyl, Br, Cl, F, $CF_3$, $-CN$, $SCH_3$, $-NH_2$, $-NHCH_3$, $-N(CH_3)_2$, $-C(O)NH_2$, $-C(O)NHCH_3$, and $-C(O)N(CH_3)_2$;

$R^{1b}$ is heteroaryl and is selected from the group furanyl, thienyl, imidazolyl, thiazolyl, oxazolyl, isoxazolyl, pyrazolyl, triazolyl, tetrazolyl, and indazolyl, each heteroaryl being substituted on 0–3 carbon atoms with a substituent independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, $-CN$, $SCH_3$, $-NH_2$, $-NHCH_3$, $-N(CH_3)_2$, $-C(O)NH_2$, $-C(O)NHCH_3$, and $-C(O)N(CH_3)_2$ and each heteroaryl being substituted on any nitrogen atom with 0–1 substituents selected from the group $CH_3$, $CO_2CH_3$, $COCH_3$ and $SO_2CH_3$;

$R^2$ is selected from the group $CH_3$, $CH_2CH_3$, $CH(CH_3)_2$, and $CH_2CH_2CH_3$;

$R^7$ and $R^8$ are independently selected from the group H, $CH_3$, $CH_2CH_3$, $CH(CH_3)_2$, and $CH_2CH_2CH_3$;

aryl is phenyl substituted with 2–4 substituents independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, $-CN$, $SCH_3$, $SO_2CH_3$, $-NH_2$, $-NHCH_3$, $-N(CH_3)_2$, $-C(O)NH_2$, $-C(O)NHCH_3$, and $-C(O)N(CH_3)_2$; and, heteroaryl is independently selected at each occurence from the group pyridyl, indolyl, benzothienyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, and benzoxazolin-2-on-yl, each heteroaryl being substituted on 2–4 carbon atoms with a substituent independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)2$, $OCH_2CH_2CH_3$, $OCF_3$, Br, Cl, F, $CF_3$, $-CN$, $SCH_3$, $SO_2CH_3$, $-NH_2$, $-NHCH_3$, $-N(CH_3)_2$, $-C(O)NH_2$, $-C(O)NHCH_3$, and $-C(O)N(CH_3)_2$ and each heteroaryl being substituted on any nitrogen atom with 0–1 substituents selected from the group $CH_3$, $CO_2CH_3$, $COCH_3$ and $SO_2CH_3$.

[5m] In another further preferred embodiment, the present invention provides a novel compound of formula Id, wherein:

$R^1$ is substituted with 0–2 substituents independently selected at each occurrence from the group $R^{1a}$, $R^{1b}$, $CH_3$, $CH_2CH_3$, $CH(CH_3)_2$, $CH_2CH_2CH_3$, $-(CH_2)_3CH_3$, $-CH=CH_2$, $-CH=CH(CH_3)$, $-CH\equiv CH$, $-CH\equiv C(CH_3)$, $-CH_2OCH_3$, $-CH_2CH_2OCH_3$, F, and $CF_3$;

$R^{1a}$ is phenyl substituted with 0–1 substituents selected from $OCH_3$, $OCH_2CH_3$, $OCH(CH_3)_2$, $OCH_2CH_2CH_3$, and $OCF_3$, and 0–2 substituents independently selected at each occurrence from the group $CH_3$, $CH_2CH_3$, $CH(CH_3)_2$, $CH_2CH_2CH_3$, Br, Cl, F, $CF_3$, $-CN$, and $SCH_3$;

$R^{1b}$ is heteroaryl and is selected from the group furanyl, thienyl, imidazolyl, thiazolyl, oxazolyl, isoxazolyl, pyrazolyl, triazolyl, and tetrazolyl, each heteroaryl being substituted on 0–3 carbon atoms with a substituent independently selected at each occurrence from the group $CH_3$, $CH_2CH_3$, $CH(CH_3)_2$, $CH_2CH_2CH_3$, $OCH_3$, $OCH_2CH_3$, $OCF_3$, Br, Cl, F, $CF_3$, $-CN$, and $SCH_3$ and each heteroaryl being substituted on any nitrogen atom with 0–1 substituents selected from the group $CH_3$, $CO_2CH_3$, $COCH_3$ and $SO_2CH_3$;

$R^2$ is selected from the group $CH_3$, $CH_2CH_3$, and $CH(CH_3)_2$;

$R^7$ and $R^8$ are independently selected from the group H and $CH_3$;

aryl is phenyl substituted with 2–4 substituents independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, $SO_2CH_3$, —$NH_2$, —$NHCH_3$, —$N(CH_3)_2$, —$C(O)NH_2$, —$C(O)NHCH_3$, and —$C(O)N(CH_3)_2$; and, heteroaryl is pyridyl substituted on 2–4 carbon atoms with a substituent independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, $SO_2CH_3$, —$NH_2$, —$NHCH_3$, —$N(CH_3)_2$, —$C(O)NH_2$, —$C(O)NHCH_3$, and —$C(O)N(CH_3)_2$.

[5n] In another even further preferred embodiment, the present invention provides a novel compound of formula Id, wherein:

$R^1$ is substituted with 0–2 substituents independently selected at each occurrence from the group $R^{1a}$, $CH_3$, $CH_2CH_3$, $CH(CH_3)_2$, $CH_2CH_2CH_3$, —$(CH_2)_3CH_3$, —$CH_2OCH_3$, —$CH_2CH_2OCH_3$, F, and $CF_3$; and, $R^{1a}$ is phenyl substituted with 0–2 substituents independently selected at each occurrence from the group $CH_3$, $CH_2CH_3$, $CH(CH_3)_2$, $CH_2CH_2CH_3$, Br, Cl, F, $CF_3$, —CN, and $SCH_3$.

[5o] In a still further preferred embodiment, the present invention provides a novel compound of formula Id, wherein:

D is phenyl substituted with 2–4 substituents independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, and $CF_3$.

[5p] In another still further preferred embodiment, the present invention provides a novel compound of formula Id, wherein:

D is pyridyl substituted on 2–4 carbon atoms with a substituent independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, and $CF_3$.

[5q] In another more preferred embodiment, the present invention provides a novel compound of formula Id, wherein:

$R^1$ is selected from the group $C_{1-10}$ alkyl, $C_{2-10}$ alkenyl, $C_{2-10}$ alkynyl, $C_{3-8}$ cycloalkyl, $C_{3-6}$ cycloalkyl-$C_{1-6}$ alkyl and $C_{1-4}$ alkoxy-$C_{1-4}$ alkyl;

$R^1$ is substituted with a $C_{3-8}$ cycloalkyl group, wherein 0–1 carbon atoms in the $C_{4-8}$ cycloalkyl group is replaced by a group selected from the group —O—, —$S(O)_n$—, —$NR^{13a}$—, —$NCO_2R^{14b}$—, —$NCOR^{14b}$ and —$NSO_2R^{14b}$—;

$R^1$ is also substituted with 0–3 substituents independently selected at each occurrence from the group $R^{1a}$, $R^{1b}$, $R^{1c}$, $C_{1-6}$ alkyl, $C_{2-8}$ alkenyl, $C_{2-8}$ alkynyl, Br, Cl, F, I, $C_{1-4}$ haloalkyl, —$OR^{13a}$, —$NR^{13a}R^{16a}$, $C_{1-2}$ alkoxy-$C_{1-2}$ alkyl, and $C_{3-8}$ cycloalkyl which is substituted with 0–1 $R^9$ and in which 0–1 carbons of $C_{4-8}$ cycloalkyl is replaced by —O—;

provided that $R^1$ is other than a cyclohexyl-$(CH_2)_2$- group;

$R^1a$ is aryl and is selected from the group phenyl, naphthyl, indanyl and indenyl, each $R^{1a}$ being substituted with 0–1 —$OR^{17}$ and 0–5 substituents independently selected at each occurrence from the group $C_{1-6}$ alkyl, $C_{3-6}$ cycloalkyl, Br, Cl, F, I, $C_{1-4}$ haloalkyl, —CN, nitro, SH, —$S(O)_nR^{18}$, —$COR^{17}$, —$OC(O)R^{18}$, —$NR^{15a}COR^{17}$, —$N(COR^{17})_2$, —$NR^{15a}CONR^{17a}R^{19a}$, —$NR^{15a}CO_2R^{18}$, —$NR^{17a}R^{19a}$, and —$CONR^{17a}R^{19a}$;

$R^{1b}$ is heteroaryl and is selected from the group pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, pyrazolyl, triazolyl, tetrazolyl, indazolyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, benzoxazolin-2-onyl, benzodioxolanyl and benzodioxane, each heteroaryl being substituted on 0–4 carbon atoms with a substituent independently selected at each occurrence from the group $C_{1-6}$ alkyl, $C_{3-6}$ cycloalkyl, Br, Cl, F, I, $C_{1-4}$ haloalkyl, —CN, —$OR^{17}$, SH, —$S(O)_mR^{18}$, —$COR^{17}$, —$OC(O)R^{18}$, —$NR^{15a}COR^{17}$, —$N(COR^{17})_2$, —$NR^{15a}CONR^{17a}R^{19a}$, —$NR^{15a}CO_2R^{18}$, —$NR^{17a}R^{19a}$, and $CONR^{17a}R^{19a}$, and each heteroaryl being substituted on any nitrogen atom with 0–1 substituents selected from the group $R^{15a}$, $CO_2R^{14b}$, $COR^{14b}$ and $SO_2R^{14b}$; and, $R^{1c}$ is heterocyclyl and is a saturated or partially saturated heteroaryl, each heterocyclyl being substituted on 0–4 carbon atoms with a substituent independently selected at each occurrence from the group $C_{1-6}$ alkyl, $C_{3-6}$ cycloalkyl, Br, Cl, F, I, $C_{1-4}$ haloalkyl, —CN, nitro, —$OR^{13a}$, SH, —$S(O)_nR^{14b}$, —$COR^{13a}$, —$CC(O)R^{14b}$, —$NR^{15a}COR^{13a}$, —$N(COR^{13a})_2$, —$NR^{15a}CONR^{13a}R^{16a}$, —$NR^{15a}CO_2R^{14b}$, —$NR^{13a}R^{16a}$, and —$CONR^{13a}R^{16a}$ and each heterocyclyl being substituted on any nitrogen atom with 0–1 substituents selected from the group $R^{13a}$, $CO_2R^{14b}$, $COR^{14b}$ and $SO_2R^{14b}$ and wherein any sulfur atom is optionally monooxidized or dioxidized.

[5r] In another even more preferred embodiment, the present invention provides a novel compound of formula Id, wherein:

X is selected from the group O, $S(O)_n$ and a bond;

n is 0, 1 or 2;

$R^1$ is selected from the group $C_{1-6}$ alkyl, $C_{2-6}$ alkenyl, $C_{2-6}$ alkynyl, and $C_{3-8}$ cycloalkyl;

$R^1$ is substituted with a $C_{3-6}$ cycloalkyl group, wherein 0–1 carbon atoms in the $C_{4-6}$ cycloalkyl group is replaced by a group selected from the group —O—, —$S(O)_n$—, and —$NR^{13a}$—;

$R^1$ is also substituted with 0–2 substituents independently selected at each occurrence from the group $R^{1a}$, $R^{1b}$, $C_{1-6}$ alkyl, $C_{2-8}$ alkenyl, $C_{2-8}$ alkynyl, Br, Cl, F, $CF_3$, $CF_2CF_3$, —$OR^{13a}$, —$NR^{13a}R^{16a}$, $C_{1-2}$ alkoxy-$C_{1-2}$ alkyl, and $C_{3-6}$ cycloalkyl which is substituted with 0–1 $R^9$ and in which 0–1 carbons of $C_{4-8}$ cycloalkyl is replaced by —O—;

$R^{1a}$ is aryl and is selected from the group phenyl and indanyl, each $R^{1a}$ being substituted with 0–1 —$OR^{17}$ and 0–5 substituents independently selected at each occurrence from the group $C_{1-4}$ alkyl, $C_{3-6}$ cycloalkyl, Br, Cl, F, $C_{1-4}$ haloalkyl, —CN, —S(O)$_n$R$^{18}$, —COR$^{17}$, —NR$^{17a}$R$^{19a}$, and —CONR$^{17a}$R$^{19a}$;

R$^{1b}$ is heteroaryl and is selected from the group pyridyl, pyrimidinyl, furanyl, thienyl, imidazolyl, thiazolyl, pyrrolyl, oxazolyl, isoxazolyl, pyrazolyl, triazolyl, tetrazolyl, and indazolyl, each heteroaryl being substituted on 0–4 carbon atoms with a substituent independently selected at each occurrence from the group $C_{1-4}$ alkyl, $C_{3-6}$ cycloalkyl, Br, Cl, F, CF$_3$, —CN, —OR$^{17}$, —S(O)$_m$R$^{18}$, —COR$^{17}$, —NR$^{17a}$R$^{19a}$, and —CONR$^{17a}$R$^{19a}$ and each heteroaryl being substituted on any nitrogen atom with 0–1 substituents selected from the group R$^{15a}$, CO$_2$R$^{14b}$, COR$^{14b}$ and SO$_2$R$^{14b}$;

R$^2$ is selected from the group $C_{1-4}$ alkyl, $C_{2-4}$ alkenyl, and $C_{2-4}$ alkynyl and is substituted with 0–1 substituents selected from the group —CN, OH, Cl, F, and $C_{1-4}$ alkoxy;

R$^7$ and R$^8$ are independently selected from the group H, Br, Cl, F, —CN, $C_{1-4}$ alkyl, $C_{3-6}$ cycloalkyl, $C_{1-4}$ alkoxy, NH$_2$, $C_{1-4}$ alkylamino, and ($C_{1-4}$ alkyl)$_2$-amino;

R$^9$ is independently selected at each occurrence from the group H, $C_{1-4}$ alkyl and $C_{3-8}$ cycloalkyl;

R$^{13}$ is selected from the group $C_{1-4}$ alkyl, $C_{1-2}$ haloalkyl, $C_{1-2}$ alkoxy-$C_{1-2}$ alkyl, $C_{3-6}$ cycloalkyl-$C_{1-2}$ alkyl, aryl ($C_{1-2}$ alkyl)-, and heteroaryl($C_{1-2}$ alkyl)-;

R$^{13a}$ and R$^{16a}$ are independently selected at each occurrence from the group H, $C_{1-4}$ alkyl, $C_{1-4}$ haloalkyl, $C_{1-4}$ alkoxy-$C_{1-4}$ alkyl, $C_{3-6}$ cycloalkyl, and $C_{3-6}$ cycloalkyl-$C_{1-6}$ alkyl;

R$^{14}$ is selected from the group $C_{1-4}$ alkyl, $C_{1-2}$ haloalkyl, $C_{1-2}$ alkoxy-$C_{1-2}$ alkyl, $C_{3-6}$ cycloalkyl-$C_{1-2}$ alkyl, aryl ($C_{1-2}$ alkyl)-, and heteroaryl($C_{1-2}$ alkyl)-;

R$^{14a}$ is selected from the group $C_{1-4}$ alkyl, $C_{1-2}$ haloalkyl, $C_{1-2}$ alkoxy-$C_{1-2}$ alkyl, and $C_{3-6}$ cycloalkyl-$C_{1-2}$ alkyl;

R$^{14b}$ is selected from the group $C_{1-4}$ alkyl, $C_{1-2}$ haloalkyl, $C_{1-2}$ alkoxy-$C_{1-2}$ alkyl, $C_{3-6}$ cycloalkyl, and $C_{3-6}$ cycloalkyl-$C_{1-2}$ alkyl;

R$^{15}$ is independently selected at each occurrence from the group H, $C_{1-4}$ alkyl, $C_{3-7}$ cycloalkyl, $C_{3-6}$ cycloalkyl-$C_{1-6}$ alkyl, phenyl and benzyl, each phenyl or benzyl being substituted on the aryl moiety with 0–3 groups chosen from the group $C_{1-4}$ alkyl, Br, Cl, F, $C_{1-4}$ haloalkyl, $C_{1-4}$ alkoxy, $C_{1-4}$ haloalkoxy, and dimethylamino;

R$^{15a}$ is independently selected at each occurrence from the group H, $C_{1-4}$ alkyl, $C_{3-7}$ cycloalkyl, and $C_{3-6}$ cycloalkyl-$C_{1-6}$ alkyl;

R$^{17}$, R$^{18}$ and R$^{19}$ are independently selected at each occurrence from the group H, $C_{1-6}$ alkyl, $C_{3-10}$ cycloalkyl, $C_{3-6}$ cycloalkyl-$C_{1-6}$ alkyl, $C_{1-2}$ alkoxy-$C_{1-2}$ alkyl, and $C_{1-4}$ haloalkyl;

alternatively, in an NR$^{17}$R$^{19}$ moiety, R$^{17}$ and R$^{19}$ taken together form 1-pyrrolidinyl, 1-morpholinyl, 1-piperidinyl or 1-piperazinyl, wherein N$_4$ in 1-piperazinyl is substituted with 0–1 substituents selected from the group R$^{13}$, CO$_2$R$^{14}$, COR$^{14}$ and SO$_2$R$^{14}$;

R$^{17a}$ and R$^{19a}$ are independently selected at each occurrence from the group H, $C_{1-6}$ alkyl, $C_{3-10}$ cycloalkyl, $C_{3-6}$ cycloalkyl-$C_{1-6}$ alkyl and $C_{1-4}$ haloalkyl;

aryl is phenyl substituted with 1–4 substituents independently selected at each occurrence from the group $C_{1-4}$ alkyl, $C_{3-6}$ cycloalkyl, —OR$^{17}$, Br, Cl, F, $C_{1-4}$ haloalkyl, —CN, —S(O)$_n$R$^{18}$, —COR$^{17}$, —CO$_2$R$^{17}$, —NR$^{15}$COR$^{17}$, —NR$^{15}$CO$_2$R$^{18}$, —NR$^{17}$R$^{19}$, and —CONR$^{17}$R$^{19}$; and, heteroaryl is independently selected at each occurence from the group pyridyl, pyrimidinyl, triazinyl, furanyl, quinolinyl, isoquinolinyl, thienyl, thiazolyl, indolyl, pyrrolyl, oxazolyl, benzofuranyl, benzothienyl, benzothiazolyl, benzoxazolyl, isoxazolyl, tetrazolyl, indazolyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, benzoxazolin-2-on-yl, benzodioxolanyl and benzodioxane, each heteroaryl being substituted 1–4 carbon atoms with a substituent independently selected at each occurrence from the group $C_{1-6}$ alkyl, $C_{3-6}$ cycloalkyl, Br, Cl, F, $C_{1-4}$ haloalkyl, —CN, —OR$^{17}$, —S(O)$_m$R$^{18}$, —COR$^{17}$, —CO$_2$R$^{17}$, —OC(O)R$^{18}$, —NR$^{15}$COR$^{17}$, —N(COR$^{17}$)$_2$, —NR$^{15}$CO$_2$R$^{18}$, —NR$^{17}$R$^{19}$, and —CONR$^{17}$R$^{19}$ and each heteroaryl being substituted on any nitrogen atom with 0–1 substituents selected from the group R$^{15}$, CO$_2$R$^{14a}$, COR$^{14a}$ and SO$_2$R$^{14a}$.

[5s] In another still more preferred embodiment, the present invention provides a novel compound of formula Id, wherein:

X is selected from the group O, S and a bond

R$^1$ is $C_{1-6}$ alkyl;

R$^1$ is substituted with a $C_{3-6}$ cycloalkyl, wherein one carbon atom in the $C_{4-6}$ cycloalkyl is replaced by a group selected from the group —O—, —S(O)$_n$—, and —NR$^{13a}$—;

R$^1$ is also substituted with 0–2 substituents independently selected at each occurrence from the group R$^{1a}$, R$^{1b}$, $C_{1-6}$ alkyl, $C_{2-8}$ alkenyl, $C_{2-8}$ alkynyl, F, CF$_3$, —OR$^{13a}$, —NR$^{13a}$R$^{16a}$, —CH$_2$OCH$_3$, —CH$_2$CH$_2$OCH$_3$, and $C_{3-6}$ cycloalkyl which is substituted with 0–1 CH$_3$ and in which 0–1 carbons of $C_{4-8}$ cycloalkyl is replaced by —O—;

provided that R$^1$ is other than a cyclohexyl-(CH$_2$)$_2$-group;

R$^{1a}$ is aryl and is phenyl substituted with 0–1 substituents selected from OCH$_3$, OCH$_2$CH$_3$, OCH(CH$_3$)$_2$, OCH$_2$CH$_2$CH$_3$, and OCF$_3$, and 0–3 substituents independently selected at each occurrence from the group CH$_3$, CH$_2$CH$_3$, CH(CH$_3$)$_2$, CH$_2$CH$_2$CH$_3$, cyclopropyl, Br, Cl, F, CF$_3$, —CN, SCH$_3$, —NH$_2$, —NHCH$_3$, —N(CH$_3$)$_2$, —C(O)NH$_2$, —C(O)NHCH$_3$, and —C(O)N(CH$_3$)$_2$;

R$^{1b}$ is heteroaryl and is selected from the group furanyl, thienyl, imidazolyl, thiazolyl, oxazolyl, isoxazolyl, pyrazolyl, triazolyl, tetrazolyl, and indazolyl, each heteroaryl being substituted on 0–3 carbon atoms with a substituent independently selected at each occurrence from the group CH$_3$, CH$_2$CH$_3$, CH(CH$_3$)$_2$, CH$_2$CH$_2$CH$_3$, cyclopropyl, OCH$_3$, OCH$_2$CH$_3$, OCH(CH$_3$)$_2$, OCH$_2$CH$_2$CH$_3$, OCF$_3$, Br, Cl, F, CF$_3$, —CN, SCH$_3$, —NH$_2$, —NHCH$_3$, —N(CH$_3$)$_2$, —C(O)NH$_2$, —C(O)NHCH$_3$, and —C(O)N(CH$_3$)$_2$ and each heteroaryl being substituted on any nitrogen atom with 0–1 substituents selected from the group CH$_3$, CO$_2$CH$_3$, COCH$_3$ and SO$_2$CH$_3$;

R$^2$ is selected from the group CH$_3$, CH$_2$CH$_3$, CH(CH$_3$)$_2$, and CH$_2$CH$_2$CH$_3$;

R$^7$ and R$^8$ are independently selected from the group H, CH$_3$, CH$_2$CH$_3$, CH(CH$_3$)$_2$, and CH$_2$CH$_2$CH$_3$;

aryl is phenyl substituted with 2–4 substituents independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, $SO_2CH_3$, —$NH_2$, —$NHCH_3$, —$N(CH_3)_2$, —$C(O)NH_2$, —$C(O)NHCH_3$, and —$C(O)N(CH_3)_2$; and, heteroaryl is independently selected at each occurence from the group pyridyl, indolyl, benzothienyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, and benzoxazolin-2-on-yl, each heteroaryl being substituted on 2–4 carbon atoms with a substituent independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, $SO_2CH_3$, —$NH_2$, —$NHCH_3$, —$N(CH_3)_2$, —$C(O)NH_2$, —$C(O)NHCH_3$, and —$C(O)N(CH_3)_2$ and each heteroaryl being substituted on any nitrogen atom with 0–1 substituents selected from the group $CH_3$, $CO_2CH_3$, $COCH_3$ and $SO_2CH_3$.

[5t] In another further preferred embodiment, the present invention provides a novel compound of formula Id, wherein:

$R^1$ is (cyclopropyl)$C_1$ alkyl or (cyclobutyl)$C_1$ alkyl;

$R^1$ is substituted with 1–2 substituents independently selected at each occurrence from the group $R^{1a}$, $R^{1b}$, $CH_3$, $CH_2CH_3$, $CH(CH_3)_2$, $CH_2CH_2CH_3$, —$(CH_2)_3CH_3$, —CH═$CH_2$, —CH═CH($CH_3$), —CH≡CH, —CH≡C($CH_3$), —$CH_2OCH_3$, —$CH_2CH_2OCH_3$, F, $CF_3$, cyclopropyl, $CH_3$-cyclopropyl, cyclobutyl, $CH_3$-cyclobutyl, cyclopentyl, $CH_3$-cyclopentyl;

$R^{1a}$ is phenyl substituted with 0–1 substituents selected from $OCH_3$, $OCH_2CH_3$, and $OCF_3$, and 0–2 substituents independently selected at each occurrence from the group $CH_3$, $CH_2CH_3$, $CH(CH_3)_2$, $CH_2CH_2CH_3$, Br, Cl, F, $CF_3$, —CN, and $SCH_3$;

$R^{1b}$ is heteroaryl and is selected from the group furanyl, thienyl, imidazolyl, thiazolyl, oxazolyl, isoxazolyl, pyrazolyl, triazolyl, and tetrazolyl, each heteroaryl being substituted on 0–3 carbon atoms with a substituent independently selected at each occurrence from the group $CH_3$, $CH_2CH_3$, $CH(CH_3)_2$, $CH_2CH_2CH_3$, $OCH_3$, $OCH_2CH_3$, $OCF_3$, Br, Cl, F, $CF_3$, —CN, and $SCH_3$ and each heteroaryl being substituted on any nitrogen atom with 0–1 substituents selected from the group $CH_3$, $CO_2CH_3$, $COCH_3$ and $SO_2CH_3$;

$R^2$ is selected from the group $CH_3$, $CH_2CH_3$, and $CH(CH_3)_2$;

$R^7$ and $R^8$ are independently selected from the group H and $CH_3$;

aryl is phenyl substituted with 2–4 substituents independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$. $SO_2CH_3$, —$NH_2$, —$NHCH_3$, —$N(CH_3)_2$, —$C(O)NH_2$, —$C(O)NHCH_3$, and —$C(O)N(CH_3)_2$; and, heteroaryl is pyridyl substituted on 2–4 carbon atoms with a substituent independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, $CF_3$, —CN, $SCH_3$, $SO_2CH_3$, —$NH_2$, —$NHCH_3$, —$N(CH_3)_2$, —$C(O)NH_2$, —$C(O)NHCH_3$, and —$C(O)N(CH_3)_2$.

[5u] In another even further preferred embodiment, the present invention provides a novel compound of formula Id, wherein:

$R^1$ is (cyclopropyl)$C_1$ alkyl or (cyclobutyl)$C_1$ alkyl;

$R^1$ is substituted with 1–2 substituents independently selected at each occurrence from the group $R^{1a}$, $R^{1b}$, $CH_3$, $CH_2CH_3$, $CH(CH_3)_2$, $CH_2CH_2CH_3$, —$(CH_2)_3CH_3$, —CH═$CH_2$, —CH═CH($CH_3$), —CH≡CH, —CH≡C($CH_3$), —$CH_2OCH_3$, —$CH_2CH_2OCH_3$, F, $CF_3$, cyclopropyl, and $CH_3$-cyclopropyl;

$R^{1a}$ is phenyl substituted with 0–2 substituents independently selected at each occurrence from the group $CH_3$, $CH_2CH_3$, $CH(CH_3)_2$, $CH_2CH_2CH_3$, Br, Cl, F, $CF_3$, —CN, and $SCH_3$;

$R^{1b}$ is heteroaryl and is selected from the group furanyl, thienyl, imidazolyl, thiazolyl, oxazolyl, isoxazolyl, and pyrazolyl, each heteroaryl being substituted on 0–3 carbon atoms with a substituent independently selected at each occurrence from the group $CH_3$, $CH_2CH_3$, $CH(CH_3)_2$, $CH_2CH_2CH_3$, $OCH_3$, $OCH_2CH_3$, $OCF_3$, Br, Cl, F, $CF_3$, —CN, and $SCH_3$.

[5v] In another further preferred embodiment, the present invention provides a novel compound of formula Id, wherein:

D is phenyl substituted with 2–4 substituents independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, and $CF_3$.

[5w] In another further preferred embodiment, the present invention provides a novel compound of formula Id, wherein:

D is pyridyl substituted on 2–4 carbon atoms with a substituent independently selected at each occurrence from the group $CH_3$, $CH_2CH_3$, $CH(CH_3)_2$, $CH_2CH_2CH_3$, cyclopropyl, $OCH_3$, $OCH_2CH_3$, $OCH(CH_3)_2$, $OCH_2CH_2CH_3$, $OCF_3$, Br, Cl, F, and $CF_3$.

[6] In a second embodiment, the present invention provides a novel method of treating affective disorder, anxiety, depression, headache, irritable bowel syndrome, post-traumatic stress disorder, supranuclear palsy, immune suppression, Alzheimer's disease, gastrointestinal diseases, anorexia nervosa or other feeding disorder, drug addiction, drug or alcohol withdrawal symptoms, inflammatory diseases, cardiovascular or heart-related diseases, fertility problems, human immunodeficiency virus infections, hemorrhagic stress, obesity, infertility, head and spinal cord traumas, epilepsy, stroke, ulcers, amyotrophic lateral sclerosis, hypoglycemia or a disorder the treatment of which can be effected or facilitated by antagonizing CRF, including but not limited to disorders induced or facilitated by CRF, in mammals, comprising: administering to the mammal a therapeutically effective amount of a compound of formula (I):

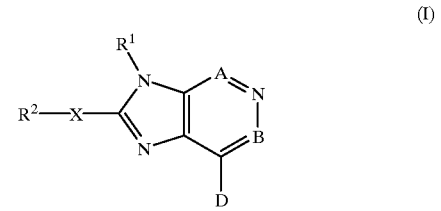

or a stereoisomer or pharmaceutically acceptable salt form thereof, wherein:

A is N or C—$R^7$;

B is N or C—$R^8$;

D is an aryl or heteroaryl group attached through an unsaturated carbon atom;

X is selected from the group CH—$R^9$, N—$R^{10}$, O, S(O)$_n$ and a bond;

n is 0, 1 or 2;

$R^1$ is selected from the group $C_{1-10}$ alkyl, $C_{2-10}$ alkenyl, $C_{2-10}$ alkynyl, $C_{3-8}$ cycloalkyl, $C_{3-6}$ cycloalkyl-$C_{1-6}$ alkyl, $C_{1-4}$ alkoxy-$C_{1-4}$ alkyl, —$SO_2$-$C_{1-10}$ alkyl, —$SO_2$—$R^{1a}$, and —$SO_2$—$R^{1b}$;

$R^1$ is substituted with 0–1 substituents selected from the group —CN, —S(O)$_n R^{14b}$, —$COR^{13a}$, —$CO_2R^{13a}$, —$NR^{15a}COR^{13a}$, —$N(COR^{13a})_2$, —$NR^{15a}CONR^{13a}R^{16a}$, —$NR^{15a}CO_2R^{14b}$, —$CONR^{13a}R^{16a}$, 1-morpholinyl, 1-piperidinyl, 1-piperazinyl, and $C_{3-8}$ cycloalkyl, wherein 0–1 carbon atoms in the $C_{4-8}$ cycloalkyl is replaced by a group selected from the group —O—, —S(O)$_n$—, —$NR^{13a}$—, —$NCO_2R^{14b}$—, —$NCOR^{14b}$— and —$NSO_2R^{14b}$—, and wherein $N_4$ in 1-piperazinyl is substituted with 0–1 substituents selected from the group $R^{13a}$, $CO_2R^{14b}$, $COR^{14b}$ and $SO_2R^{14b}$;

$R^1$ is also substituted with 0–3 substituents independently selected at each occurrence from the group $R^{1a}$, $R^{1b}$, $R^{1c}$, $C_{1-6}$ alkyl, $C_{2-8}$ alkenyl, $C_{2-8}$ alkynyl, Br, Cl, F, I, $C_{1-4}$ haloalkyl, —$OR^{13a}$, —$NR^{13a}R^{16a}$, $C_{1-4}$ alkoxy-$C_{1-4}$ alkyl, and $C_{3-8}$ cycloalkyl which is substituted with 0–1 $R^9$ and in which 0–1 carbons of $C_{4-8}$ cycloalkyl is replaced by —O—;

$R^{1a}$ is aryl and is selected from the group phenyl, naphthyl, indanyl and indenyl, each $R^{1a}$ being substituted with 0–5 substituents independently selected at each occurrence from the group $C_{1-6}$ alkyl, $C_{3-6}$ cycloalkyl, Br, Cl, F, I, $C_{1-4}$ haloalkyl, —CN, nitro, —$OR^{17}$, SH, —$S(O)_n R^{18}$, —$COR^{17}$, —$OC(O)R^{18}$, —$NR^{15a}COR^{17}$, —$N(COR^{17})_2$, —$NR^{15a}CONR^{17a}R^{19a}$, —$NR^{15a}CO_2R^{18}$, —$NR^{17a}R^{19a}$, and —$CONR^{17a}R^{19a}$;

$R^{1b}$ is heteroaryl and is selected from the group pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, pyrazolyl, triazolyl, tetrazolyl, indazolyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, benzoxazolin-2-onyl, benzodioxolanyl and benzodioxane, each heteroaryl being substituted on 0–4 carbon atoms with a substituent independently selected at each occurrence from the group $C_{1-6}$ alkyl, $C_{3-6}$ cycloalkyl, Br, Cl, F, I, $C_{1-4}$ haloalkyl, —CN, nitro, —$OR^{17}$, SH, —$S(O)_m R^{18}$, —$COR^{17}$, —$OC(O)R^{18}$, —$NR^{15a}COR^{17}$, —$N(COR^{17})_2$, —$NR^{15a}CONR^{17a}R^{19a}$, —$NR^{15a}CO_2R^{18}$, —$NR^{17a}R^{19a}$, and —$CONR^{17a}R^{19a}$ and each heteroaryl being substituted on any nitrogen atom with 0–1 substituents selected from the group $R^{15a}$, $CO_2R^{14b}$, $COR^{14b}$ and $SO_2R^{14b}$;

$R^{1c}$ is heterocyclyl and is a saturated or partially saturated heteroaryl, each heterocyclyl being substituted on 0–4 carbon atoms with a substituent independently selected at each occurrence from the group $C_{1-6}$ alkyl, $C_{3-6}$ cycloalkyl, Br, Cl, F, I, $C_{1-4}$ haloalkyl, —CN, nitro, —$OR^{13a}$, SH, —$S(O)_n R^{14b}$, —$COR^{13a}$, —$OC(O)R^{14b}$, —$NR^{15a}COR^{13a}$, —$N(COR^{13a})_2$, —$NR^{15a}CONR^{13a}R^{16a}$, —$NR^{15a}CO_2R^{14b}$, —$NR^{13a}R^{16a}$, and —$CONR^{13a}R^{16a}$ and each heterocyclyl being substituted on any nitrogen atom with 0–1 substituents selected from the group $R^{13a}$, $CO_2R^{14b}$, $COR^{14b}$ and $SO_2R^{14b}$ and wherein any sulfur atom is optionally monooxidized or dioxidized;

$R^2$ is selected from the group $C_{1-4}$ alkyl, $C_{3-8}$ cycloalkyl, $C_{2-4}$ alkenyl, and $C_{2-4}$ alkynyl and is substituted with 0–3 substituents selected from the group —CN, hydroxy, halo and $C_{1-4}$ alkoxy;

alternatively $R^2$, in the case where X is a bond, is selected from the group —CN, $CF_3$ and $C_2F_5$;

$R^7$ and $R^8$ are independently selected at each occurrence from the group H, Br, Cl, F, I, —CN, $C_{1-4}$ alkyl, $C_{3-8}$ cycloalkyl, $C_{1-4}$ alkoxy, $C_{1-4}$ alkylthio, $C_{1-4}$ alkylsulfinyl, $C_{1-4}$ alkylsulfonyl, amino, $C_{1-4}$ alkylamino, ($C_{1-4}$ alkyl)$_2$amino and phenyl, each phenyl is substituted with 0–3 groups selected from the group $C_{1-7}$ alkyl, $C_{3-8}$ cycloalkyl, Br, Cl, F, I, $C_{1-4}$ haloalkyl, nitro, $C_{1-4}$ alkoxy, $C_{1-4}$ haloalkoxy, $C_{1-4}$ alkylthio, $C_{1-4}$ alkyl sulfinyl, $C_{1-4}$ alkylsulfonyl, $C_{1-6}$ alkylamino and ($C_{1-4}$ alkyl)$_2$amino;

$R^9$ and $R^{10}$ are independently selected at each occurrence from the group H, $C_{1-4}$ alkyl, $C_{3-6}$ cycloalkyl-$C_{1-4}$ alkyl and $C_{3-8}$ cycloalkyl;

$R^{13}$ is selected from the group H, $C_{1-4}$ alkyl, $C_{1-4}$ haloalkyl, $C_{1-4}$ alkoxy-$Cl_{-4}$ alkyl, $C_{3-6}$ cycloalkyl, $C_{3-6}$ cycloalkyl-$C_{1-6}$ alkyl, aryl, aryl($C_{1-4}$ alkyl)-, heteroaryl and heteroaryl ($C_{1-4}$ alkyl)-;

$R^{13a}$ and $R^{16a}$ are independently selected at each occurrence from the group H, $C_{1-4}$ alkyl, $C_{1-4}$ haloalkyl, $C_{1-4}$ alkoxy-$C_{1-4}$ alkyl, $C_{3-6}$ cycloalkyl, and $C_{3-6}$ cycloalkyl-$C_{1-6}$ alkyl;

$R^{14}$ is selected from the group $C_{1-4}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl, aryl, aryl($C_{1-4}$ alkyl)-, heteroaryl and heteroaryl($C_{1-4}$ alkyl)- and benzyl, each benzyl being substituted on the aryl moiety with 0–1 substituents selected from the group $C_{1-4}$ alkyl, Br, Cl, F, I, $C_{1-4}$ haloalkyl, nitro, $C_{1-4}$ alkoxy $C_{1-4}$ haloalkoxy, and dimethylamino;

$R^{14a}$ is selected from the group $C_{1-4}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl and benzyl, each benzyl being substituted on the aryl moiety with 0–1 substituents selected from the group $C_{1-4}$ alkyl, Br, Cl, F, I, $C_{1-4}$ haloalkyl, nitro, $C_{1-4}$ alkoxy, $C_{1-4}$ haloalkoxy, and dimethylamino;

$R^{14b}$ is selected from the group $C_{1-4}$ alkyl, $C_{1-4}$ haloalkyl, $C_{1-4}$ alkoxy-$C_{1-4}$ alkyl, $C_{3-6}$ cycloalkyl, and $C_{3-6}$ cycloalkyl-$C_{1-6}$ alkyl;

$R^{15}$ is independently selected at each occurrence from the group H, $C_{1-4}$ alkyl, $C_{3-7}$ cycloalkyl, $C_{3-6}$ cycloalkyl-$C_{1-6}$ alkyl, phenyl and benzyl, each phenyl or benzyl being substituted on the aryl moiety with 0–3 groups chosen from the group $C_{1-4}$ alkyl, Br, Cl, F, I, $C_{1-4}$ haloalkyl, nitro, $C_{1-4}$ alkoxy, $C_{1-4}$ haloalkoxy, and dimethylamino;

$R^{15a}$ is independently selected at each occurrence from the group H, $C_{1-4}$ alkyl, $C_{3-7}$ cycloalkyl, and $C_{3-6}$ cycloalkyl-$C_{1-6}$ alkyl;

R¹⁷ is selected at each occurrence from the group H, $C_{1-6}$ alkyl, $C_{3-10}$ cycloalkyl, $C_{3-6}$ cycloalkyl-$C_{1-6}$ alkyl, $C_{1-2}$ alkoxy-$C_{1-2}$ alkyl, $C_{1-4}$ haloalkyl, $R^{14}S(O)_n$—$C_{1-4}$ alkyl, and $R^{17b}R^{19b}N^{13}C_{2-4}$ alkyl;

R¹⁸ and R¹⁹ are independently selected at each occurrence from the group H, $C_{1-6}$ alkyl, $C_{3-10}$ cycloalkyl, $C_{3-6}$ cycloalkyl-$C_{1-6}$ alkyl, $C_{1-2}$ alkoxy-$C_{1-2}$ alkyl, and $C_{1-4}$ haloalkyl;

alternatively, in an NR¹⁷R¹⁹ moiety, R¹⁷ and R¹⁹ taken together form 1-pyrrolidinyl, 1-morpholinyl, 1-piperidinyl or 1-piperazinyl, wherein N₄ in 1-piperazinyl is substituted with 0–1 substituents selected from the group R $CO_2R^{14}$, $COR^{14}$ and $SO_2R^{14}$;

alternatively, in an NR¹⁷ᵇR¹⁹ᵇ moiety, R¹⁷ᵇ and R¹⁹ᵇ taken together form 1-pyrrolidinyl, 1-morpholinyl, 1-piperidinyl or 1-piperazinyl, wherein N₄ in 1-piperazinyl is substituted with 0–1 substituents selected from the group R¹³, $CO_2R^{14}$, $COR^{14}$ and $SO_2R^{14}$;

R¹⁷ᵃ and R¹⁹ᵃ are independently selected at each occurrence from the group H, $C_{1-6}$ alkyl, $C_{3-10}$ cycloalkyl, $C_{3-6}$ cycloalkyl-$C_{1-6}$ alkyl and $C_{1-4}$ haloalkyl;

aryl is independently selected at each occurrence from the group phenyl, naphthyl, indanyl and indenyl, each aryl being substituted with 0–5 substituents independently selected at each occurrence from the group $C_{1-6}$ alkyl, $C_{3-6}$ cycloalkyl, methylenedioxy, $C_{1-4}$ alkoxy-$C_{1-4}$ alkoxy, —OR¹⁷, Br, Cl, F, I, $C_{1-4}$ haloalkyl, —CN, —NO₂, SH, —S(O)ₙR¹⁸, —COR¹⁷, —CO₂R¹⁷, —OC(O)R¹⁸, —NR¹⁵COR¹⁷, —N(COR¹⁷)₂, —NR¹⁵CONR¹⁷R¹⁹, —NR¹⁵CO₂R¹⁸, —NR¹⁷R¹⁹, and —CONR¹⁷R¹⁹ and up to 1 phenyl, each phenyl substituent being substituted with 0–4 substituents selected from the group $C_{1-3}$ alkyl, $C_{1-3}$ alkoxy, Br, Cl, F, I, —CN, dimethylamino, CF₃, C₂F₅, OCF₃, SO₂Me and acetyl; and, heteroaryl is independently selected at each occurence from the group pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, triazolyl, tetrazolyl, indazolyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, benzoxazolin-2-on-yl, benzodioxolanyl and benzodioxane, each heteroaryl being substituted 0–4 carbon atoms with a substituent independently selected at each occurrence from the group $C_{1-6}$ alkyl, $C_{3-6}$ cycloalkyl, Br, Cl, F, I, $C_{1-4}$ haloalkyl, —CN, nitro, —OR¹⁷, SH, —S(O)ₙR¹⁸, —COR¹⁷, —CO₂R¹⁷, —OC(O)R¹⁸, —NR¹⁵COR¹⁷, —N(COR¹⁷)₂, —NR¹⁵CONR¹⁷R¹⁹, —NR¹⁵CO₂R¹⁸, —NR¹⁷R¹⁹, and —CONR¹⁷R¹⁹ and each heteroaryl being substituted on any nitrogen atom with 0–1 substituents selected from the group R¹⁵, $CO_2R^{14a}$, $COR^{14a}$ and $SO_2R^{14a}$.

[7] In a third embodiment, the present invention provides a novel pharmaceutical composition, comprising: a pharmaceutically acceptable carrier and a therapeutically effective amount of a compound of formula (I):

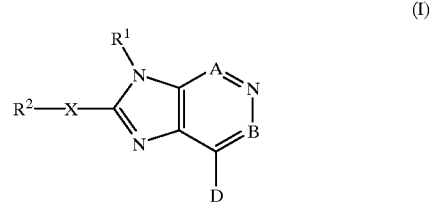

or a stereoisomer or pharmaceutically acceptable salt form thereof, wherein:

A is N or C—R⁷;

B is N or C—R⁸;

D is an aryl or heteroaryl group attached through an unsaturated carbon atom;

X is selected from the group CH—R⁹, N—R¹⁰, O, S(O)ₙ and a bond;

n is 0, 1 or 2;

R¹ is selected from the group $C_{1-10}$ alkyl, $C_{2-10}$ alkenyl, $C_{2-10}$ alkynyl, $C_{3-8}$ cycloalkyl, $C_{3-6}$ cycloalkyl-$C_{1-6}$ alkyl, $C_{1-4}$ alkoxy-$C_{1-4}$ alkyl, —SO₂-$C_{1-10}$ alkyl, —SO₂—R¹ᵃ, and —SO₂—R¹ᵇ;

R¹ is substituted with 0–1 substituents selected from the group —CN, —S(O)ₙR¹⁴ᵇ, —COR¹³ᵃ, —CO₂R¹³ᵃ, —NR¹⁵ᵃCOR¹³ᵃ, —N(COR¹³ᵃ)₂, —NR¹⁵ᵃCONR¹³ᵃR¹⁶ᵃ, —NR¹⁵ᵃCO₂R¹⁴ᵇ, —CONR¹³ᵃR¹⁶ᵃ, 1-morpholinyl, 1-piperidinyl, 1-piperazinyl, and $C_{3-8}$ cycloalkyl, wherein 0–1 carbon atoms in the $C_{4-8}$ cycloalkyl is replaced by a group selected from the group —O—, —S(O)ₙ—, NR¹³ᵃ—, —NCO₂R¹⁴ᵇ—, —NCOR¹⁴ᵇ— and —NSO₂R¹⁴ᵇ—, and wherein N₄ in 1-piperazinyl is substituted with 0–1 substituents selected from the group R¹³ᵃ, CO₂R¹⁴ᵇ, COR¹⁴ᵇ and SO₂R¹⁴ᵇ;

R¹ is also substituted with 0–3 substituents independently selected at each occurrence from the group R¹ᵃ, R¹ᵇ, R¹ᶜ, $C_{1-6}$ alkyl, $C_{2-8}$ alkenyl, $C_{2-8}$ alkynyl, Br, Cl, F, I, $C_{1-4}$ haloalkyl, —OR¹³ᵃ, —NR¹³ᵃR¹⁶ᵃ, $C_{1-4}$ alkoxy-$C_{1-4}$ alkyl, and $C_{3-8}$ cycloalkyl which is substituted with 0–1 R⁹ and in which 0–1 carbons of $C_{4-8}$ cycloalkyl is replaced by —O—;

R¹ᵃ is aryl and is selected from the group phenyl, naphthyl, indanyl and indenyl, each R¹ᵃ being substituted with 0–5 substituents independently selected at each occurrence from the group $C_{1-6}$ alkyl, $C_{3-6}$ cycloalkyl, Br, Cl, F, I, $C_{1-4}$ haloalkyl, —CN, nitro, —OR¹⁷, SH, —S(O)ₙR¹⁸, —COR¹⁷, —OC(O)R¹⁸, —NR¹⁵ᵃCOR¹⁷, —N(COR¹⁷)₂, —NR¹⁵ᵃCONR¹⁷ᵃR¹⁹ᵃ, —NR¹⁵ᵃCO₂R¹⁸, —NR¹⁷ᵃR¹⁹ᵃ, and —CONR¹⁷ᵃR¹⁹ᵃ;

R¹ᵇ is heteroaryl and is selected from the group pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, pyrazolyl, triazolyl, tetrazolyl, indazolyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, benzoxazolin-2-onyl, benzodioxolanyl and benzodioxane, each heteroaryl being substituted on 0–4 carbon atoms with a substituent independently selected at each occurrence from the group $C_{1-6}$ alkyl, $C_{3-6}$ cycloalkyl, Br, Cl, F. I, $C_{1-4}$ haloalkyl, —CN, nitro, —$OR^{17}$, SH, —$S(O)_mR^{18}$, —$COR^{17}$, —$OC(O)R^{18}$, -$NR^{15a}COR^{17}$, —$N(COR^{17})_2$, —$NR^{15a}CONR^{17a}R^{19a}$, —$NR^{15a}CO_2R^{18}$, —$NR^{17a}R^{19a}$, and —$CONR^{17a}R^{19a}$ and each heteroaryl being substituted on any nitrogen atom with 0–1 substituents selected from the group $R^{15a}$, $CO_2R^{14b}$, $COR^{14b}$ and $SO_2R^{14b}$;

$R^{1c}$ is heterocyclyl and is a saturated or partially saturated heteroaryl, each heterocyclyl being substituted on 0–4 carbon atoms with a substituent independently selected at each occurrence from the group $C_{1-6}$ alkyl, $C_{3-6}$ cycloalkyl, Br, Cl, F, I, $C_{1-4}$ haloalkyl, —CN, nitro, —$OR^{13a}$, SH, —$S(O)_nR^{14b}$, —$COR^{13a}$, —$OC(O)R^{14b}$, —$NR^{15a}COR^{13a}$, —$N(COR^{13a})_2$, —$NR^{15a}CONR^{13a}R^{16a}$, —$NR^{15a}CO_2R^{14b}$, —$NR^{13a}R^{16a}$, and —$CONR^{13a}R^{16a}$ and each heterocyclyl being substituted on any nitrogen atom with 0–1 substituents selected from the group $R^{13a}$, $CO_2R^{14b}$, $COR^{14b}$ and $SO_2R^{14b}$ and wherein any sulfur atom is optionally monooxidized or dioxidized;

$R^2$ is selected from the group $C_{1-4}$ alkyl, $C_{3-8}$ cycloalkyl, $C_{2-4}$ alkenyl, and $C_{2-4}$ alkynyl and is substituted with 0–3 substituents selected from the group —CN, hydroxy, halo and $C_{1-4}$ alkoxy;

alternatively $R^2$, in the case where X is a bond, is selected from the group —CN, $CF_3$ and $C_2F_5$;

$R^7$ and $R^8$ are independently selected at each occurrence from the group H, Br, Cl, F, I, —CN, $C_{1-4}$ alkyl, $C_{3-8}$ cycloalkyl, $C_{1-4}$ alkoxy, $C_{1-4}$ alkylthio, $C_{1-4}$ alkylsulfinyl, $C_{1-4}$ alkylsulfonyl, amino, $C_{1-4}$ alkylamino, ($C_{1-4}$ alkyl)$_2$amino and phenyl, each phenyl is substituted with 0–3 groups selected from the group $C_{1-7}$ alkyl, $C_{3-8}$ cycloalkyl, Br, Cl, F, I, $C_{1-4}$ haloalkyl, nitro, $C_{1-4}$ alkoxy, $C_{1-4}$ haloalkoxy, $C_{1-4}$ alkylthio, $C_{1-4}$ alkyl sulfinyl, $C_{1-4}$ alkylsulfonyl, $C_{1-6}$ alkylamino and ($C_{1-4}$ alkyl)$_2$amino;

$R^9$ and $R^{10}$ are independently selected at each occurrence from the group H, $C_{1-4}$ alkyl, $C_{3-6}$ cycloalkyl-$C_{1-4}$ alkyl and $C_{3-8}$ cycloalkyl;

$R^{13}$ is selected from the group H, $C_{1-4}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl, aryl, aryl ($C_{1-4}$ alkyl)-, heteroaryl and heteroaryl ($C_{1-4}$ alkyl)-;

$R^{13a}$ and $R^{16a}$ are independently selected at each occurrence from the group H, $C_{1-4}$ alkyl, $C_{1-4}$ haloalkyl, $C_{1-4}$ alkoxy-$C_{1-4}$ alkyl, $C_{3-6}$ cycloalkyl, and $C_{3-6}$ cycloalkyl-$C_{1-6}$ alkyl;

$R^{14}$ is selected from the group $C_{1-4}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl, aryl, aryl($C_{1-4}$ alkyl)-, heteroaryl and heteroaryl($C_{1-4}$ alkyl)- and benzyl, each benzyl being substituted on the aryl moiety with 0–1 substituents selected from the group $C_{1-4}$ alkyl, Br, Cl, F, I, $C_{1-4}$ haloalkyl, nitro, $C_{1-4}$ alkoxy $C_{1-4}$ haloalkoxy, and dimethylamino;

$R^{14a}$ is selected from the group $C_{1-4}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl and benzyl, each benzyl being substituted on the aryl moiety with 0–1 substituents selected from the group $C_{1-4}$ alkyl, Br, Cl, F, I, $C_{1-4}$ haloalkyl, nitro, $C_{1-4}$ alkoxy, $C_{1-4}$ haloalkoxy, and dimethylamino;

$R^{14b}$ is selected from the group $C_{1-4}$ alkyl, $C_{1-4}$ haloalkyl, $C_{1-4}$ alkoxy-$C_{1-4}$ alkyl, $C_{3-6}$ cycloalkyl, and $C_{3-6}$ cycloalkyl-$C_{1-6}$ alkyl; $R^{15}$ is independently selected at each occurrence from the group H, $C_{1-4}$ alkyl, $C_{3-7}$ cycloalkyl, $C_{3-6}$ cycloalkyl-$C_{1-6}$ alkyl, phenyl and benzyl, each phenyl or benzyl being substituted on the aryl moiety with 0–3 groups chosen from the group $C_{1-4}$ alkyl, Br, Cl, F, I, $C_{1-4}$ haloalkyl, nitro, $C_{1-4}$ alkoxy, $C_{1-4}$ haloalkoxy, and dimethylamino;

$R^{15a}$, is independently selected at each occurrence from the group H, $C_{1-4}$ alkyl, $C_{3-7}$ cycloalkyl, and $C_{3-6}$ cycloalkyl-$C_{1-6}$ alkyl;

$R^{17}$ is selected at each occurrence from the group H, $C_{1-6}$ alkyl, $C_{3-10}$ cycloalkyl, $C_{3-6}$ cycloalkyl-$C_{1-6}$ alkyl, $C_{1-2}$ alkoxy-$C_{1-2}$ alkyl, $C_{1-4}$ haloalkyl, $R^{14}S(O)_n$—$C_{1-4}$ alkyl, and $R^{17b}R^{19b}N$—$C_{2-4}$ alkyl;

$R^{18}$ and $R^{19}$ are independently selected at each occurrence from the group H, $C_{1-6}$ alkyl, $C_{3-10}$ cycloalkyl, $C_{3-6}$ cycloalkyl-$C_{1-6}$ alkyl, $C_{1-2}$ alkoxy-$C_{1-2}$ alkyl, and $C_{1-4}$ haloalkyl;

alternatively, in an $NR^{17}R^{19}$ moiety, $R^{17}$ and $R^{19}$ taken together form 1-pyrrolidinyl, 1-morpholinyl, 1-piperidinyl or 1-piperazinyl, wherein $N_4$ in 1-piperazinyl is substituted with 0–1 substituents selected from the group $R^{13}$, $CO_2R^{14}$, $COR^{14}$ and $SO_2R^{14}$;

alternatively, in an $NR^{17b}R^{19b}$ moiety $R^{17b}$ and $R^{19b}$ taken together form 1-pyrrolidinyl, 1-morpholinyl, 1-piperidinyl or 1-piperazinyl, wherein $N_4$ in 1-piperazinyl is substituted with 0–1 substituents selected from the group $R^{13}$, $CO_2R^{14}$, $COR^{14}$ and $SO_2R^{14}$;

$R^{17a}$ and $R^{19a}$ are independently selected at each occurrence from the group H, $C_{1-6}$ alkyl, $C_{3-10}$ cycloalkyl, $C_{3-6}$ cycloalkyl-$C_{1-6}$ alkyl and $C_{1-4}$ haloalkyl;

aryl is independently selected at each occurrence from the group phenyl, naphthyl, indanyl and indenyl, each aryl being substituted with 0–5 substituents independently selected at each occurrence from the group $C_{1-6}$ alkyl, $C_{3-6}$ cycloalkyl, methylenedioxy, $C_{1-4}$ alkoxy-$C_{1-4}$ alkoxy, —$OR^{17}$, Br, Cl, F, I, $C_{1-4}$ haloalkyl, —CN, —$NO_2$, SH, —$S(O)_nR^{18}$, —$COR^{17}$, —$CO_2R^{17}$, —$OC(O)R^{18}$, —$NR^{15}COR^{17}$, —$N(COR^{17})_2$, —$NR^{15}CONR^{17}R^{19}$, —$NR^{15}CO_2R^{18}$, —$NR^{17}R^{19}$, and —$CONR^{17}R^{19}$ and up to 1 phenyl, each phenyl substituent being substituted with 0–4 substituents selected from the group $C_{1-3}$ alkyl, $C_{1-3}$ alkoxy, Br, Cl, F, I, —CN, dimethylamino, $CF_3$, $C_2F_5$, $OCF_3$, $SO_2Me$ and acetyl; and, heteroaryl is independently selected at each occurence from the group pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, triazolyl, tetrazolyl, indazolyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, benzoxazolin-2-on-yl, benzodioxolanyl and benzodioxane, each heteroaryl being substituted 0–4 carbon atoms with a substituent independently selected at each occurrence from the group $C_{1-6}$ alkyl, $C_{3-6}$ cycloalkyl, Br, Cl, F, I, $C_{1-4}$ haloalkyl, —CN, nitro, —$OR^{17}$, SH, —$S(O)_mR^{18}$, —$COR^{17}$, —$CO_2R^{17}$, —$OC(O)R^{18}$, —$NR^{15}COR^{17}$, —$N(COR^{17})_2$, —$NR^{15}CONR^{17}R^{19}$, —$NR^{15}CO_2R^{18}$, —$NR^{17}R^{19}$, and —$CONR^{17}R^{19}$ and each heteroaryl being substituted on any nitrogen atom with 0–1 substituents selected from the group $R^{15}$, $CO_2R^{14a}$, $COR^{14a}$ and $SO_2R^{14a}$.

In another preferred embodiment, $R^1$ is other than a cyclohexyl-$(CH_2)_{1, 2, 3, 4, 5, 6, 7, 8, 9,\text{ or }10}$- group.

In another preferred embodiment, $R^1$ is other than an aryl-$(CH_2)_{1, 2, 3, 4, 5, 6, 7, 8, 9,\text{ or }10}$- group, wherein the aryl group is substituted or unsubstituted.

In another preferred embodiment, $R^1$ is other than a heteroaryl-$(CH_2)_{1, 2, 3, 4, 5, 6, 7, 8, 9, \text{ or } 10}$- group, wherein the heteroaryl group is substituted or unsubstituted.

In another preferred embodiment, $R^1$ is other than a heterocyclyl-$(CH_2)_{1, 2, 3, 4, 5, 6, 7, 8, 9, \text{ or } 10}$- group, wherein the heterocyclyl group is substituted or unsubstituted.

In another preferred embodiment, when D is imidazole or triazole, $R^1$ is other than unsubstituted $C_{1, 2, 3, 4, 5, 6, 7, 8, 9, \text{ or } 10}$ linear or branched alkyl or $C_{3, 4, 5, 6, 7, \text{ or } 8}$ cycloalkyl.

In another preferred embodiment, $R^{1a}$ is not substituted with $OR^{17}$.

In fourth embodiment, the present invention provides intermediate compounds useful in preparation of the CRF antagonist compounds and processes for making those intermediates, as described in the following description and claims.

In a fifth embodiment, the present invention provides CRF antagonist compounds and labelled derivatives thereof as standards and reagents in determining the ability of a potential pharmaceutical to bind to the CRF receptor.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

The term "substituted," as used herein, means that any one or more hydrogens on the designated atom is replaced with a selection from the indicated group, provided that the designated atom's normal valency is not exceeded, and that the substitution results in a stable compound. When a substitent is keto (i.e., =O), then 2 hydrogens on the atom are replaced. Keto substituents are not present on aromatic moieties.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^6$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups having the specified number of carbon atoms. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. Alkenyl" is intended to include hydrocarbon chains of either a straight or branched configuration and one or more unsaturated carbon-carbon bonds which may occur in any stable point along the chain, such as ethenyl and propenyl. "Alkynyl" is intended to include hydrocarbon chains of either a straight or branched configuration and one or more triple carbon-carbon bonds which may occur in any stable point along the chain, such as ethynyl and propynyl.

"Halo" or "halogen" as used herein refers to fluoro, chloro, bromo, and iodo; and "counter-ion" is used to represent a small, negatively charged species such as chloride, bromide, hydroxide, acetate, sulfate, and the like.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" or "carbocyclic residue" is intended to mean any stable 3- to 7-membered monocyclic or bicyclic or 7-to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2] bicyclooctane, fluorenyl, phenyl, naphthyl, indanyl, adamantyl, and tetrahydronaphthyl.

As used herein, the term "heterocycle" or "heterocyclic system" is intended to mean a stable 5- to 7-membered monocyclic or bicyclic or 7- to 10-membered bicyclic heterocyclic ring which is saturated partially unsaturated or unsaturated (aromatic), and which consists of carbon atoms and from 1 to 4 heteroatois independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" is intended to mean a stable 5- to 7-membered monocyclic or bicyclic or 7- to 10-membered bicyclic heterocyclic aromatic ring which consists of carbon atoms and from 1 to 4 heterotams independently selected from the group consisting of N, O and S. It is preferred that the total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H, 6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2, 3-triazolyl, 1,2,4-triazolyl, 1,2,5-triazolyl, 1,3,4-triazolyl, and xanthenyl. Preferred heterocycles include, but are not limited to, pyridinyl, furanyl, thienyl, pyrrolyl, pyrazolyl, pyrrolidinyl, imidazolyl, indolyl, benzimidazolyl, 1H-indazolyl, oxazolidinyl, benzotriazolyl, benzisoxazolyl, oxindolyl, benzoxazolinyl, and isatinoyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

"Prodrugs" are intended to include any covalently bonded carriers which release the active parent drug according to formula (I) in vivo when such prodrug is administered to a mammalian subject. Prodrugs of a compound of formula (I) are prepared by modifying functional groups present in the compound in such a way that the modifications are cleaved, either in routine manipulation or in vivo, to the parent compound. Prodrugs include compounds of formula (I) wherein a hydroxy, amino, or sulfhydryl group is bonded to any group that, when the prodrug or compound of formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of formula (I), and the like.

"Stable compound" and "stable structure" are meant to indicate a compound that is sufficiently robust to survive isolation to a useful degree of purity from a reaction mixture, and formulation into an efficacious therapeutic agent.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

"Therapeutically effective amount" is intended to include an amount of a compound of the present invention or an amount of the combination of compounds claimed effective to inhibit HIV infection or treat the symptoms of HIV infection in a host. The combination of compounds is preferably a synergistic combination. Synergy, as described for example by Chou and Talalay, Adv. Enzyme Regul. 22:27–55 (1984), occurs when the effect (in this case, inhibition of HIV replication) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased antiviral effect, or some other beneficial effect of the combination compared with the individual components.

Combinations of substituents and/or variables are permissible only if such combinations result in stable compounds.

A stable compound or stable structure is meant to imply a compound that is sufficiently robust to survive isolation to a useful degree of purity from a reaction mixture, and formulation into an effective therapeutic agent.

The term "therapeutically effective amount" of a compound of this invention means an amount effective to antagonize abnormal level of CRF or treat the symptoms of affective disorder, anxiety or depression in a host.

SYNTHESIS

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include but are not limited to those methods described below. Each of the references cited below are hereby incorporated herein by reference.

The following abbreviations are used herein:

| | |
|---|---|
| AcOH | acetic acid |
| t-BuOK | potassium tert-butoxide |
| DEAD | diethyl azodicarboxylate |
| DMSO | dimethyl sulfoxide |
| EtOAc | ethyl acetate |
| EtOH | ethanol |
| NaHMDS | sodium bis (trimethylsilyl) amide |
| PPh$_3$ | triphenylphosphine |
| THF | tetrahydrofuran |
| TLC | thin layer chromatography |

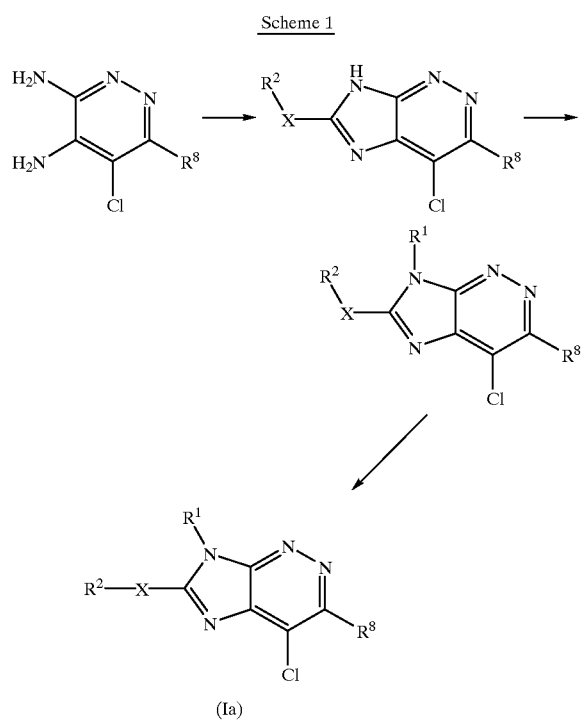

The compounds of this invention of formula (Ia) may be prepared using the methods shown in Scheme 1. In this procedure the 5-chloro-3,4-diaminopyridazine precursor may be cyclized to the desired imidazopyridiazines using orthoesters (for $R^2$—X—=H, alkyl, alkoxy, etc.), orthocarbonates, carboxylic acids, carboxylic acid esters, alkyl imidates and other reagents appropriate to the product desired, and reaction conditions known to those skilled in the art of organic synthesis. The synthesis of the starting material where $R^8$=H, and the chemistry thereof has been described by Kurashi and Castle (J. Het. Chem. 1964, 1, 42).

The imidazolepyridazine may then be N-alkylated using, for example, base promoted conditions (e.g., NaHMDS/ $R^1$—LG, where LG=halide, sulfonate, or other appropriate leaving group) or Mitsunobu reaction conditions (e.g., DEAD/PPh$_3$/$R^1$—OH). The compounds of formula (Ia) are then formed by cross coupling with an appropriate arylboronic acid, arylstannane, or arylzinc reagent under known conditions. In the case where $R^1$ is a protecting group such as benzyl, p-methoxybenzyl, or tetrahydropyranyl (J. Het. Chem. 1968, 5, 13), the group may be removed and N-alkylation at this point gives compounds of formula (Ia).

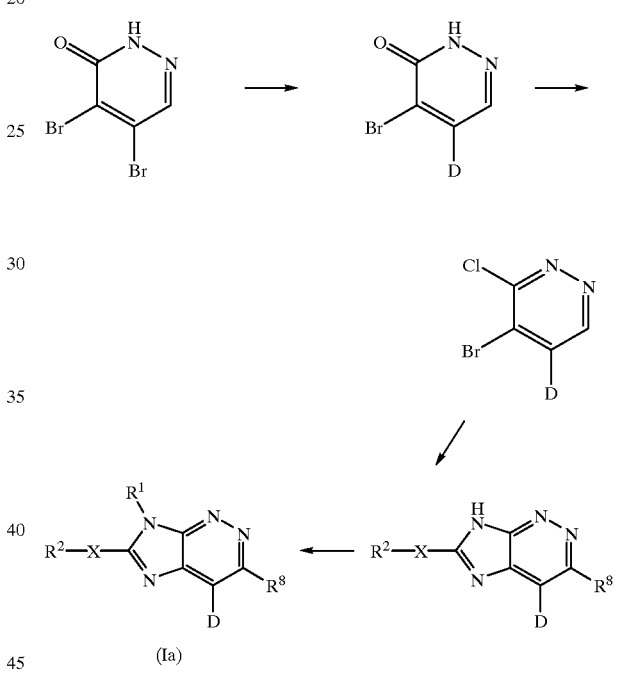

Compounds of formula (Ia) may also be prepared via the method outlined in Scheme 2. Commercially available 4,5-dibromo-pyridazin-3-one is N and/or O benzylated then cross coupled in, for example, a Suzuki reaction (D-B(OH)$_2$/Pd(PPh$_3$)$_4$/Na$_2$CO$_3$) followed by deprotection. Chlorination using, for example, POC$_{13}$ gives a chloro-pyridazine which may then be reacted for example, with an amidine. N-alkylation of the resulting bicyclic compound using the methods described above affords the desired compounds of formula (Ia).

Compounds of formula (Ia) may also be prepared via the method outlined in Scheme 2b. In this procedure, a 2-chloroacetophenone is condensed with a dialkyl malonate (e.g., TiCl$_4$/CCl$_4$/pyridine/THF) or nitroacetate. The product from this reaction is treated with hydrazine to give an intermediate which is oxidized using, for example, DDQ or NBS to give the pyridazinone intermediate. Chlorination (or bromination) using POCl$_3$ (or POBr3) affords a chloro- (or bromo-) pyridazine intermediate.

This intermediate, where Y=ester in Scheme 2b, may now be converted to the acid (e.g., LiOH/H$_2$O/MeOH/THF) and then subjected to conditions such as the Curtius reaction or modifications thereof (e.g., DPPA, Et$_3$N, t-BuOH; TFA/CH$_2$Cl$_2$), which transform the acid to an amino group. Substitution of the halide with an appropriate amine using, for example, nucleophilic substitution or cross-coupling reactions, affords an intermediate which can then be converted to the desired imidazopyridiazines (Ia) by cyclization using orthoesters (for R$^2$—X—=H, alkyl, alkoxy, etc.), orthocarbonates, carboxylic acids, carboxylic acid esters, alkyl imidates and other reagents appropriate to the product desired, and reaction conditions known to those skilled in the art of organic synthesis.

The intermediate where Y=NO$_2$ in Scheme 2b may be treated with an appropriate amine using, for example, nucleophilic substitution conditions. Reduction of the nitro group to the amine (e.g., Fe/AcOH or sodium dithionite/water/EtOH) affords an intermediate which can then be converted to the desired imidazopyridiazines (Ia) by cyclization using orthoesters (for R$^2$—X—=H, alkyl, alkoxy, etc.), orthocarbonates, carboxylic acids, carboxylic acid esters, alkyl imidates and other reagents appropriate to the product desired, and reaction conditions known to those skilled in the art of organic synthesis.

Scheme 2b

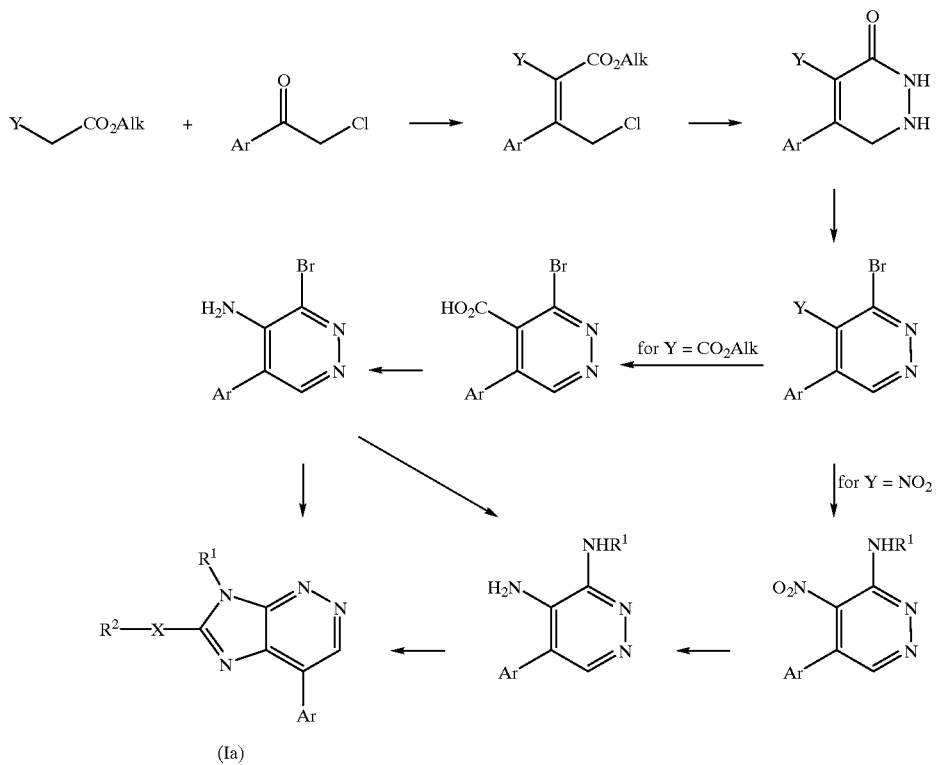

Scheme 3

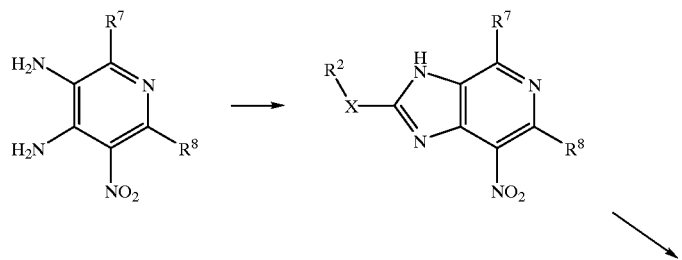

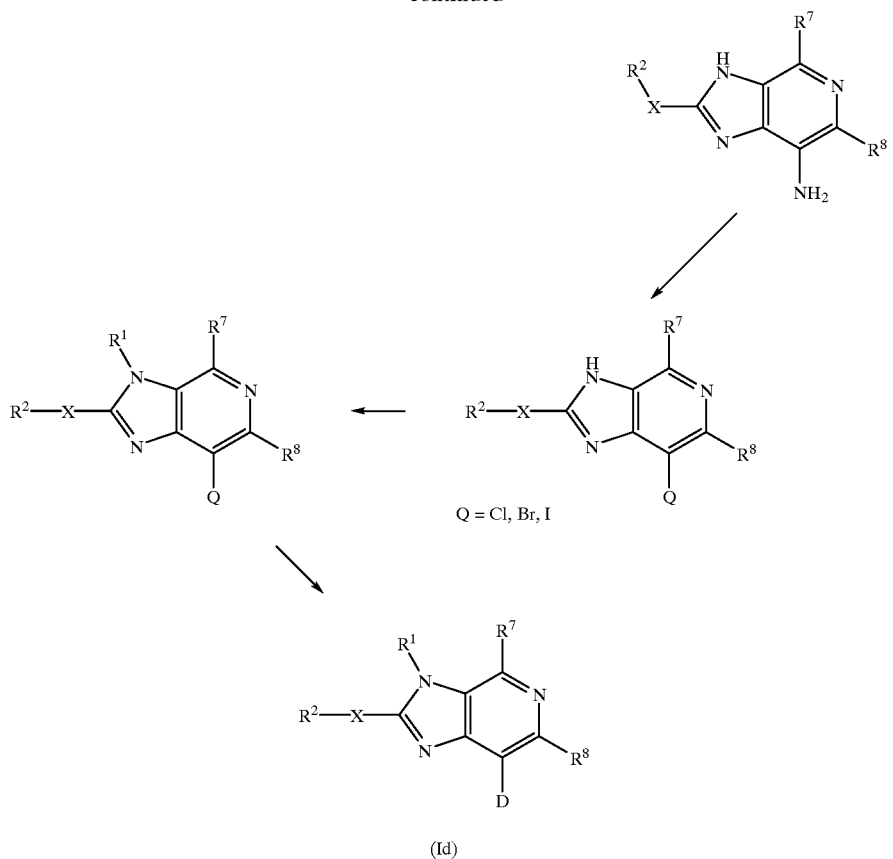

(Id)

The compounds of this invention of formula (Id) may be prepared using the methods shown in Scheme 3. In this procedure, the 3,4-diamino-5-nitropyridine precursor may be cyclized to the desired imidazopyridines using orthoesters (for $R^2$—X—=H, alkyl, alkoxy, etc.), orthocarbonates, carboxylic acids, carboxylic acid esters, alkyl imidates and other reagents appropriate to the product desired, and reaction conditions known to those skilled in the art of organic synthesis. The synthesis of the precursor where $R^7$ and $R^8$=H, and the chemistry thereof has been described by Graboyes and Day (*J. Am. Chem. Soc.* 195779, 6421). Reduction of the nitro group using, for example, stannous chloride, provides the amino compound. Conversion of the amino group to a chloride, bromide or iodide may now be effected via diazotization of the amine followed by displacement with halogen anion. The halide compounds may then be N-alkylated using, for example, base promoted conditions (e.g., NaHMDS/$R^1$—LG, where LG=halide, sulfonate, or other appropriate leaving group) or Mitsunobu reaction conditions (e.g., DEAD/PPh$_3$/$R^1$—OH). Cross coupling with an appropriate arylboronic acid, arylstannane, or arylzinc reagent under known conditions to yield compounds of formula (Id). In the case where $R^1$ is a protecting group, the group may now be removed and N-alkylation at this point gives compounds of formula (Id).

Scheme 4

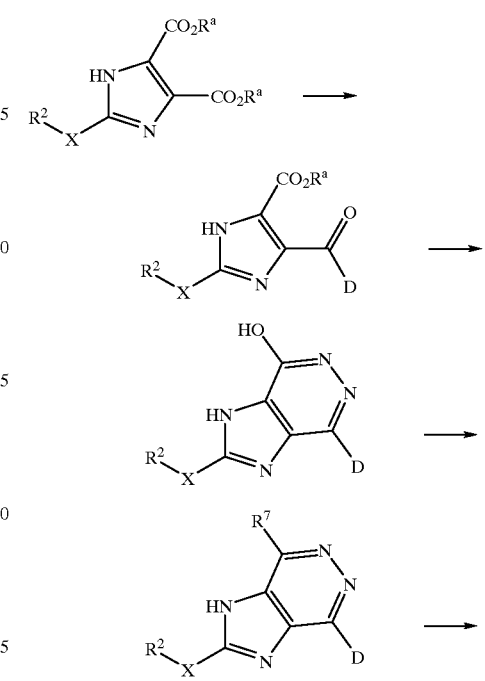

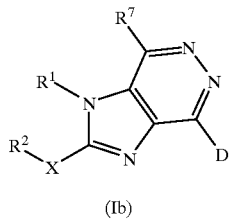

(Ib)

Compounds of Formula (Ib) may be prepared, using the procedures outlined in Scheme 4. The starting material (where Ra is lower alkyl, X and R2 are defined above) may be treated with a compound of the formula D—M (where M=Li, Na, MgBr, MgCl, ZnCl, $CeCl_2$ and D is defined above) in the presence of an inert solvent at reaction temperatures ranging from −80° C. to 250° C. to provide the keto-imidazole. Inert solvents may include, but are not limited to, dialkyl ethers (preferably diethyl ether), cyclic ethers (preferably tetrahydrofuran or 1,4-dioxane) or aromatic hydrocarbons (preferably benzene or toluene).

The imidazolepyridazine can then be formed by reaction with hydrazine in an inert solvent. Inert solvents may include, but are not limited to, alkyl alcohols (1 to 6 carbons), dialkyl ethers (preferably diethyl ether), cyclic ethers (preferably tetrahydrofuran or 1,4-dioxane), aromatic hydrocarbons (preferably benzene or toluene). Preferred reaction temperatures range from −80 to 120° C.

The hydroxypyridazine may then be treated with a halogenating agent to give halo derivatives which may be isolated or prepared in situ. Halogenating agents include, but are not limited to, $SOCl_2$, $POCl_3$, $PCl_3$, $PCl_5$, $POBr_3$, $PBr_3$ or $PBr_5$. These intermediates may be treated with a compound of the Formula $R^7H$ in the presence or absence of a base in an inert solvent. Bases may include, but are not limited to, alkali metal hydrides (preferably sodium hydride), alkali metal alkoxides (1 to 6 carbons)(preferably sodium methoxide or sodium ethoxide), alkaline earth metal hydrides, alkali metal dialkylamides (preferably lithium di-isopropylamide), alkali metal bis(trialkylsilyl)amides (preferably sodium bis(trimethylsilyl)amide), trialkyl amines (preferably N,N-di-isopropyl-N-ethyl amine or triethylamine), aromatic amines (preferably pyridine) or alkyl-lithiums in the presence or absence of salts or complexes of Cu, Ce, Mg, Pd. Ni, Zn, Sn. Inert solvents may include, but are not limited to, lower alkanenitriles (1 to 6 carbons, preferably acetonitrile), dialkyl ethers (preferably diethyl ether), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide), aromatic hydrocarbons (preferably benzene or toluene) or haloalkanes of 1 to 10 carbons and 1 to 10 halogens (preferably dichloromethane). Preferred reaction temperatures range from −20 to 100° C.

The resulting compounds may then be reacted with an alkylating agent of the Formula $R^1X$ (where $R^1$ is defined above) and X is halo, alkanesulfonyloxy, arylsulfonyloxy or haloalkane-sulfonyloxy) in the presence or absence of a base in an inert solvent to provide compounds of Formula (Id). Bases may include, but are not limited to, alkali metal hydrides (preferably sodium hydride), alkali metal alkoxides (1 to 6 carbons)(preferably sodium methoxide or sodium ethoxide), alkaline earth metal hydrides, alkali metal dialkylamides (preferably lithium di-isopropylamide), alkali metal bis(trialkylsilyl)amides (preferably sodium bis(trimethylsilyl)amide), trialkyl amines (preferably N,N-di-isopropyl-N-ethyl amine or triethylamine), aromatic amines (preferably pyridine) or alkyl-lithiums in the presence or absence of salts or complexes of Cu, Ce, Mg, Pd, Ni, Zn, Sn. Inert solvents may include, but are not limited to, lower alkanenitriles (1 to 6 carbons, preferably acetonitrile), dialkyl ethers (preferably diethyl ether), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide), aromatic hydrocarbons (preferably benzene or toluene) or haloalkanes of 1 to 10 carbons and 1 to 10 halogens (preferably dichloromethane). Preferred reaction temperatures range from −20 to 100° C.

Alternatively, alkylation to compounds of Formula (Ib) by treatment with a azodicarboxylate ester $R^bO_2CN=NCO_2R^b$ (where $R^b$ is a lower alkyl group) and a compound of the Formula $R^1OH$ in the presence of a triarylphosphine (where aryl is phenyl or furyl, each optionally substituted by 0 to 3 alkyl groups) in an inert solvent. Inert solvents may include, but are not limited to, lower alkanenitriles (1 to 6 carbons, preferably acetonitrile), dialkyl ethers (preferably diethyl ether), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide), aromatic hydrocarbons (preferably benzene or toluene) or haloalkanes of 1 to 10 carbons and 1 to 10 halogens (preferably dichloromethane). Preferred reaction temperatures range from −20 to 100° C.

Scheme 5

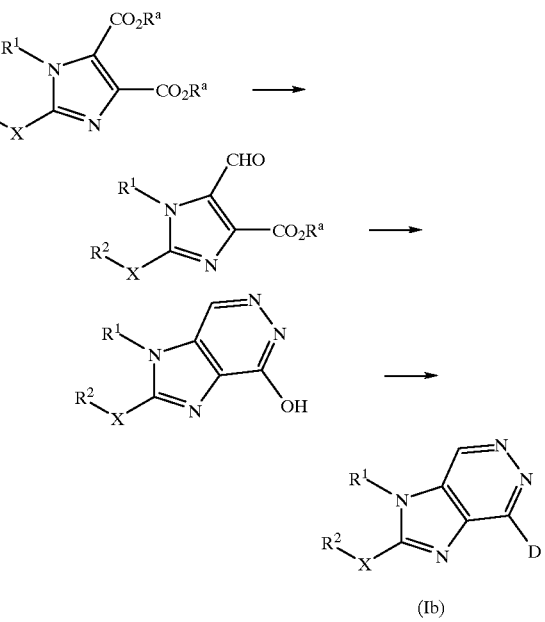

(Ib)

Compounds of Formula (Ib) may also be prepared, using the procedures outlined in Scheme 5. The starting diester may be treated with a reducing agent in inert solvent to afford an aldehyde. Reducing agents include, but are not limited to, alkali metal or alkaline earth metal borohydrides (preferably lithium or sodium borohydride), borane, dialkylboranes (such as di-isoamylborane), alkali metal aluminum hydrides (preferably lithium aluminum hydride), alkali metal (trialkoxy)aluminum hydrides, or dialkyl aluminum hydrides (such as di-isobutylaluminum hydride). Inert solvents may include, but are not limited to, alkyl alcohols (1 to 6 carbons), dialkyl ethers (preferably diethyl ether), cyclic ethers (preferably tetrahydrofuran or 1,4-dioxane), aromatic hydrocarbons (preferably benzene or toluene). Preferred reaction temperatures range from −80 to 100° C.

Alternatively, the aldehyde may be prepared by a two step sequence: treatment with a reducing agent in an inert solvent, followed by treatment with an oxidizing agent in an inert solvent. Reducing agents and inert solvents are defined above. Oxidizing agents include, but are not limited to, combinations of oxalyl chloride, dimethyl sulfoxide and organic bases, MnO2, KMnO4, pyridinium dichromate, pyridinium chlorochromate or combinations of $SO_3$ and organic bases. Organic bases include, but are not limited to, trialkyl amines (preferably N,N-di-isopropyl-N-ethyl amine or triethylamine) or aromatic amines (preferably pyridine).

The aldehyde may then be reacted with hydrazine in an inert solvent to form an imidazole. Inert solvents may include, but are not limited to, alkyl alcohols (1 to 6 carbons), dialkyl ethers (preferably diethyl ether), cyclic ethers (preferably tetrahydrofuran or 1,4-dioxane), aromatic hydrocarbons (preferably benzene or toluene). Preferred reaction temperatures range from −80 to 120° C.

The hydroxy group may then be treated with sulfonylating agents in the presence or absence of a base to give alkanesulfonyloxy, arylsulfonyloxy or haloalkylsulfonyloxy derivatives, which may be isolated or used in situ. Sulfonylating agents include, but are not limited to, alkanesulfonyl halides or anhydrides (such as methanesulfonyl chloride or methanesulfonic acid anhydride), arylsulfonyl halides or anhydrides (such as p-toluenesulfonyl chloride or anhydride) or haloalkylsulfonyl halides or anhydrides (preferably trifluoromethanesulfonic anhydride). Bases may include, but are not limited to, alkali metal hydrides (preferably sodium hydride), alkali metal alkoxides (1 to 6 carbons)(preferably sodium methoxide or sodium ethoxide), alkaline earth metal hydrides, alkali metal dialkylamides (preferably lithium di-isopropylamide), alkali metal bis(trialkylsilyl)amides (preferably sodium bis(trimethylsilyl)amide), trialkyl amines (preferably N,N-di-isopropyl-N-ethyl amine or triethylamine) or aromatic amines (preferably pyridine). Inert solvents may include, but are not limited to, lower alkanenitriles (1 to 6 carbons, preferably acetonitrile), dialkyl ethers (preferably diethyl ether), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide), aromatic hydrocarbons (preferably benzene or toluene) or haloalkanes of 1 to 10 carbons and 1 to 10 halogens (preferably dichloromethane).

The sulfonylated intermediates may then be reacted with compounds of the formula D—B(OH)2 in the presence of salts or complexes of Pd, Ni, or Sn, in the presence or absence of a base in an inert solvent to provide compounds of Formula (Ib). Bases may include, but are not limited to, alkaline earth metal carbonates, alkaline earth metal bicarbonates, alkaline earth metal hydroxides, alkali metal carbonates, alkali metal bicarbonates, alkali metal hydroxides, alkali metal hydrides (preferably sodium hydride), alkali metal alkoxides (1 to 6 carbons)(preferably sodium methoxide or sodium ethoxide), alkaline earth metal hydrides, alkali metal dialkylamides (preferably lithium di-isopropylamide), alkali metal bis(trialkylsilyl)amides (preferably sodium bis(trimethylsilyl)amide), trialkyl amines (preferably N,N-di-isopropyl-N-ethyl amine or triethylamine) or aromatic amines (preferably pyridine). Inert solvents may include, but are not limited to, lower alkanenitriles (1 to 6 carbons, preferably acetonitrile), dialkyl ethers (preferably diethyl ether), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide), aromatic hydrocarbons (preferably benzene or toluene) or haloalkanes of 1 to 10 carbons and 1 to 10 halogens (preferably dichloromethane).

Scheme 6

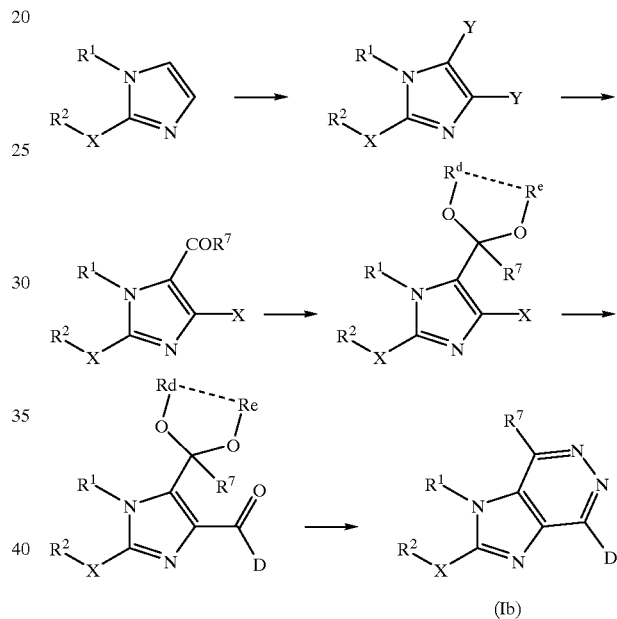

(Ib)

Compounds of Formula (Ib) may also be prepared by the procedures outlined in Scheme 6. The starting imidazoles may treated with halogenating agents in an inert solvent to provide a dihalo-imidazole. Halogenating agents include, but are not limited to, $SOCl_2$, $POCl_3$, $PCl_3$, $PCl_5$, $POBr_3$, $PBr_3$ or $PBr_5$. Inert solvents may include, but are not limited to, lower alkanenitriles (1 to 6 carbons, preferably acetonitrile), dialkyl ethers (preferably diethyl ether), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide), aromatic hydrocarbons (preferably benzene or toluene) or haloalkanes of 1 to 10 carbons and 1 to 10 halogens (preferably dichloromethane).

One halogen may be replaced via treatment with a compound of Formula $R^cM$ (where $R^c$ is lower alkyl and M may be Li, Na, MgBr, MgCl, ZnCl, $CeCl_2$) in an inert solvent, followed by reaction with a compound of Formula $R^7$—(C=O)—Y (where $R^7$ is defined above and Y is halogen, lower alkoxy, lower alkanoyloxy or $(R^dO)_2(P=O)O$ (where $R^d$ is lower alkyl or phenyl)). The acyl compounds my be protected by reaction with acetal- or ketal-forming reagents (where $R^d$ or $R^e$ are each lower alkyl, or taken together they form a lower alkylene chain). These acetal- or ketal-forming reagents may be combinations of lower alkyl alcohols or diols and acids or trialkylorthoformates and acids. Such acids may be present in catalytic or stoichiometric amounts. Such acids include, but are not limited to, alkanoic acids of 2 to 10 carbons (preferably acetic acid), arylsulfonic acids (preferably p-toluenesulfonic acid or benzenesulfonic acid), alkanesulfonic acids of 1 to 10 carbons (preferably methanesulfonic acid), hydrochloric acid, sulfuric acid or phosphoric acid. Inert solvents may include, but are not limited to, alkyl alcohols (1 to 8 carbons, preferably methanol or ethanol), lower alkanenitriles (1 to 6 carbons, preferably acetonitrile), dialkyl ethers (preferably glyme or diglyme), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide), aromatic hydrocarbons (preferably benzene or toluene) or halocarbons of 1 to 10 carbons and 1 to 10 halogens (preferably chloroform). Preferred reaction temperatures range from ambient temperature to 150° C.

Moiety D may be attached by treatment with a compound of Formula RCM (where $R^c$ is lower alkyl and M may be Li, Na, MgBr, MgCl, ZnCl, $CeCl_2$) in an inert solvent, followed by reaction with a compound of Formula D—(C=O)—Y (where D is defined above and Y is halogen, lower alkoxy, lower alkanoyloxy or $(R^dO)_2(P=O)O$ (where $R^d$ is lower alkyl or phenyl)). Inert solvents may include, but are not limited to, dialkyl ethers (preferably diethyl ether), cyclic ethers (preferably tetrahydrofuran or 1,4-dioxane), or aromatic hydrocarbons (preferably benzene or toluene).

Compounds of Formula (Ib) may finally be prepared by (a) hydrolysis with an acid, followed by (b) reaction with hydrazine in an inert solvent. Acids include, but are not limited to, alkanoic acids of 2 to 10 carbons (preferably acetic acid), arylsulfonic acids (preferably p-toluenesulfonic acid or benzenesulfonic acid), alkanesulfonic acids of 1 to 10 carbons (preferably methanesulfonic acid), hydrochloric acid, sulfuric acid or phosphoric acid. Inert solvents may include, but are not limited to, alkyl alcohols (1 to 8 carbons, preferably methanol or ethanol), lower alkanenitriles (1 to 6 carbons, preferably acetonitrile), dialkyl ethers (preferably glyme or diglyme), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide), aromatic hydrocarbons (preferably benzene or toluene) or halocarbons of 1 to 10 carbons and 1 to 10 halogens (preferably chloroform). Preferred reaction temperatures for steps (a) or (b) range from ambient temperature to 150° C.

If intermediates contain functional groups which are sensitive to the reaction conditions employed, these groups may be protected using methods known to those skilled in the art. These methods include, but are not limited to, those described in *Protective Groups in Organic Synthesis* (Greene, Wuts; 2nd ed., 1991, John Wiley & Sons, Inc.).

Other features of the invention will become apparent in the course of the following descriptions of exemplary embodiments which are given for illustration of the invention and are not intended to be limiting thereof.

EXAMPLES

Abbreviations used in the Examples are defined as follows: "1 x" for once, "2 x" for twice, "3 x" for thrice, "° C." for degrees Celsius, "eq" for equivalent or equivalents, "g" for gram or grams, "mg" for milligram or milligrams, "mL" for milliliter or milliliters, "$^1H$" for proton, "h" for hour or hours, "M" for molar, "min" for minute or minutes, "MHz" for megahertz, "MS" for mass spectroscopy, "NMR" for nuclear magnetic resonance spectroscopy, "rt" for room temperature, "tlc" for thin layer chromatography, "v/v" for volume to volume ratio. "α", "β", "R" and "S" are stereochemical designations familiar to those skilled in the art.

Example 1

4-(2,4-Dichlorophenyl)-2-ethyl-1-(1-ethyl)Propyl-imidazo [4,5-d]Pyridazine

Part A: 4,5-dibromo-2-ethyl-1H-imidazole:

To a solution of 2-ethylimidazole (57.6 g, 0.6 moles) in $CHCl_3$ (700 mL) was cooled to 0–5° C. and then added bromine (76.8 mL, 1.5 moles) dropwise over 60 mins under nitrogen atmosphere. The mixture was stirred at 5° C. for 60 mins and then at room temperature for 2 days. TLC (1:10 MeOH/$CH_2Cl_2$) revealed disappearance of starting material (Rf=0.25) and showed a new spot (Rf=0.45). The mixture was cooled back to 0° C. and added dropwise 2N aq. NaOH (750 mL) to dissolve the yellow solid separated from the mixture. The aq. layer was separated and extracted the organic layer with 250 mL of 2N NaOH. The combined aq. extracts was acidified to pH 8.0 using con. HCl. The cream colored solid separated was filtered, washed with water and dried in vacuum at 50° C. to afford 55.0 g of desired product (mp 149–150° C., 36%). $^1H$ NMR ($CDCl_3$): ∂ 1.27–1.3 (t, 3H, $CH_3$), 2.7–2.8 (q, 2H, $CH_2$). Mass spectrum (CI-$NH_3$): m/z 255.0 ($MH^+$).

Part B: 4,5-dibromo-2-ethyl-1-(1-ethyl)propyl-1H-imidazole:

A mixture of part A material (8.3 g, 0.033 moles), triphenylphosphine (9.4 g, 0.036 moles) and molecular sieves (10 g) in THF (100 mL) was cooled to 0 to –5° C. and then added 3-pentanol (3.4 g, 0.039 moles) under nitrogen atmosphere. The mixture was stirred at 0° C. for 30 mins and then added diisopropylazodicarboxylate (7.2 g, 0.033 moles) dropwise over 20 mis. The mixture was stirred at 0° C. for 2h followed by room temperature for 2 days and TLC (1:50 MeOH/$CH_2Cl_2$) revealed a new spot at Rf=0.5. The undissolved material was filtered, washed with dichloromethane and stripped off the solvent in vacuum to afford yellow liquid. The crude was purified by flash column chromatography using chloroform as eluent to afford 4.9 g (46.5%) of colorless oil. $^1H$ NMR ($CDCl_3$): ∂ 0.79–0.84 (t, 6H, 2*$CH_3$), 1.3–1.35 (t, 3H, $CH_3$), 1.82–2.18 (m, 4H, 2*$CH_2$), 2.65–2.72 (q, 2H, $CH_2$), 3.95 (m, 1H, CH). Mass spectrum (CI-$NH_3$): m/z 325.0 ($MH^+$).

Part C: 4-bromo-2-ethyl-1-(1-ethyl)propyl-1H-imidazole-5-carboxaldehyde:

A solution of part B material (3.7 g, 0.0114 moles) in THF (40.0 mL) was cooled to –78° C. under nitrogen atmosphere and then added dropwise 1.6 M n-BuLi solution in hexane (7.4 mL, 0.0119 moles) over 30 mins. The mixture was stirred at –78° C. for 1 h and then added dropwise DMF (2.7 mL, 0.0342 moles) over 15 mins. The mixture was stirred at –78° C. for 60 mins and quenched with saturated $NH_4Cl$ (10 mL) at –78° C. TLC (1:50 MeOH/$CH_2Cl_2$) revealed a new spot at Rf=0.55 along with disappearence of starting material spot at Rf=0.5. The reaction mixture was extracted with diethyl ether (3 * 25 mL), washed with brine and dried ($MgSO_4$). The solvent was stripped off in vacuo to afford 3.6 g of yellow oil which was purified by flash column chromatography on silica gel using chloroform as eluent to afford 1.97 g (64% yield) of colorless oil. $^1H$ NMR ($CDC_{13}$): ∂

0.73–0.83 (t, 6H, 2*CH$_3$), 1.35–1.40 (t, 3H, CH$_3$), 1.59–2.17 (m, 4H, 2*CH$_2$), 2.72–2.80 (g, 2H, CH$_2$), 3.95 (m, 1H, CH), 9.67 (s, 1H, CHO). Mass spectrum (CI-NH$_3$): M/z 275.1 (M+2H).

Part D: 4-bromo-2-ethyl-1-(1-ethyl)propyl-1H-imidazole-5-carboxaldehyde ethylene acetal:

A mixture of part C material (1.75 g, 0.0064 moles) in benzene (150 mL) was treated with ethylene glycol (1.2 mL, 0.025 moles), pyridine (0.0035 moles) and p-toluenesulfonic acid mono hydrate (0.0035 moles). The reaction mixture was heated at reflux in a 20 mL capacity Dean-Stark trap equipped apparatus for 24 h and TLC (1:50 MeOH/CH$_2$Cl$_2$) revealed a new spot at Rf=0.35 (visible under iodine). The reaction mixture was cooled to room temperature, diluted with EtOAc (50 mL), washed with 10% sodium bicarbonate, brine and dried (MgSO$_4$). The solvent was evaporated under reduced pressure to furnish yellow oil. The crude was purified by flash column chromatography on silica gel using 25% ethyl acetate/chloroform mixture to afford 1.96 g (97%) white solid (mp 70–71° C.). $^1$H NMR (CDCl$_3$): $\partial$ 0.78–0.89 (t, 6H, 2*CH$_3$), 1.29–1.36 (t, 3H, CH$_3$), 1.77–1.90 (m, 4H, 2*CH$_2$), 2.70–2.73 (q, 2H, CH$_2$), 3.98–4.3 (m, 5H, CH and 2*CH$_2$), 5.86 (s, 1H, CH). Mass spectrum (CI-NH$_3$): m/z 317.1 (M$^+$). Anal. calcd for C$_{13}$H$_{22}$Br$_1$N$_2$O$_2$: C, 49.22; H, 6.67; N, 8.83. Found: C, 49.43; H, 6.61; N, 8.78.

Part E: 4-(2,4-dichlorobenzoyl)-2-ethyl-1-(1-ethyl)propyl-1H-imidazole-5-carboxaldehyde:

A solution of part D material (1.08 g, 0.0034 moles) in THF (20.0 mL) was cooled to −78° C. and then added dropwise 1.6 M n-BuLi in hexane (2.4 mL, 0.004 moles) over 15 mins under nitrogen atmosphere. The mixture was stirred at −78° C. for 2 1/2 h and then added a solution of 2,4-dichlorobenzoyl chloride (0.84 g, 0.004 moles) in THF (5.0 mL) over 15 mins. The mixture was stirred at −78° C. for 6 h followed by room temperature overnight and TLC (30:70 EtOAc/hexane) showed a new spot at Rf=0.43. The mixture was quenched with saturated NH$_4$Cl (10.0 ml), extracted with ethyl acetate (3*30 mL), washed with brine and dried (MgSO$_4$). The solvent was stripped off in vacuo to afford crude product which was purified by flash column chromatography on a silica gel using 15% EtOAC/hexane to afford 0.61 g (44% yield) of desired product as yellow oil. Mass spectrum (CI-NH$_3$): m/z 411.2 (M$^+$). The acetal was dissolved in acetone (15.0 mL) and treated with 3.0 M aqeous HCl (30.0 mL) at room temperature. The reaction mixture was stirred for 24 h at this temperature and TLC (30:70 EtOAc/hexane) showed a new spot at Rf=0.55. It was then quenched with saturated NaCl (50.0 ml), extracted with ethyl acetate (3*50 mL), washed with brine and dried (MgSO$_4$). The solvent was removed in vacuum to afford yellow liquid and purified the crude by flash column chromatography on a silica gel using 15% EtOAC/hexane to afford 0.28 g (51% yield) of desired product as yellow solid (mp 85–86° C.). $^1$H NMR (CDC$_{13}$): $\partial$ 0.785 (m, 6H, 2*CH$_3$), 1.28–1.33 (t, 3H, CH$_3$), 1.90–2.23 (m, 4H, 2*CH$_2$), 2.74–2.82 (g, 2H, CH$_2$), 3.98–4.05 (m, 1H, CH), 7.34–7.37 (d, 1H, aromatic), 7.45–7.46 (d, 1H, aromatic), 7.55–7.58 (d, 1H, aromatic). Mass spectrum (CI-NH$_3$) : m/z 367 (M$^+$). Anal. calcd for C$_{18}$H$_{20}$Cl$_2$N$_2$O$_2$: C, 58.87; H, 5.50; N, 7.64. Found: C, 58.91; H, 5.60; N, 7.44.

Part F: 4-(2,4-dichlorophenyl)-2-ethyl-1-(1-ethyl)propyl-imidazo[4,5-d]pyridazine:

A mixture of part E material (0.110 g, 0.0003 moles) in ethanol (15 mL) was treated with anhydrous hydrazine (0.125 g, 0.0039 moles) and refluxed under nitrogen for 4h. TLC (1:10 MeOH/CH$_2$Cl$_2$) showed a new spot at Rf=0.6. The solvent was removed under vacuum and purified the crude by flash column chromatography on a silica gel using 1:100 MeOH/CH$_2$Cl$_2$ to afford 105 mg (97% yield) of the product as yellow oil and tituration of the oil with diethyl ether (1.0 mL) gave 65 mg of white crystalline solid (mp 136–137° C.). $^1$H NMR (CDC$_{13}$): $\partial$ 0.82–0.87 (t, 6H, 2*CH$_3$), 1.41–1.46 (t, 3H, CH$_3$), 2.05–2.21 (m, 4H, 2*CH$_2$), 2.95–3.03 (q, 2H, CH$_2$), 4.16–4.26 (m, 1H, CH), 7.41–7.44 (d, 1H, aromatic), 7.58–7.59 (d, 1H, aromatic), 7.64–7.67 (d, 1H, aromatic), 9.49 (s, 1H, 9 CH). Mass spectrum (CI-NH$_3$): m/z 363 (M$^+$). Anal. calcd for C$_{18}$H$_{20}$Cl$_2$N$_4$: C, 59.51; H, 5.56; N, 15.42. Found: C, 59.53; H, 5.79; N, 14.70.

Example 95

4-(2,4-Dichlorophenyl)-2-ethyl-1-(1-cyclopropyl)propyl-imidazo[4,5-c]pyridazine

Part A: 4-Ethoxycarbonyl-5-(2,4-dichlorophenyl)-1,6-dihydropyridazin-3-one:

A 1M solution of TiCl$_4$ in CH$_2$Cl$_2$ (100 mL) was slowly added via syringe to anhydrous THF (500 mL) cooled to −5° C. under N$_2$ with vigorous stirring. After stirring for 15 min, a solution of 2,2',4'-trichloroacetophenone (11 g, 49.2 mmol) in THF was added to the mixture, followed by addition of diethyl malonate (7.4 mL, 48.4 mmol). Pyridine (16.5 mL) was then added dropwise, and the reaction mixture was stirred for 16 h at room temperature. The mixture was then partitioned between Et$_2$O and water, and the aqueous layer was washed with Et$_2$O. Organic extracts were combined and dried over MgSO$_4$, filtered and evaporated in vacuo to afford the olefin as a pale yellow oil.

To a solution of the olefin in EtOH was added 1.5 equivalents of hydrazine monohydrate and 1.5 equivalents of diisopropylethylamine. The mixture was refluxed for 4h, then evaporated in vacuo. The residue was chromatographed on silica gel (100% Hexane to 20% EtOAc/Hexane gradient) to yield 5.8 g of a pale yellow solid. $^1$H NMR (300 MHz, CDCl$_3$): $\partial$ 9.39 (s, 1H), 7.42–7.26 (m, 3H), 4.23 (quart., 2H), 3.6 (m, 1H), 3.33–3.11 (m, 2H), 1,27 (t, 3H).

Part B: 3-Bromo-4-ethoxycarbonyl-5-(2,4-dichlorophenyl)pyridazine:

To a solution of 1.1 g of product from Part A in toluene was added 2 equivalents of POBr3 and the mixture was refluxed for 3h. The reaction mixture was evaporated in vacuo and the residue was chromatographed on silica gel to yield desired product (100% Hexane to 15% EtOAc/Hex gradient). Mass spectrum (APcI): (M+H)$^+$ m/z 374.8 (60%), 376.8 (100%), 378.8 (43%).

Part C: 4-Amino-3-bromo-5-(2,4-dichlorophenyl)pyridazine:

To a solution of product from Part B in THF was added a solution of 5 equivalents of LiOH monohydrate in water. A small amount of MeOH was added to make the mixture homogenous. The reaction mixture was stirred at room temperature for 3 h. The mixture was then partitioned between Et$_2$O and 1N HCl. The organic extract was dried over MgSO$_4$, filtered, and evaporated in vacuo to give the acid.

To a solution of the acid in t-BuOH was added 1.1 equivalents of both DPPA (diphenyphosphorylazide) and triethyamine. The reaction mixture was refluxed for 16 h, then concentrated in vacuo. The residue was partitioned between Et$_2$O and water. The organic extract was dried over MgSO$_4$, filtered, and evaporated in vacuo. This residue was dissolved in CH$_2$Cl$_2$ and trifluoroacetic acid was added. This solution was stirred at room temperature for 4 h, then evaporated in vacuo to afford the crude amine.

Part D: 4-(2,4-Dichlorophenyl)-2-ethyl-1-(1-cyclopropyl)propyl-imidazo[4,5-c]pyridazine:

To a mixture of the amine in toluene is added 1-cyclopropyl-1-propylamine hydrochloride (1.2 equivalents), sodium t-butoxide (2.5 equivalents), $Pd_2(dba)_3$ (0.05 equivalents), and BINAP (0.025 equivalents). The reaction mixture is stirred at 70° C. for 16 h. The mixture is then cooled and partitioned between $Et_2O$ and water. The organic extract is dried over $MgSO_4$, filtered, and evaporated in vacuo. To the crude residue is added triethylorthopropionate and 1 drop of conc. HCl and the mixture is refluxed for 3 h then evaporated in vacuo. To this residue is added o-xylene and p-toluenesulfonic acid, and this mixture is refluxed for 3 h then evaporated in vacuo. The residue is chromatographed on silica gel (100% hexane to 40% EtOAc/Hexane gradient) to yield the title compound.

Example 1121

Synthesis of 2-ethyl-1-(1-ethyl)propyl-4-(2,4,6-trimethylphenyl)-imidazo[4,5-d]pyridazine Part A: 2-Ethyl-1-(1-ethyl)propyl-4-(2,4,6-trimethylbenzoyl)-1H-imidazole-5-carboxaldehyde:

A mixture of Part D material of Example 1 (0.82 g, 0.0030 moles) in THF (20.0 mL) was cooled to −78° C. and then added dropwise 1.6 M n-BuLi in hexane (2.0 mL, 0.0033 moles) over 15 mins under nitrogen atmosphere. The mixture was stirred at −78° C. for 3 h and then added a solution of 2,4,6-trimethylbenzoyl chloride (0.60 g, 0.0033 moles) in THF (5.0 mL) over 15 mins. The mixture was stirred at −78° C. for 6 h followed by room temperature overnight for 16 h and TLC (30:70 EtOAc/hexane) showed both starting material and product had same Rf values. The mixture was quenched with saturated $NH_4Cl$ (10.0 ml), extracted with ethyl acetate (3*30 mL), washed with brine and dried ($MgSO_4$). The solvent was stripped off in vacuo to afford crude product (1.0 g) as yellow semi solid. Mass spectrum (APcI-positive): m/z 385.4 (M+H). The acetal was dissolved in acetone (15.0 mL) and treated with 3.0 M aqeous HCl (30.0 mL) at room temperature. The reaction mixture was stirred for 24 h at this temperature and TLC (30:70 EtOAc/hexane) showed a new spot at Rf=0.55 along with unreacted starting material acetal. Therefore continued further for 24 h and found to contain still some unreacted starting material. It was then quenched with saturated NaCl (50.0 ml), extracted with ethyl acetate (3*50 mL), washed with brine and dried ($MgSO_4$). The solvent was removed in vacuum to afford yellow liquid and purified the crude by flash column chromatography on a silica gel using dichloromethane as eluent to afford 0.3 g (29% yield) of desired product as yellow solid (mp 119–120° C.). $^1H$ NMR ($CDC_{13}$): ? 0.779 (m, 6H, 2*$CH_3$), 1.26–1.31 (t, 3H, $CH_3$), 1.90–1.95 (m, 4H, 2*$CH_2$), 2.16–2.31 (2 S, 9H, aromatic $CH_3$), 2.74–2.81 (q, 2H, $CH_2$), 3.98–4.05 (m, 1H, CH), 6.87 (s, 2H, aromatic), 10.3 (s, 1H, CHO). Mass spectrum (CI-$NH_3$): m/z 341 (M+H). Anal. calcd for $C_{21}H_{28}N_2O_2$: C, 74.08; H, 8.30; N, 8.24. Found: C, 74.33; H, 8.41; N, 8.18.

Part B: Title Compound:

A mixture of Part A material of Example 1121 (0.2 g, 0.00059 moles) in ethanol (15 mL) was treated with anhydrous hydrazine (0.245 g, 0.0077 moles) and refluxed under nitrogen for 1 h. TLC (1:50 MeOH/$CH_2Cl_2$) showed a new spot at Rf=0.45. The solvent was removed under vacuum and purified the crude by treatment with ethanol to afford white solid (0.2 g, mp 164–165° C.). $^1H$ NMR ($CDC_{13}$): ? 0.77–0.82 (t, 6H, 2*$CH_3$), 1.24–1.29 (t, 3H, $CH_3$), 1.86–1.92 (m, 4H, 2*$CH_2$), 2.14 (s, 6H, 2*$CH_3$), 2.29 (s, 3H, $CH_3$), 2.68–2.76 (q, 2H, $CH_2$), 5.52 (bs, 3H, CH&$NH_2$), 6.85 (s, 2H, aromatic), 8.16 (s, 1H,-CH=N). Mass spectrum (CI-$NH_3$): m/z 355 (M+H). The reaction stopped at hydrazone stage and failed to cyclize even after 48 h in refluxing ethanol. The hydrazone (0.16 g, 0.45 mmol) was taken in 10 mL of ethylene glycol and refluxed for 2 h at 200° C. Mass spectrum (CI-$NH_3$): m/z 337 (m+H) revealed desired product and cooled the reaction mixture to room temp. and diluted with 25 ml of water, extracted with ethyl acetate (3*15 mL), washed with brine and dried ($MgSO_4$). The crude was purified by flash column chromatography on a silica gel using 1: 50 MeOH/$CH_2Cl_2$ to afford 71 mg (47% yield) of the product as yellow crystalline solid (mp 151–152° C.). $^1H$ NMR ($CDC_{13}$): ? 0.82–0.87 (t, 6H, 2*$CH_3$), 1.35–1.41 (t, 3H, $CH_3$), 2.0 (s, 6H, 2*$CH_3$), 2.1–2.17 (q, 4H, $CH_2$), 2.37 (s, 3H, $CH_3$), 2.92–3.0 (q, 2H, $CH_2$), 4.16–4.22 (m, 1H, CH), 6.98 (s, 2H, aromatic), 9.46 (s, 1H, 9 CH). Mass spectrum (CI-$NH_3$): m/z 337 (M+H). Anal. calcd for $C_{21}H_{28}N_4$: C, 74.96; H, 8.40; N. 16.65. Found: C, 74.77; H, 8.62; N, 15.42.

Example 1122

4-(2,4-dichloro-5-fluorophenyl)-2-ethyl-1-(1-ethyl)propyl-imidazo[4,5-d]pyridazine Part A: 2-ethyl-1-(1-ethyl)propyl-4-(2,4-dichloro-5-fluorobenzoyl)-1H-imidazole-5-carboxaldehyde:

A mixture of Part D material of Example 1 (0.82 g, 0.0030 moles) in THF (20.0 mL) was cooled to −78° C. and then added dropwise 1.6 M n-BuLi in hexane (2.0 mL, 0.0033 moles) over 15 mins under nitrogen atmosphere. The mixture was stirred at −78° C. for 3 h and then added a solution of 2,4-dichloro-5-F-benzoyl chloride (0.75 g, 0.0033 moles) in THF (5.0 mL) over 15 mins. The mixture was stirred at −78° C. for 6 h followed by room temperature overnight for 16 h and TLC (30:70 EtOAc/hexane) showed absence of starting material (Rf=0.5) and a new spot for the product at Rf=0.64. The mixture was quenched with saturated $NH_4Cl$ (25.0 ml), extracted with ethyl ether (3*30 mL), washed with brine and dried (MgSO). The solvent was stripped off in vacuo to afford crude product (1.5 g) as yellow oil and purified by flash column chromatography on a silica gel using dichloromethane as eluent to afford desired product as colorless viscous oil (0.62 g, 48%). $^1H$ NMR ($0D01_3$) : ? 0.86–0.91 (t, 6H, 2*$CH_3$), 1.25–1.30 (t, 3H, $CH_3$), 1.83–1.92 (q, 4H, 2*$CH_2$), 2.70–2.75 (q, 2H, $CH_2$), 2.74–2.81 (q, 2H, $CH_2$), 4.04–4.18 (m, 4H, 2*$OCH_2$), 4.41–4.51 (m, 1H, CH), 6.69 (s, 1H, —CH), 7.38–7.31 (d, 1H, aromatic), 7.45–7.47 (d, 1H, aromatic). Mass spectrum (APcI-positive): m/z 429.2 ($M^+$). The acetal was dissolved in acetone (15.0 mL) and treated with 3.0 M aqeous HCl (30.0 mL) at room temperature. The reaction mixture was stirred for 24 h at this temperature and TLC (30:70 EtOAc/hexane) showed a new spot at Rf=0.67 along with disappearence of starting material acetal. It was then quenched with saturated NaCl (50.0 ml), extracted with ethyl acetate (3*50 mL), washed with brine and dried ($MgSO_4$). The solvent was removed in vacuum to afford yellow liquid and purified the crude by flash column chromatography on a silica gel using dichloromethane as eluent to afford 0.43 g (80% yield) of desired product as white solid (mp 70–71° C.). $^1H$ NMR ($CDC_{13}$): ? 0.79 (m, 6H, 2*$CH_3$), 1.28–1.33 (t, 3H, $CH_3$), 1.90–2.2 (m, 4H, 2*$CH_2$), 2.74–2.82 (q, 2H, $CH_2$), 3.98–4.05 (m, 1H, CH), 7.42–7.45 (d, 1H, aromatic), 7.50–7.52 (d, 1H, aromatic), 10.4 (s, 1H, CHO). Mass spectrum (CI-$NH_3$): m/z 385 ($M^+$). Anal. calcd for $C_{18}H_{19}N_2O_2Cl_2F$,: C, 56.12; H, 4.97; N, 7.27. Found: C,56.27; H,4.95; N, 7.12.

Part B: Title Compound:

A mixture of Part A material of Example 1122 (0.230 g, 0.0006 moles) in ethanol (15 mL) was treated with anhydrous hydrazine (0.25 g, 0.0077 moles) and refluxed under nitrogen for 16 h. TLC (1:10 MeOH/CH$_2$Cl$_2$) showed a new spot at Rf=0.6. The solvent was removed under vacuum and purified the crude by flash column chromatography on a silica gel using 1:50 MeOH/CH$_2$Cl$_2$ to afford 194 mg of pale yellow oil and tituration of the oil with hexane (1.0 mL) gave 59 mg (26%) of white crystalline solid (mp 85–87° C.). $^1$H NMR (CDC$_{13}$): ? 0.82–0.87 (t, 6H, 2*CH$_3$), 1.42–1.47 (t, 3H, CH$_3$), 2.08–2.21 (m, 4H, 2*CH$_2$), 2.98–3.03 (q, 2H, CH$_2$), 4,25 4.16–4.26 (m, 1H, CH), 7.53–7.56 (d, 1H, aromatic), 7.62–7.64 (d, 1H, aromatic), 9.50 (s, 1H, 9 CH). Mass spectrum (CI-NH$_3$): m/z 381 (M$^+$). HRMS calcd. for C$_{18}$H$_{20}$Cl$_2$F$_1$N$_4$: 381.1048. Found: 381.1057 (M+H).

Example 1123

2-Ethyl-1-(1-ethyl)propyl-4-(2,4-dimethoxybenzoyl)-1H-imidazole-5-carboxaldehyde A mixture of Part D material of Example 1 (0.82 g, 0.0030 moles) in THF (20.0 mL) was cooled to −78° C. and then added dropwise 1.6 M n-BuLi in hexane (2.0 mL, 0.0033 moles) over 15 mins under nitrogen atmosphere. The mixture was stirred at −78° C. for 3 h and then added a solution of 2,4-dimethoxybenzoyl chloride (0.66 g, 0.0033 moles) in THF (5.0 mL) over 15 mins. The mixture was stirred at −78° C. for 6 h followed by room temperature overnight for 16 h and The mixture was stirred at −78° C. for 6 h followed by room temperature overnight for 16 h and TLC (30:70 EtOAc/hexane) showed absence of starting material (Rf= 0.5) and a new spot for the product at Rf=0.57. The mixture was quenched with saturated NH$_4$Cl (25.0 ml), extracted with ethyl ether (3*30 mL), washed with brine and dried (MgSO$_4$). The solvent was stripped off in vacuo to afford crude product (1.3 g) as yellow oil and purified by flash column chromatography on a silica gel using 1:100 methanol/dichloromethane as eluent to afford desired product as pale yellow viscous oil (0.39 g, 32%). Mass spectrum (APcI-positive): m/z 403.3 (M+H$^+$). The acetal was dissolved in acetone (15.0 mL) and treated with 3.0 M aqeous HCl (30.0 mL) at room temperature. The reaction mixture was stirred for 24 h at this temperature and TLC (1:10 MeOH/CH$_2$Cl$_2$) showed two new spots at Rf=0.92 & 0.62. It was then quenched with saturated NaCl (50.0 ml), extracted with ethyl acetate (3*50 mL), washed with brine and dried (MgSO$_4$). The solvent was removed in vacuo to afford yellow liquid and purified the crude by flash column chromatography on a silica gel using dichloromethane as eluent. to afford 0.17 g of desired product (Rf=0.62). Mass spectrum (CI-NH$_3$): m/z 359 (M+H). 7–13–98: The above aldehyde (0.17 g) was dissolved in ethanol (15.0 mL) and treated with hydrazine (0.25 mL). The mixture was refluxed overnight and TLC (1:10 MeOH/CH$_2$Cl$_2$) revealed a new spot at Rf=0.49. The solvent was stripped off in vacuum and purified the crude by flash column chromatography on a silica gel using (1:50 MeOH/CH$_2$Cl$_2$) as eluent to afford 84 mg colorless oil. The oil was crystallized from 1:10 hexane/ether to afford 64 mg of white solid (mp 126–127° C.). HRMS calcd for C$_{20}$H$_{27}$N$_4$O$_2$: 355.2133. Found: 355.2121 (M+H).

Example 1124

4-(2,4-dichlorophenyl)-2-ethyl-1-(1-ethyl)propyl-7-methylimidazo[4,5-d]pyridazine Part A: 4-(2,4-dichlorobenzoyl)-2-ethyl-1-(1-ethyl)propyl-5-(1-hydroxyethyl)-1H-imidazole:

A mixture of Part E material of Example 1 (0.587 g, 0.0016 moles) in THF (20 mL) was cooled to −78° C. and then added dropwise 1.6 M MeLi in ether (1.0 mL, 0.0016 moles) over 5 mins. The mixture was stirred at −78° C. for 2 h and then quenched with water (5.0 ml) at −78° C. The reaction mixture was extracted with ethyl ether (3*30 mL), washed with brine and stripped off the solvent in vacuum to afford yellow liquid. TLC (30:70 EtOAc/hexane) showed absence of starting material at Rf=0.69 and a new spot at Rf=0.4. Purified the crude by flash column chromatography on a silica gel using 10% EtOAC/hexane to afford 0.470 g (77% yield) of desired product as white solid (mp 125–126° C.). Mass spectrum (CI-NH3): m/z=383 (M$^+$). Anal. calcd for C$_{19}$H$_{24}$Cl$_2$N$_2$O$_2$: C, 59.54; H, 6.31; N, 7.32. Found: C, 59.59; H, 6.28; N, 7.16.

Part B: 5-Acetyl-4-(2,4-dichlorobenzoyl)-2-ethyl-1-(1-ethyl)propyl-1H-imidazole

A solution of Part A material of Example 1124 (0.4 g, 0.00104 moles) in toluene(10 mL) was treated with MnO$_2$ (0.91 g, 0.0104 moles) and stirred at 75° C. for 40 h. TLC (30:70 EtOAc/hexane) showed presence of starting material at Rf=0.4 and a new spot at Rf=0.57. Added additional MnO$_2$ (0.91 g) and continued for additional 20 h at 75° C. &-27–98: TLC revealed only trace amount of starting material and therefore cooled the reaction mixture to 35 room temp and filtered through celite. The filterate was concentrated to afford 0.32 g of colorless oil and purified the crude by flash column chromatography on a silica gel using 15% EtOAC/hexane to afford 0.258 g (65% % yield) of desired product as white solid (m.p. 63–64° C.) Mass spec (CI-NH$_3$): m/z=381 (M$^+$). Anal. calcd. for C$_{19}$H$_{22}$Cl$_2$N$_2$O$_2$: C, 59.85; H, 5.83; N, 7.36. Found: C, 59.97; H, 5.80; N, 7.12.

Part C: Title Compound: imidazole

A solution of Part B material of Example 1124 (0.130 g, 0.00034 moles) in ethanol (10 mL) was treated with anhydrous hydrazine (0.142 g, 0.0044 moles) and refluxed under nitrogen for 3 h. TLC (1:10 MeOH/CH$_2$Cl$_2$) showed a new spot at Rf=0.55. The solvent was removed under vacuum and purified the crude by flash column chromatography on a silica gel using 50:50 EtOAc/hexane to afford 53 mg (41% yield) of the product as white solid after tituration of the oil with diethyl ether (mp 128–129° C.) Mass spectrum (CI-NH$_3$): m/z 377 (M$^+$). Anal. calcd. for C$_{19}$H$_{22}$Cl$_2$N$_4$: C, 60.48; H, 5.89; N, 14.89. Found: C, 59.40; H, 5.72; N, 14.46.

Example 1125

4-(2,4-dichlorophenyl)-2-ethyl-1-(1-ethyl)propyl-7-propoxyimidazo[4,5-d]pyridazine Part A: Methyl 4-(2,4-dichlorobenzoyl)-2-ethyl-1-(1-ethyl) propyl-1H-imidazole-5-carboxalate:

A mixture of Part E material of Example 1 (0.367 g, 0.001 moles) in methanol (60 mL) was treated with NaCN (Aldrich, 0.245 g, 0.005 moles, 5 equi.), AcOH (Baker, 96 mg; 0.0016 moles, 1.6 equiv.) and MnO$_2$, activated (Aldich, 1.24 g, 0.021 moles, 21 equiv.). The resulting mixture was stirred at room temp under nitrogen for 18 h. TLC (1:50 MeOH/CH$_2$Cl$_2$) revealed absence of starting material at Rf=0.8 and showed a new spot at Rf=0.44. Mass spec. revealed desired product (m/z=397). The reaction mixture was filtered through celite, washed with methanol, concentrated in vacuo and the crude was purified by flash column chromatography on a silica gel using 1:100 MeOH/CH$_2$Cl$_2$ as eluent to afford 320 mg (mp 73–74° C., 81%) of white solid after crystallization from hexane. Anal. calcd. for C$_{19}$H$_{22}$N$_2$O$_3$Cl$_2$: C, 57.44; H, 5.58; N, 7.05. Found: C, 57.31; H, 5.45; N, 6.85.

Part B: 4-(2,4-dichlorophenyl)-2-ethyl-1-(1-ethyl)propyl-imidazo[4,5-d]pyridazin-7-one:

A mixture of Part A material of example 1125 (0.100 g, 0.00025 moles) in ethanol (10 mL) was treated with anhydrous hydrazine (0.105 g, 0.0033 moles) and refluxed under nitrogen for 48 h. TLC (30:70 EtOAc/hexane) showed a new spot at Rf=0.35. The solvent was removed under vacuum and purified the crude by flash column chromatography on a silica gel using 15:50 EtOAc/hexane intially and then methanol to afford 70 mg (74% yield) of the product as white solid after tituration of the oil with diethyl ether (mp 246–247° C.). Mass spectrum (CI-$NH_3$) m/z=379 ($M^+$).

Part C: Title Compound:

A mixture of Part B material of example 1125 (0.1 g, 0.264 mmol) in benzene (5.0 mL) was treated with n-$Bu_4$NBr (8.5 mg, 0.0264 mmol), powdered KOH (15 mg, 0.264 mmol) and 1-iodopropane (0.134 g, 0.79 mmol). The mixture was stirred at room temp overnight and TLC (1:50 MeOH/$CH_2Cl_2$) showed two new spots at Rf=0.73 and Rf=0.46. The reaction mixture was diluted with EtOAc (10 mL), washed with brine (10 mL), dried with $MgSO_4$ and concentrated to a residue. The crude was purified by flash column chromatography on a silica gel using dichloromethane as eluent to afford 56 mg (51% yield) of the N-propyl product as colorless oil. Mass spectrum (CI-$NH_3$): m/z=421. Further elution of the column with 1:50 MeOH/$CH_2Cl_2$ gave 11 mg (10% yield) of oil which was crystallized from ether to afford 7-propoxy derivative as awhite solid (m.p. 120–121° C.). Mass spec. (CI-$NH_3$): m/z=421. HRMS calcd for $C_{21}H_{27}N_4OCl_2$: 421.1561. Found: 421.1569 (M+H).

Example 1126

7-chloro-4-(2,4-dichlorophenyl)-2-ethyl-1-(1-methyl)butyl-imidazo[4,5-d]pyridazine Part A: 4,5-dibromo-2-ethyl-1-(1-methyl)butyl-1H-imidazole:

A mixture of part A material of example 1 (59 g g, 0.233 moles), triphenylphosphine (67.1 g, 0.256 moles) and molecular sieves (10 g) in THF (715 mL) was cooled to 0 to −5° C. and then added 2-pentanol (34.79 g, 0.279 moles) under nitrogen atmosphere. The mixture was stirred at 0° C. for 30 mins and then added disopropylazodicarboxylate (50.33 g, 0.256 moles) dropwise over 20 mins. The mixture was stirred at 0° C. for 2 h followed by room temperature for 2 days and TLC (1:50 MeOH/$CH_2Cl_2$) revealed a new spot at Rf=0.5. The undissolved material was filtered, washed with dichloromethane and stripped off the solvent in vacuum to afford yellow liquid. The crude was purified by flash column chromatography using chloroform as eluent to afford 41.5 g (55%) of colorless oil. $^1$H NMR ($CDCl_3$): ? 0.91 (t, 3H, 2*$CH_3$), 1.27 (m, 2H, $CH_2$), 1.31 (t, 3H, $CH_3$), 1.53 (d, 3H, $CH_3$), 1.78 (m, 1H), 2.04 (m, 1H), 2.71 (q, 2H) and 4.34 (m,1H). Mass spectrum (CI-$NH_3$): m/z 325.0 (M+H).

Part B: 4-bromo-2-ethyl-1-(1-methyl)butyl-1H-imidazole-5-carboxaldehyde:

A solution of imidazole (37.5 g, 0.116 mol) in THF (250 mL) was cooled to −78° C. and then added dropwise 1.6 M n-BuLi(76 mL, 0. 122 mol) in hexane over 45 mins. The mixture was stirred at −78° C. for 1 h (brown solution) and then added DMF (27 g, 0.348 moles) dropwise over 30 mins. The mixture was stirred at −78° C. for 60 mins. The reaction mixture was quenched with satd. amm. chloride (100 mL) at −78° C. and brought to room temp. The reaction mixture was extracted with ethyl ether (3*100 mL), washed with brine and dried with anhyd. $MgSO_4$. The solvent was evaporated under reduced pressure to afford 31.6 g of crude yellow oil. The NMRof the crude revealed formation of 4-bromo-2-ethyl-1-(1-methyl)butyl-1H-imidazole along with desired product in the ratio of 3:7. The TLC of the undesired 4-bromo-2-ethyl-1-(1-methyl)butyl-1H-imidazole is visible under iodine exposure (Rf=0.45). The crude was purified by flash column chromatography on a silica gel using 1% MeOH to afford 18.5 g (59% yield) of colorless oil. Mass spec: m/z=273. Anal. calcd. for $C_{11}H_{17}N_2OBr$; C, 48.36; H. 6.27, N, 10.25. Found): C, 48.64; H, 6.01; N. 10.00.

Part C: 4-bromo-2-ethyl-1-(1-methyl)butyl-1H-imidazole-5-carboxaldehyde ethylene acetal:

A mixture of Part B material of example 1126 (18.5 g, 0.068 moles) in benzene (250 mL) was treated with ethylene glycol (16.4 g, 0.264 moles), pyridine (2.7 g, 0.034 moles) and p-toluenesulfonic acid monohydrate (6.5 g, 0.034 moles). The reaction mixture was heated at reflux in a 20 mL capacity Dean-Stark trap equipped apparatus for 36 h. TLC (30:70 EtOAc/hexane) revealed a new spot at Rf=0.42 (visible under iodine) along with trace amount of starting material (Rf=0.54). The reaction mixture was cooled to room temperature, diluted with EtOAc (250 mL), washed with 10% sodium bicarbonate (2*250 mL), brine and dried ($MgSO_4$). The solvent was evaporated under reduced pressure to furnish white solid (20.7 g, mp 69–70° C., 96%). The crude was very pure by NMR. Mass spectrum (CI-$NH_3$): m/z 317.1 ($M^+$). Anal. calcd. for $C_{13}H_{22}N_2O_2Br_1$; C, 49.22; H, 6.67, N, 8.83. Found: C, 49.38; H, 6.62; N, 8.68.

Part D: 4-(2,4-dichlorobenzoyl)-2-ethyl-1-(1-methyl)butyl-1H-imidazole-5-carboxaldehyde: A solution of Part C material of Example 1126 (2.3 g, 5.6 mmol) in acetone (60 mL) was cooled to 15° C. and then added 3M aq. HCl (120 mL) over 15 mins. The mixture was stirred below 30° C. for 24 h. TLC (30:70 EtOAc/hexane) showed a new spot at Rf=0.58 along with disappearance of starting material (Rf=0.43). The solvent was removed under vacuum, extracted with ethyl acetate (3*50 mL), washed with brine and stripped off the solvent in vacuum to afford yellow liquid (2.4 g). The crude was purified by flash column chromatography on a silica gel using dichloromethane as eluent to afford 1.46 g (71% yield) of desired product as yellow solid (mp 43–44° C.). Anal. calcd for $C_{18}H_{20}Cl_2N_2O_2$: C, 58.87; H, 5.50; N, 7.64. Found: C, 58.96; H, 5.34; N, 7.46. Mass spec. ($NH_3$-CI): m/z=367

Part E: Methyl 4-(2,4-dichlorobenzoyl)-2-ethyl-1-(1-methyl)butyl-1H-imidazole-5-carboxalate:

A mixture of Part D material of Example 1126 (1.0 g, 0.0027 moles) in methanol (50 mL) was treated with NaCN (Aldrich, 0.67 g, 0.0136 moles, 5 equi.), AcOH (Baker, 260 mg; 0.00432 moles, 1.6 equiv.) and $MnO_2$, activated (Aldrich, 3.34 g, 0.057 moles, 21 equiv.). The resulting mixture was stirred at room temp under nitrogen for 20 h. TLC (30:70 EtOAc/hexane) revealed absence of starting material at Rf=0.58 and showed a new spot at Rf=0.4. The reaction mixture was filtered through celite, washed with methanol, concentrated in vacuo. The residue was diluted with water, extracted with ethyl acetate, washed with brine, dried and concentrated in vacuo to afford 0.98 g of yellow oil. The crude was purified by flash column chromatography on a silica gel using 30:70 EtOAc/hexane as eluent to afford 910 mg (85%) of yellow oil. Mass spectrum : m/z=397. Anal. calcd. for $C_{19}H_{22}N_2O_3Cl_2$: C, 57.44; H, 5.58; N, 7.05. Found: C, 57.25; H, 5.70; N, 6.80.

Part F: 4-(2,4-dichlorophenyl)-2-ethyl-1-(1-ethyl)propyl-imidazo[4,5-d]pyridazin-7-one:

A mixture of Part E material of Example 1126 (0.460 g, 0.00115 moles) in ethylene glycol (5 mL) was treated with anhydrous hydrazine (0.48 g, 0.0151 moles) and refluxed under nitrogen for 4h. TLC (30:70 EtOAc/hexane) revealed a new spot (Rf=0.44) along with disappearence of starting material (Rf=0.4). The reaction mixture was cooled to room temp and poured over 25 mL of water, extracted with EtOAc (3*15 mL), washed with brine and dried. The solvent was removed under vacuo and purified the crude by flash column chromatography on a silica gel using 15% EtOAc/hexane to afford colorless oil which was crystallized from hexane to afford 310 mg of white solid (71%, mp 217–18° C.). Mass spec. (CI-NH$_3$): m/z=379. Anal. calcd. for $C_{18}H_{20}N_4Cl_2O$: C, 57.00; H, 5.33; N, 14.77. Found: C, 57.02; H, 5.35; N, 14.59.

Part G: Title Compound:

A mixture of Part F material of Example 1126 (0.270 g, 0.0071 moles) in POCl$_3$ (3.0 mL) was refluxed under nitrogen for 8 h. TLC (30:70 EtOAc/hexane) revealed a new spot (Rf=0.48) along with disappearence of starting material (Rf=0.44) Excess POCl$_3$ from the reaction mixture was removed under vacuo, quenched with ice (10 g), extracted with EtOAc (3*15 mL), washed with brine and dried. The solvent was removed under vacuo and purified the crude by flash column chromatography on a silica gel using 30% EtOAc/hexane to afford 80 mg of white solid (28%, mp 124–125° C.). HRMS calcd for $C_{18}H_{20}N_4Cl_3$: 397.0753. Found: 397.0749 (M+H).

Example 1127

4-(2,4-dichlorophenyl)-2-ethyl-1-(1-methyl)butyl-7-methoxy-imidazo[4,5-d]pyridazine A mixture of Part G material of Example 1126 (40 mg, 0.1 mmole) in MeOH (3.0 mL) was treated with 25% NaOMe in MeOH (0.065 mL, 0.3 mmole) and refluxed under nitrogen for 6 h. TLC (30:70 EtOAc/hexane) revealed a new spot (Rf=0.35) along with disappearance of starting material (Rf=0.48). The solvent from the reaction mixture was removed under vacuo, quenched with water (10 g), extracted with EtOAc (3*15 mL), washed with brine and dried. The solvent was removed under vacuo and purified the crude by recrystallizing from hexane to afford 36 mg of white solid (92%, mp 119–120° C.). HRMS calcd for $C_{19}H_{23}N_4Cl_3O_1$: 393.1248. Found: 393.1246 (M+H).

TABLE 1

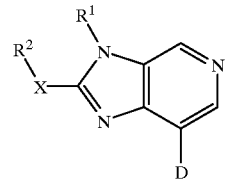

a$_1$ R$^2$X = CH$_3$O
a$_2$ R$^2$X = CH$_3$S
a$_3$ R$^2$X = Me
a$_4$ R$^2$X = Et
a$_5$ R$^2$X = n-Pr

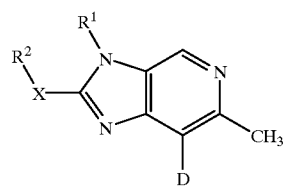

b$_1$ R$^2$X = CH$_3$O
b$_2$ R$^2$X = CH$_3$S
b$_3$ R$^2$X = Me
b$_4$ R$^2$X = Et
b$_5$ R$^2$X = n-Pr

TABLE 1-continued

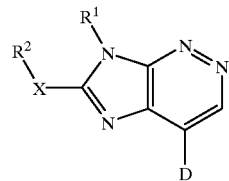

c$_1$ R$^2$X = CH$_3$O
c$_2$ R$^2$X = CH$_3$S
c$_3$ R$^2$X = Me
c$_4$ R$^2$X = Et
c$_5$ R$^2$X = n-Pr

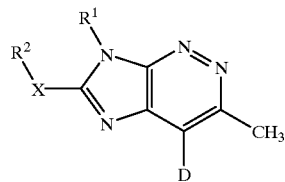

d$_1$ R$^2$X = CH$_3$O
d$_2$ R$^2$X = CH$_3$S
d$_3$ R$^2$X = Me
d$_4$ R$^2$X = Et
d$_5$ R$^2$X = n-Pr

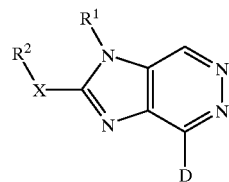

e$_1$ R$^2$X = CH$_3$O
e$_2$ R$^2$X = CH$_3$S
e$_3$ R$^2$X = Me
e$_4$ R$^2$X = Et
e$_5$ R$^2$X = n-Pr

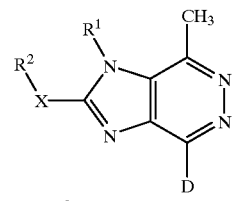

f$_1$ R$^2$X = CH$_3$O
f$_2$ R$^2$X = CH$_3$S
f$_3$ R$^2$X = Me
f$_4$ R$^2$X = Et
f$_5$ R$^2$X = n-Pr

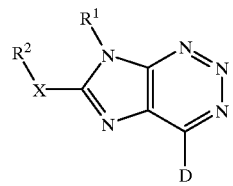

g$_1$ R$^2$X = CH$_3$O
g$_2$ R$^2$X = CH$_3$S
g$_3$ R$^2$X = Me
g$_4$ R$^2$X = Et
g$_5$ R$^2$X = n-Pr

Ex. # R$^1$            D

TABLE 1-continued

| | | |
|---|---|---|
| 1a | (cPr)₂CH | phenyl |
| 2 | phenyl(cPr)CH | phenyl |
| 3 | 2-furanyl(cPr)CH | phenyl |
| 4 | 3-furan(cPr)CH | phenyl |
| 5 | 2-thienyl(cPr)CH | phenyl |
| 6 | 3-thienyl(cPr)CH | phenyl |
| 7 | 2-isoxazolyl(cPr)CH | phenyl |
| 8 | 2-(5-CH₃-furanyl)(cPr)CH | phenyl |
| 9 | 2-(4-CH₃-isoxazolyl)(cPr)CH | phenyl |
| 10 | cPr—CH(CH₃) | phenyl |
| 11 | 1-cPr—CH(CH₂CH₃) | phenyl |
| 12 | 1-cPr—CH(CH₂CH₂CH₃) | phenyl |
| 13 | 1-cPr—CH(CH₂OCH₃) | phenyl |
| 14 | 1-cPr—CH(CH₂CH₂OCH₃) | phenyl |
| 15 | (cBu)₂CH | phenyl |
| 16 | phenyl(cBu)CH | phenyl |
| 17 | 2-furanyl(cBu)CH | phenyl |
| 18 | 3-furan(cBu)CH | phenyl |
| 19 | 2-thienyl(cBu)CH | phenyl |
| 20 | 3-thienyl(cBu)CH | phenyl |
| 21 | 2-isoxazolyl(cBu)CH | phenyl |
| 22 | 2-(5-CH₃-furanyl)(cBu)CH | phenyl |
| 23 | 2-(4-CH₃-isoxazolyl)(cBu)CH | phenyl |
| 24 | cBu—CH(CH₃) | phenyl |
| 25 | 1-cBu—CH(CH₂CH₃) | phenyl |
| 26 | 1-cBu—CH(CH₂CH₂CH₃) | phenyl |
| 27 | 1-cBu—CH(CH₂OCH₃) | phenyl |
| 28 | 1-cBu—CH(CH₂CH₂OCH₃) | phenyl |
| 29 | (cPr)₂CH | 2-Cl-4-MeO-phenyl |
| 30 | phenyl(cPr)CH | 2-Cl-4-MeO-phenyl |
| 31 | 2-furanyl(cPr)CH | 2-Cl-4-MeO-phenyl |
| 32 | 3-furan(cPr)CH | 2-Cl-4-MeO-phenyl |
| 33 | 2-thienyl(cPr)CH | 2-Cl-4-MeO-phenyl |
| 34 | 3-thienyl(cPr)CH | 2-Cl-4-MeO-phenyl |
| 35 | 2-isoxazolyl(cPr)CH | 2-Cl-4-MeO-phenyl |
| 36 | 2-(5-CH₃-furanyl)(cPr)CH | 2-Cl-4-MeO-phenyl |
| 37 | 2-(4-CH₃-isoxazolyl)(cPr)CH | 2-Cl-4-MeO-phenyl |
| 38 | cPr—CH(CH₃) | 2-Cl-4-MeO-phenyl |
| 39 | 1-cPr—CH(CH₂CH₃) | 2-Cl-4-MeO-phenyl |
| 40 | 1-cPr—CH(CH₂CH₂CH₃) | 2-Cl-4-MeO-phenyl |
| 41 | 1-cPr—CH(CH₂OCH₃) | 2-Cl-4-MeO-phenyl |
| 42 | 1-cPr—CH(CH₂CH₂OCH₃) | 2-Cl-4-MeO-phenyl |
| 43 | (cBu)₂CH | 2-Cl-4-MeO-phenyl |
| 44 | phenyl(cBu)CH | 2-Cl-4-MeO-phenyl |
| 45 | 2-furanyl(cBu)CH | 2-Cl-4-MeO-phenyl |
| 46 | 3-furan(cBu)CH | 2-Cl-4-MeO-phenyl |
| 47 | 2-thienyl(cBu)CH | 2-Cl-4-MeO-phenyl |
| 48 | 3-thienyl(cBu)CH | 2-Cl-4-MeO-phenyl |
| 49 | 2-isoxazolyl(cBu)CH | 2-Cl-4-MeO-phenyl |
| 50 | 2-(5-CH₃-furanyl)(cBu)CH | 2-Cl-4-MeO-phenyl |
| 51 | 2-(4-CH₃-isoxazolyl)(cBu)CH | 2-Cl-4-MeO-phenyl |
| 52 | cBu—CH(CH₃) | 2-Cl-4-MeO-phenyl |
| 53 | 1-cBu—CH(CH₂CH₃) | 2-Cl-4-MeO-phenyl |
| 54 | 1-cBu—CH(CH₂CH₂CH₃) | 2-Cl-4-MeO-phenyl |
| 55 | 1-cBu—CH(CH₂OCH₃) | 2-Cl-4-MeO-phenyl |
| 56 | 1-cBu—CH(CH₂CH₂OCH₃) | 2-Cl-4-MeO-phenyl |
| 57 | (cPr)₂CH | 2-Cl-4-CF₃-phenyl |
| 58 | phenyl(cPr)CH | 2-Cl-4-CF₃-phenyl |
| 59 | 2-furanyl(cPr)CH | 2-Cl-4-CF₃-phenyl |
| 60 | 3-furan(cPr)CH | 2-Cl-4-CF₃-phenyl |
| 61 | 2-thienyl(cPr)CH | 2-Cl-4-CF₃-phenyl |
| 62 | 3-thienyl(cPr)CH | 2-Cl-4-CF₃-phenyl |
| 63 | 2-isoxazolyl(cPr)CH | 2-Cl-4-CF₃-phenyl |
| 64 | 2-(5-CH₃-furanyl)(cPr)CH | 2-Cl-4-CF₃-phenyl |
| 65 | 2-(4-CH₃-isoxazolyl)(cPr)CH | 2-Cl-4-CF₃-phenyl |
| 66 | cPr—CH(CH₃) | 2-Cl-4-CF₃-phenyl |
| 67 | 1-cPr—CH(CH₂CH₃) | 2-Cl-4-CF₃-phenyl |
| 68 | 1-cPr—CH(CH₂CH₂CH₃) | 2-Cl-4-CF₃-phenyl |
| 69 | 1-cPr—CH(CH₂OCH₃) | 2-Cl-4-CF₃-phenyl |
| 70 | 1-cPr—CH(CH₂CH₂OCH₃) | 2-Cl-4-CF₃-phenyl |
| 71 | (cBu)₂CH | 2-Cl-4-CF₃-phenyl |
| 72 | phenyl(cBu)CH | 2-Cl-4-CF₃-phenyl |
| 73 | 2-furanyl(cBu)CH | 2-Cl-4-CF₃-phenyl |
| 74 | 3-furan(cBu)CH | 2-Cl-4-CF₃-phenyl |
| 75 | 2-thienyl(cBu)CH | 2-Cl-4-CF₃-phenyl |
| 76 | 3-thienyl(cBu)CH | 2-Cl-4-CF₃-phenyl |
| 77 | 2-isoxazolyl(cBu)CH | 2-Cl-4-CF₃-phenyl |
| 78 | 2-(5-CH₃-furanyl)(cBu)CH | 2-Cl-4-CF₃-phenyl |
| 79 | 2-(4-CH₃-isoxazolyl)(cBu)CH | 2-Cl-4-CF₃-phenyl |
| 80 | cBu—CH(CH₃) | 2-Cl-4-CF₃-phenyl |
| 81 | 1-cBu—CH(CH₂CH₃) | 2-Cl-4-CF₃-phenyl |
| 82 | 1-cBu—CH(CH₂CH₂CH₃) | 2-Cl-4-CF₃-phenyl |
| 83 | 1-cBu—CH(CH₂OCH₃) | 2-Cl-4-CF₃-phenyl |
| 84 | 1-cBu—CH(CH₂CH₂OCH₃) | 2-Cl-4-CF₃-phenyl |
| 85 | (cPr)₂CH | 2,4-diCl-phenyl |
| 86 | phenyl(cPr)CH | 2,4-diCl-phenyl |
| 87 | 2-furanyl(cPr)CH | 2,4-diCl-phenyl |
| 88 | 3-furan(cPr)CH | 2,4-diCl-phenyl |
| 89 | 2-thienyl(cPr)CH | 2,4-diCl-phenyl |
| 90 | 3-thienyl(cPr)CH | 2,4-diCl-phenyl |
| 91 | 2-isoxazolyl(cPr)CH | 2,4-diCl-phenyl |
| 92 | 2-(5-CH₃-furanyl)(cPr)CH | 2,4-diCl-phenyl |
| 93 | 2-(4-CH₃-isoxazolyl)(cPr)CH | 2,4-diCl-phenyl |
| 94 | cPr—CH(CH₃) | 2,4-diCl-phenyl |
| 95 | 1-cPr—CH(CH₂CH₃) | 2,4-diCl-phenyl |
| 96 | 1-cPr—CH(CH₂CH₂CH₃) | 2,4-diCl-phenyl |
| 97 | 1-cPr—CH(CH₂OCH₃) | 2,4-diCl-phenyl |
| 98 | 1-cPr—CH(CH₂CH₂OCH₃) | 2,4-diCl-phenyl |
| 99 | (cBu)₂CH | 2,4-diCl-phenyl |
| 100 | phenyl(cBu)CH | 2,4-diCl-phenyl |
| 101 | 2-furanyl(cBu)CH | 2,4-diCl-phenyl |
| 102 | 3-furan(cBu)CH | 2,4-diCl-phenyl |
| 103 | 2-thienyl(cBu)CH | 2,4-diCl-phenyl |
| 104 | 3-thienyl(cBu)CH | 2,4-diCl-phenyl |
| 105 | 2-isoxazolyl(cBu)CH | 2,4-diCl-phenyl |
| 106 | 2-(5-CH₃-furanyl)(cBu)CH | 2,4-diCl-phenyl |
| 107 | 2-(4-CH₃-isoxazolyl)(cBu)CH | 2,4-diCl-phenyl |
| 108 | cBu—CH(CH₃) | 2,4-diCl-phenyl |
| 109 | 1-cBu—CH(CH₂CH₃) | 2,4-diCl-phenyl |
| 110 | 1-cBu—CH(CH₂CH₂CH₃) | 2,4-diCl-phenyl |
| 111 | 1-cBu—CH(CH₂OCH₃) | 2,4-diCl-phenyl |
| 112 | 1-cBu—CH(CH₂CH₂OCH₃) | 2,4-diCl-phenyl |
| 113 | (cPr)₂CH | 2,5-diCl-phenyl |
| 114 | phenyl(cPr)CH | 2,5-diCl-phenyl |
| 115 | 2-furanyl(cPr)CH | 2,5-diCl-phenyl |
| 116 | 3-furan(cPr)CH | 2,5-diCl-phenyl |
| 117 | 2-thienyl(cPr)CH | 2,5-diCl-phenyl |
| 118 | 3-thienyl(cPr)CH | 2,5-diCl-phenyl |
| 119 | 2-isoxazolyl(cPr)CH | 2,5-diCl-phenyl |
| 120 | 2-(5-CH₃-furanyl)(cPr)CH | 2,5-diCl-phenyl |
| 121 | 2-(4-CH₃-isoxazolyl)(cPr)CH | 2,5-diCl-phenyl |
| 122 | cPr—CH(CH₃) | 2,5-diCl-phenyl |
| 123 | 1-cPr—CH(CH₂CH₃) | 2,5-diCl-phenyl |
| 124 | 1-cPr—CH(CH₂CH₂CH₃) | 2,5-diCl-phenyl |
| 125 | 1-cPr—CH(CH₂OCH₃) | 2,5-diCl-phenyl |
| 126 | 1-cPr—CH(CH₂CH₂OCH₃) | 2,5-diCl-phenyl |
| 127 | (cBu)₂CH | 2,5-diCl-phenyl |
| 128 | phenyl(cBu)CH | 2,5-diCl-phenyl |
| 129 | 2-furanyl(cBu)CH | 2,5-diCl-phenyl |
| 130 | 3-furan(cBu)CH | 2,5-diCl-phenyl |
| 131 | 2-thienyl(cBu)CH | 2,5-diCl-phenyl |
| 132 | 3-thienyl(cBu)CH | 2,5-diCl-phenyl |
| 133 | 2-isoxazolyl(cBu)CH | 2,5-diCl-phenyl |
| 134 | 2-(5-CH₃-furanyl)(cBu)CH | 2,5-diCl-phenyl |
| 135 | 2-(4-CH₃-isoxazolyl)(cBu)CH | 2,5-diCl-phenyl |
| 136 | cBu—CH(CH₃) | 2,5-diCl-phenyl |
| 137 | 1-cBu—CH(CH₂CH₃) | 2,5-diCl-phenyl |
| 138 | 1-cBu—CH(CH₂CH₂CH₃) | 2,5-diCl-phenyl |
| 139 | 1-cBu—CH(CH₂OCH₃) | 2,5-diCl-phenyl |
| 140 | 1-cBu—CH(CH₂CH₂OCH₃) | 2,5-diCl-phenyl |
| 141 | (cPr)₂CH | 2-Cl-4-CF₃O-phenyl |
| 142 | phenyl(cPr)CH | 2-Cl-4-CF₃O-phenyl |
| 143 | 2-furanyl(cPr)CH | 2-Cl-4-CF₃O-phenyl |
| 144 | 3-furan(cPr)CH | 2-Cl-4-CF₃O-phenyl |
| 145 | 2-thienyl(cPr)CH | 2-Cl-4-CF₃O-phenyl |
| 146 | 3-thienyl(cPr)CH | 2-Cl-4-CF₃O-phenyl |
| 147 | 2-isoxazolyl(cPr)CH | 2-Cl-4-CF₃O-phenyl |
| 148 | 2-(5-CH₃-furanyl)(cPr)CH | 2-Cl-4-CF₃O-phenyl |
| 149 | 2-(4-CH₃-isoxazolyl)(cPr)CH | 2-Cl-4-CF₃O-phenyl |
| 150 | cPr—CH(CH₃) | 2-Cl-4-CF₃O-phenyl |
| 151 | 1-cPr—CH(CH₂CH₃) | 2-Cl-4-CF₃O-phenyl |
| 152 | 1-cPr—CH(CH₂CH₂CH₃) | 2-Cl-4-CF₃O-phenyl |
| 153 | 1-cPr—CH(CH₂OCH₃) | 2-Cl-4-CF₃O-phenyl |
| 154 | 1-cPr—CH(CH₂CH₂OCH₃) | 2-Cl-4-CF₃O-phenyl |
| 155 | (cBu)₂CH | 2-Cl-4-CF₃O-phenyl |
| 156 | phenyl(cBu)CH | 2-Cl-4-CF₃O-phenyl |
| 157 | 2-furanyl(cBu)CH | 2-Cl-4-CF₃O-phenyl |
| 158 | 3-furan(cBu)CH | 2-Cl-4-CF₃O-phenyl |

TABLE 1-continued

| | | |
|---|---|---|
| 159 | 2-thienyl(cBu)CH | 2-Cl-4-CF$_3$O-phenyl |
| 160 | 3-thienyl(cBu)CH | 2-Cl-4-CF$_3$O-phenyl |
| 161 | 2-isoxazolyl(cBu)CH | 2-Cl-4-CF$_3$O-phenyl |
| 162 | 2-(5-CH$_3$-furanyl)(cBu)CH | 2-Cl-4-CF$_3$O-phenyl |
| 163 | 2-(4-CH$_3$-isoxazolyl)(cBu)CH | 2-Cl-4-CF$_3$O-phenyl |
| 164 | cBu—CH(CH$_3$) | 2-Cl-4-CF$_3$O-phenyl |
| 165 | 1-cBu—CH(CH$_2$CH$_3$) | 2-Cl-4-CF$_3$O-phenyl |
| 166 | 1-cBu—CH(CH$_2$CH$_2$CH$_3$) | 2-Cl-4-CF$_3$O-phenyl |
| 167 | 1-cBu—CH(CH$_2$OCH$_3$) | 2-Cl-4-CF$_3$O-phenyl |
| 168 | 1-cBu—CH(CH$_2$CH$_2$OCH$_3$) | 2-Cl-4-CF$_3$O-phenyl |
| 169 | (cPr)$_2$CH | 2-Cl-4-CH$_3$-phenyl |
| 170 | phenyl(cPr)CH | 2-Cl-4-CH$_3$-phenyl |
| 171 | 2-furanyl(cPr)CH | 2-Cl-4-CH$_3$-phenyl |
| 172 | 3-furan(cPr)CH | 2-Cl-4-CH$_3$-phenyl |
| 173 | 2-thienyl(cPr)CH | 2-Cl-4-CH$_3$-phenyl |
| 174 | 3-thienyl(cPr)CH | 2-Cl-4-CH$_3$-phenyl |
| 175 | 2-isoxazolyl(cPr)CH | 2-Cl-4-CH$_3$-phenyl |
| 176 | 2-(5-CH$_3$-furanyl)(cPr)CH | 2-Cl-4-CH$_3$-phenyl |
| 177 | 2-(4-CH$_3$-isoxazolyl)(cPr)CH | 2-Cl-4-CH$_3$-phenyl |
| 178 | cPr—CH(CH$_3$) | 2-Cl-4-CH$_3$-phenyl |
| 179 | 1-cPr—CH(CH$_2$CH$_3$) | 2-Cl-4-CH$_3$-phenyl |
| 180 | 1-cPr—CH(CH$_2$CH$_2$CH$_3$) | 2-Cl-4-CH$_3$-phenyl |
| 181 | 1-cPr—CH(CH$_2$OCH$_3$) | 2-Cl-4-CH$_3$-phenyl |
| 182 | 1-cPr—CH(CH$_2$CH$_2$OCH$_3$) | 2-Cl-4-CH$_3$-phenyl |
| 183 | (cBu)$_2$CH | 2-Cl-4-CH$_3$-phenyl |
| 184 | phenyl(cBu)CH | 2-Cl-4-CH$_3$-phenyl |
| 185 | 2-furanyl(cBu)CH | 2-Cl-4-CH$_3$-phenyl |
| 186 | 3-furan(cBu)CH | 2-Cl-4-CH$_3$-phenyl |
| 187 | 2-thienyl(cBu)CH | 2-Cl-4-CH$_3$-phenyl |
| 188 | 3-thienyl(cBu)CH | 2-Cl-4-CH$_3$-phenyl |
| 189 | 2-isoxazolyl(cBu)CH | 2-Cl-4-CH$_3$-phenyl |
| 190 | 2-(5-CH$_3$-furanyl)(cBu)CH | 2-Cl-4-CH$_3$-phenyl |
| 191 | 2-(4-CH$_3$-isoxazolyl)(cBu)CH | 2-Cl-4-CH$_3$-phenyl |
| 192 | cBu—CH(CH$_3$) | 2-Cl-4-CH$_3$-phenyl |
| 193 | 1-cBu—CH(CH$_2$CH$_3$) | 2-Cl-4-CH$_3$-phenyl |
| 194 | 1-cBu—CH(CH$_2$CH$_2$CH$_3$) | 2-Cl-4-CH$_3$-phenyl |
| 195 | 1-cBu—CH(CH$_2$OCH$_3$) | 2-Cl-4-CH$_3$-phenyl |
| 196 | 1-cBu—CH(CH$_2$CH$_2$OCH$_3$) | 2-Cl-4-CH$_3$-phenyl |
| 197 | (cPr)$_2$CH | 2-Cl-4-CN-phenyl |
| 198 | phenyl(cPr)CH | 2-Cl-4-CN-phenyl |
| 199 | 2-furanyl(cPr)CH | 2-Cl-4-CN-phenyl |
| 200 | 3-furan(cPr)CH | 2-Cl-4-CN-phenyl |
| 201 | 2-thienyl(cPr)CH | 2-Cl-4-CN-phenyl |
| 202 | 3-thienyl(cPr)CH | 2-Cl-4-CN-phenyl |
| 203 | 2-isoxazolyl(cPr)CH | 2-Cl-4-CN-phenyl |
| 204 | 2-(5-CH$_3$-furanyl)(cPr)CH | 2-Cl-4-CN-phenyl |
| 205 | 2-(4-CH$_3$-isoxazolyl)(cPr)CH | 2-Cl-4-CN-phenyl |
| 206 | cPr—CH(CH$_3$) | 2-Cl-4-CN-phenyl |
| 207 | 1-cPr—CH(CH$_2$CH$_3$) | 2-Cl-4-CN-phenyl |
| 208 | 1-cPr—CH(CH$_2$CH$_2$CH$_3$) | 2-Cl-4-CN-phenyl |
| 209 | 1-cPr—CH(CH$_2$OCH$_3$) | 2-Cl-4-CN-phenyl |
| 210 | 1-cPr—CH(CH$_2$CH$_2$OCH$_3$) | 2-Cl-4-CN-phenyl |
| 211 | (cBu)$_2$CH | 2-Cl-4-CN-phenyl |
| 212 | phenyl(cBu)CH | 2-Cl-4-CN-phenyl |
| 213 | 2-furanyl(cBu)CH | 2-Cl-4-CN-phenyl |
| 214 | 3-furan(cBu)CH | 2-Cl-4-CN-phenyl |
| 215 | 2-thienyl(cBu)CH | 2-Cl-4-CN-phenyl |
| 216 | 3-thienyl(cBu)CH | 2-Cl-4-CN-phenyl |
| 217 | 2-isoxazolyl(cBu)CH | 2-Cl-4-CN-phenyl |
| 218 | 2-(5-CH$_3$-furanyl)(cBu)CH | 2-Cl-4-CN-phenyl |
| 219 | 2-(4-CH$_3$-isoxazolyl)(cBu)CH | 2-Cl-4-CN-phenyl |
| 220 | cBu—CH(CH$_3$) | 2-Cl-4-CN-phenyl |
| 221 | 1-cBu—CH(CH$_2$CH$_3$) | 2-Cl-4-CN-phenyl |
| 222 | 1-cBu—CH(CH$_2$CH$_2$CH$_3$) | 2-Cl-4-CN-phenyl |
| 223 | 1-cBu—CH(CH$_2$OCH$_3$) | 2-Cl-4-CN-phenyl |
| 224 | 1-cBu—CH(CH$_2$CH$_2$OCH$_3$) | 2-Cl-4-CN-phenyl |
| 225 | (cPr)$_2$CH | 2-CF$_3$-4-Cl-phenyl |
| 226 | phenyl(cPr)CH | 2-CF$_3$-4-Cl-phenyl |
| 227 | 2-furanyl(cPr)CH | 2-CF$_3$-4-Cl-phenyl |
| 228 | 3-furan(cPr)CH | 2-CF$_3$-4-Cl-phenyl |
| 229 | 2-thienyl(cPr)CH | 2-CF$_3$-4-Cl-phenyl |
| 230 | 3-thienyl(cPr)CH | 2-CF$_3$-4-Cl-phenyl |
| 231 | 2-isoxazolyl(cPr)CH | 2-CF$_3$-4-Cl-phenyl |
| 232 | 2-(5-CH$_3$-furanyl)(cPr)CH | 2-CF$_3$-4-Cl-phenyl |
| 233 | 2-(4-CH$_3$-isoxazolyl)(cPr)CH | 2-CF$_3$-4-Cl-phenyl |
| 234 | cPr—CH(CH$_3$) | 2-CF$_3$-4-Cl-phenyl |
| 235 | 1-cPr—CH(CH$_2$CH$_3$) | 2-CF$_3$-4-Cl-phenyl |
| 236 | 1-cPr—CH(CH$_2$CH$_2$CH$_3$) | 2-CF$_3$-4-Cl-phenyl |
| 237 | 1-cPr—CH(CH$_2$OCH$_3$) | 2-CF$_3$-4-Cl-phenyl |
| 238 | 1-cPr—CH(CH$_2$CH$_2$OCH$_3$) | 2-CF$_3$-4-Cl-phenyl |
| 239 | (cBu)$_2$CH | 2-CF$_3$-4-Cl-phenyl |
| 240 | phenyl(cBu)CH | 2-CF$_3$-4-Cl-phenyl |
| 241 | 2-furanyl(cBu)CH | 2-CF$_3$-4-Cl-phenyl |
| 242 | 3-furan(cBu)CH | 2-CF$_3$-4-Cl-phenyl |
| 243 | 2-thienyl(cBu)CH | 2-CF$_3$-4-Cl-phenyl |
| 244 | 3-thienyl(cBu)CH | 2-CF$_3$-4-Cl-phenyl |
| 245 | 2-isoxazolyl(cBu)CH | 2-CF$_3$-4-Cl-phenyl |
| 246 | 2-(5-CH$_3$-furanyl)(cBu)CH | 2-CF$_3$-4-Cl-phenyl |
| 247 | 2-(4-CH$_3$-isoxazolyl)(cBu)CH | 2-CF$_3$-4-Cl-phenyl |
| 248 | cBu—CH(CH$_3$) | 2-CF$_3$-4-Cl-phenyl |
| 249 | 1-cBu—CH(CH$_2$CH$_3$) | 2-CF$_3$-4-Cl-phenyl |
| 250 | 1-cBu—CH(CH$_2$CH$_2$CH$_3$) | 2-CF$_3$-4-Cl-phenyl |
| 251 | 1-cBu—CH(CH$_2$OCH$_3$) | 2-CF$_3$-4-Cl-phenyl |
| 252 | 1-cBu—CH(CH$_2$CH$_2$OCH$_3$) | 2-CF$_3$-4-Cl-phenyl |
| 253 | (cPr)$_2$CH | 2-CF$_3$-4-MeO-phenyl |
| 254 | phenyl(cPr)CH | 2-CF$_3$-4-MeO-phenyl |
| 255 | 2-furanyl(cPr)CH | 2-CF$_3$-4-MeO-phenyl |
| 256 | 3-furan(cPr)CH | 2-CF$_3$-4-MeO-phenyl |
| 257 | 2-thienyl(cPr)CH | 2-CF$_3$-4-MeO-phenyl |
| 258 | 3-thienyl(cPr)CH | 2-CF$_3$-4-MeO-phenyl |
| 259 | 2-isoxazolyl(cPr)CH | 2-CF$_3$-4-MeO-phenyl |
| 260 | 2-(5-CH$_3$-furanyl)(cPr)CH | 2-CF$_3$-4-MeO-phenyl |
| 261 | 2-(4-CH$_3$-isoxazolyl)(cPr)CH | 2-CF$_3$-4-MeO-phenyl |
| 262 | cPr—CH(CH$_3$) | 2-CF$_3$-4-MeO-phenyl |
| 263 | 1-cPr—CH(CH$_2$CH$_3$) | 2-CF$_3$-4-MeO-phenyl |
| 264 | 1-cPr—CH(CH$_2$CH$_2$CH$_3$) | 2-CF$_3$-4-MeO-phenyl |
| 265 | 1-cPr—CH(CH$_2$OCH$_3$) | 2-CF$_3$-4-MeO-phenyl |
| 266 | 1-cPr—CH(CH$_2$CH$_2$OCH$_3$) | 2-CF$_3$-4-MeO-phenyl |
| 267 | (cBu)$_2$CH | 2-CF$_3$-4-MeO-phenyl |
| 268 | phenyl(cBu)CH | 2-CF$_3$-4-MeO-phenyl |
| 269 | 2-furanyl(cBu)CH | 2-CF$_3$-4-MeO-phenyl |
| 270 | 3-furan(cBu)CH | 2-CF$_3$-4-MeO-phenyl |
| 271 | 2-thienyl(cBu)CH | 2-CF$_3$-4-MeO-phenyl |
| 272 | 3-thienyl(cBu)CH | 2-CF$_3$-4-MeO-phenyl |
| 273 | 2-isoxazolyl(cBu)CH | 2-CF$_3$-4-MeO-phenyl |
| 274 | 2-(5-CH$_3$-furanyl)(cBu)CH | 2-CF$_3$-4-MeO-phenyl |
| 275 | 2-(4-CH$_3$-isoxazolyl)(cBu)CH | 2-CF$_3$-4-MeO-phenyl |
| 276 | cBu—CH(CH$_3$) | 2-CF$_3$-4-MeO-phenyl |
| 277 | 1-cBu—CH(CH$_2$CH$_3$) | 2-CF$_3$-4-MeO-phenyl |
| 278 | 1-cBu—CH(CH$_2$CH$_2$CH$_3$) | 2-CF$_3$-4-MeO-phenyl |
| 279 | 1-cBu—CH(CH$_2$OCH$_3$) | 2-CF$_3$-4-MeO-phenyl |
| 280 | 1-cBu—CH(CH$_2$CH$_2$OCH$_3$) | 2-CF$_3$-4-MeO-phenyl |
| 281 | (cPr)$_2$CH | 2-CF$_3$-4-n-PrO-phenyl |
| 282 | phenyl(cPr)CH | 2-CF$_3$-4-n-PrO-phenyl |
| 283 | 2-furanyl(cPr)CH | 2-CF$_3$-4-n-PrO-phenyl |
| 284 | 3-furan(cPr)CH | 2-CF$_3$-4-n-PrO-phenyl |
| 285 | 2-thienyl(cPr)CH | 2-CF$_3$-4-n-PrO-phenyl |
| 286 | 3-thienyl(cPr)CH | 2-CF$_3$-4-n-PrO-phenyl |
| 287 | 2-isoxazolyl(cPr)CH | 2-CF$_3$-4-n-PrO-phenyl |
| 288 | 2-(5-CH$_3$-furanyl)(cPr)CH | 2-CF$_3$-4-n-PrO-phenyl |
| 289 | 2-(4-CH$_3$-isoxazolyl)(cPr)CH | 2-CF$_3$-4-n-PrO-phenyl |
| 290 | cPr—CH(CH$_3$) | 2-CF$_3$-4-n-PrO-phenyl |
| 291 | 1-cPr—CH(CH$_2$CH$_3$) | 2-CF$_3$-4-n-PrO-phenyl |
| 292 | 1-cPr—CH(CH$_2$CH$_2$CH$_3$) | 2-CF$_3$-4-n-PrO-phenyl |
| 293 | 1-cPr—CH(CH$_2$OCH$_3$) | 2-CF$_3$-4-n-PrO-phenyl |
| 294 | 1-cPr—CH(CH$_2$CH$_2$OCH$_3$) | 2-CF$_3$-4-n-PrO-phenyl |
| 295 | (cBu)$_2$CH | 2-CF$_3$-4-n-PrO-phenyl |
| 296 | phenyl(cBu)CH | 2-CF$_3$-4-n-PrO-phenyl |
| 297 | 2-furanyl(cBu)CH | 2-CF$_3$-4-n-PrO-phenyl |
| 298 | 3-furan(cBu)CH | 2-CF$_3$-4-n-PrO-phenyl |
| 299 | 2-thienyl(cBu)CH | 2-CF$_3$-4-n-PrO-phenyl |
| 300 | 3-thienyl(cBu)CH | 2-CF$_3$-4-n-PrO-phenyl |
| 301 | 2-isoxazolyl(cBu)CH | 2-CF$_3$-4-n-PrO-phenyl |
| 302 | 2-(5-CH$_3$-furanyl)(cBu)CH | 2-CF$_3$-4-n-PrO-phenyl |
| 303 | 2-(4-CH$_3$-isoxazolyl)(cBu)CH | 2-CF$_3$-4-n-PrO-phenyl |
| 304 | cBu—CH(CH$_3$) | 2-CF$_3$-4-n-PrO-phenyl |
| 305 | 1-cBu—CH(CH$_2$CH$_3$) | 2-CF$_3$-4-n-PrO-phenyl |
| 306 | 1-cBu—CH(CH$_2$CH$_2$CH$_3$) | 2-CF$_3$-4-n-PrO-phenyl |
| 307 | 1-cBu—CH(CH$_2$OCH$_3$) | 2-CF$_3$-4-n-PrO-phenyl |
| 308 | 1-cBu—CH(CH$_2$CH$_2$OCH$_3$) | 2-CF$_3$-4-n-PrO-phenyl |
| 309 | (cPr)$_2$CH | 2,4-diCF$_3$-phenyl |
| 310 | phenyl(cPr)CH | 2,4-diCF$_3$-phenyl |
| 311 | 2-furanyl(cPr)CH | 2,4-diCF$_3$-phenyl |
| 312 | 3-furan(cPr)CH | 2,4-diCF$_3$-phenyl |
| 313 | 2-thienyl(cPr)CH | 2,4-diCF$_3$-phenyl |
| 314 | 3-thienyl(cPr)CH | 2,4-diCF$_3$-phenyl |
| 315 | 2-isoxazolyl(cPr)CH | 2,4-diCF$_3$-phenyl |
| 316 | 2-(5-CH$_3$-furanyl)(cPr)CH | 2,4-diCF$_3$-phenyl |

TABLE 1-continued

| | | |
|---|---|---|
| 317 | 2-(4-CH$_3$-isoxazolyl)(cPr)CH | 2,4-diCF$_3$-phenyl |
| 318 | cPr—CH(CH$_3$) | 2,4-diCF$_3$-phenyl |
| 319 | 1-cPr—CH(CH$_2$CH$_3$) | 2,4-diCF$_3$-phenyl |
| 320 | 1-cPr—CH(CH$_2$CH$_2$CH$_3$) | 2,4-diCF$_3$-phenyl |
| 321 | 1-cPr—CH(CH$_2$OCH$_3$) | 2,4-diCF$_3$-phenyl |
| 322 | 1-cPr—CH(CH$_2$CH$_2$OCH$_3$) | 2,4-diCF$_3$-phenyl |
| 323 | (cBu)$_2$CH | 2,4-diCF$_3$-phenyl |
| 324 | phenyl(cBu)CH | 2,4-diCF$_3$-phenyl |
| 325 | 2-furanyl(cBu)CH | 2,4-diCF$_3$-phenyl |
| 326 | 3-furan(cBu)CH | 2,4-diCF$_3$-phenyl |
| 327 | 2-thienyl(cBu)CH | 2,4-diCF$_3$-phenyl |
| 328 | 3-thienyl(cBu)CH | 2,4-diCF$_3$-phenyl |
| 329 | 2-isoxazolyl(cBu)CH | 2,4-diCF$_3$-phenyl |
| 330 | 2-(5-CH$_3$-furanyl)(cBu)CH | 2,4-diCF$_3$-phenyl |
| 331 | 2-(4-CH$_3$-isoxazolyl)(cBu)CH | 2,4-diCF$_3$-phenyl |
| 332 | cBu—CH(CH$_3$) | 2,4-diCF$_3$-phenyl |
| 333 | 1-cBu—CH(CH$_2$CH$_3$) | 2,4-diCF$_3$-phenyl |
| 334 | 1-cBu—CH(CH$_2$CH$_2$CH$_3$) | 2,4-diCF$_3$-phenyl |
| 335 | 1-cBu—CH(CH$_2$OCH$_3$) | 2,4-diCF$_3$-phenyl |
| 336 | 1-cBu—CH(CH$_2$CH$_2$OCH$_3$) | 2,4-diCF$_3$-phenyl |
| 337 | (cPr)$_2$CH | 2-CF$_3$-4-F-phenyl |
| 338 | phenyl(cPr)CH | 2-CF$_3$-4-F-phenyl |
| 339 | 2-furanyl(cPr)CH | 2-CF$_3$-4-F-phenyl |
| 340 | 3-furan(cPr)CH | 2-CF$_3$-4-F-phenyl |
| 341 | 2-thienyl(cPr)CH | 2-CF$_3$-4-F-phenyl |
| 342 | 3-thienyl(cPr)CH | 2-CF$_3$-4-F-phenyl |
| 343 | 2-isoxazolyl(cPr)CH | 2-CF$_3$-4-F-phenyl |
| 344 | 2-(5-CH$_3$-furanyl)(cPr)CH | 2-CF$_3$-4-F-phenyl |
| 345 | 2-(4-CH$_3$-isoxazolyl)(cPr)CH | 2-CF$_3$-4-F-phenyl |
| 346 | cPr—CH(CH$_3$) | 2-CF$_3$-4-F-phenyl |
| 347 | 1-cPr—CH(CH$_2$CH$_3$) | 2-CF$_3$-4-F-phenyl |
| 348 | 1-cPr—CH(CH$_2$CH$_2$CH$_3$) | 2-CF$_3$-4-F-phenyl |
| 349 | 1-cPr—CH(CH$_2$OCH$_3$) | 2-CF$_3$-4-F-phenyl |
| 350 | 1-cPr—CH(CH$_2$CH$_2$OCH$_3$) | 2-CF$_3$-4-F-phenyl |
| 351 | (cBu)$_2$CH | 2-CF$_3$-4-F-phenyl |
| 352 | phenyl(cBu)CH | 2-CF$_3$-4-F-phenyl |
| 353 | 2-furanyl(cBu)CH | 2-CF$_3$-4-F-phenyl |
| 354 | 3-furan(cBu)CH | 2-CF$_3$-4-F-phenyl |
| 355 | 2-thienyl(cBu)CH | 2-CF$_3$-4-F-phenyl |
| 356 | 3-thienyl(cBu)CH | 2-CF$_3$-4-F-phenyl |
| 357 | 2-isoxazolyl(cBu)CH | 2-CF$_3$-4-F-phenyl |
| 358 | 2-(5-CH$_3$-furanyl)(cBu)CH | 2-CF$_3$-4-F-phenyl |
| 359 | 2-(4-CH$_3$-isoxazolyl)(cBu)CH | 2-CF$_3$-4-F-phenyl |
| 360 | cBu—CH(CH$_3$) | 2-CF$_3$-4-F-phenyl |
| 361 | 1-cBu—CH(CH$_2$CH$_3$) | 2-CF$_3$-4-F-phenyl |
| 362 | 1-cBu—CH(CH$_2$CH$_2$CH$_3$) | 2-CF$_3$-4-F-phenyl |
| 363 | 1-cBu—CH(CH$_2$OCH$_3$) | 2-CF$_3$-4-F-phenyl |
| 364 | 1-cBu—CH(CH$_2$CH$_2$OCH$_3$) | 2-CF$_3$-4-F-phenyl |
| 365 | (cPr)$_2$CH | 2-CH$_3$-4-Cl-phenyl |
| 366 | phenyl(cPr)CH | 2-CH$_3$-4-Cl-phenyl |
| 367 | 2-furanyl(cPr)CH | 2-CH$_3$-4-Cl-phenyl |
| 368 | 3-furan(cPr)CH | 2-CH$_3$-4-Cl-phenyl |
| 369 | 2-thienyl(cPr)CH | 2-CH$_3$-4-Cl-phenyl |
| 370 | 3-thienyl(cPr)CH | 2-CH$_3$-4-Cl-phenyl |
| 371 | 2-isoxazolyl(cPr)CH | 2-CH$_3$-4-Cl-phenyl |
| 372 | 2-(5-CH$_3$-furanyl)(cPr)CH | 2-CH$_3$-4-Cl-phenyl |
| 373 | 2-(4-CH$_3$-isoxazolyl)(cPr)CH | 2-CH$_3$-4-Cl-phenyl |
| 374 | cPr—CH(CH$_3$) | 2-CH$_3$-4-Cl-phenyl |
| 375 | 1-cPr—CH(CH$_2$CH$_3$) | 2-CH$_3$-4-Cl-phenyl |
| 376 | 1-cPr—CH(CH$_2$CH$_2$CH$_3$) | 2-CH$_3$-4-Cl-phenyl |
| 377 | 1-cPr—CH(CH$_2$OCH$_3$) | 2-CH$_3$-4-Cl-phenyl |
| 378 | 1-cPr—CH(CH$_2$CH$_2$OCH$_3$) | 2-CH$_3$-4-Cl-phenyl |
| 379 | (cBu)$_2$CH | 2-CH$_3$-4-Cl-phenyl |
| 380 | phenyl(cBu)CH | 2-CH$_3$-4-Cl-phenyl |
| 381 | 2-furanyl(cBu)CH | 2-CH$_3$-4-Cl-phenyl |
| 382 | 3-furan(cBu)CH | 2-CH$_3$-4-Cl-phenyl |
| 383 | 2-thienyl(cBu)CH | 2-CH$_3$-4-Cl-phenyl |
| 384 | 3-thienyl(cBu)CH | 2-CH$_3$-4-Cl-phenyl |
| 385 | 2-isoxazolyl(cBu)CH | 2-CH$_3$-4-Cl-phenyl |
| 386 | 2-(5-CH$_3$-furanyl)(cBu)CH | 2-CH$_3$-4-Cl-phenyl |
| 387 | 2-(4-CH$_3$-isoxazolyl)(cBu)CH | 2-CH$_3$-4-Cl-phenyl |
| 388 | cBu—CH(CH$_3$) | 2-CH$_3$-4-Cl-phenyl |
| 389 | 1-cBu—CH(CH$_2$CH$_3$) | 2-CH$_3$-4-Cl-phenyl |
| 390 | 1-cBu—CH(CH$_2$CH$_2$CH$_3$) | 2-CH$_3$-4-Cl-phenyl |
| 391 | 1-cBu—CH(CH$_2$OCH$_3$) | 2-CH$_3$-4-Cl-phenyl |
| 392 | 1-cBu—CH(CH$_2$CH$_2$OCH$_3$) | 2-CH$_3$-4-Cl-phenyl |
| 393 | (cPr)$_2$CH | 2-CH$_3$-4-MeO-phenyl |
| 394 | phenyl(cPr)CH | 2-CH$_3$-4-MeO-phenyl |
| 395 | 2-furanyl(cPr)CH | 2-CH$_3$-4-MeO-phenyl |
| 396 | 3-furan(cPr)CH | 2-CH$_3$-4-MeO-phenyl |
| 397 | 2-thienyl(cPr)CH | 2-CH$_3$-4-MeO-phenyl |
| 398 | 3-thienyl(cPr)CH | 2-CH$_3$-4-MeO-phenyl |
| 399 | 2-isoxazolyl(cPr)CH | 2-CH$_3$-4-MeO-phenyl |
| 400 | 2-(5-CH$_3$-furanyl)(cPr)CH | 2-CH$_3$-4-MeO-phenyl |
| 401 | 2-(4-CH$_3$-isoxazolyl)(cPr)CH | 2-CH$_3$-4-MeO-phenyl |
| 402 | cPr—CH(CH$_3$) | 2-CH$_3$-4-MeO-phenyl |
| 403 | 1-cPr—CH(CH$_2$CH$_3$) | 2-CH$_3$-4-MeO-phenyl |
| 404 | 1-cPr—CH(CH$_2$CH$_2$CH$_3$) | 2-CH$_3$-4-MeO-phenyl |
| 405 | 1-cPr—CH(CH$_2$OCH$_3$) | 2-CH$_3$-4-MeO-phenyl |
| 406 | 1-cPr—CH(CH$_2$CH$_2$OCH$_3$) | 2-CH$_3$-4-MeO-phenyl |
| 407 | (cBu)$_2$CH | 2-CH$_3$-4-MeO-phenyl |
| 408 | phenyl(cBu)CH | 2-CH$_3$-4-MeO-phenyl |
| 409 | 2-furanyl(cBu)CH | 2-CH$_3$-4-MeO-phenyl |
| 410 | 3-furan(cBu)CH | 2-CH$_3$-4-MeO-phenyl |
| 411 | 2-thienyl(cBu)CH | 2-CH$_3$-4-MeO-phenyl |
| 412 | 3-thienyl(cBu)CH | 2-CH$_3$-4-MeO-phenyl |
| 413 | 2-isoxazolyl(cBu)CH | 2-CH$_3$-4-MeO-phenyl |
| 414 | 2-(5-CH$_3$-furanyl)(cBu)CH | 2-CH$_3$-4-MeO-phenyl |
| 415 | 2-(4-CH$_3$-isoxazolyl)(cBu)CH | 2-CH$_3$-4-MeO-phenyl |
| 416 | cBu—CH(CH$_3$) | 2-CH$_3$-4-MeO-phenyl |
| 417 | 1-cBu—CH(CH$_2$CH$_3$) | 2-CH$_3$-4-MeO-phenyl |
| 418 | 1-cBu—CH(CH$_2$CH$_2$CH$_3$) | 2-CH$_3$-4-MeO-phenyl |
| 419 | 1-cBu—CH(CH$_2$OCH$_3$) | 2-CH$_3$-4-MeO-phenyl |
| 420 | 1-cBu—CH(CH$_2$CH$_2$OCH$_3$) | 2-CH$_3$-4-MeO-phenyl |
| 421 | (cPr)$_2$CH | 2,4-diCH$_3$-phenyl |
| 422 | phenyl(cPr)CH | 2,4-diCH$_3$-phenyl |
| 423 | 2-furanyl(cPr)CH | 2,4-diCH$_3$-phenyl |
| 424 | 3-furan(cPr)CH | 2,4-diCH$_3$-phenyl |
| 425 | 2-thienyl(cPr)CH | 2,4-diCH$_3$-phenyl |
| 426 | 3-thienyl(cPr)CH | 2,4-diCH$_3$-phenyl |
| 427 | 2-isoxazolyl(cPr)CH | 2,4-diCH$_3$-phenyl |
| 428 | 2-(5-CH$_3$-furanyl)(cPr)CH | 2,4-diCH$_3$-phenyl |
| 429 | 2-(4-CH$_3$-isoxazolyl)(cPr)CH | 2,4-diCH$_3$-phenyl |
| 430 | cPr—CH(CH$_3$) | 2,4-diCH$_3$-phenyl |
| 431 | 1-cPr—CH(CH$_2$CH$_3$) | 2,4-diCH$_3$-phenyl |
| 432 | 1-cPr—CH(CH$_2$CH$_2$CH$_3$) | 2,4-diCH$_3$-phenyl |
| 433 | 1-cPr—CH(CH$_2$OCH$_3$) | 2,4-diCH$_3$-phenyl |
| 434 | 1-cPr—CH(CH$_2$CH$_2$OCH$_3$) | 2,4-diCH$_3$-phenyl |
| 435 | (cBu)$_2$CH | 2,4-diCH$_3$-phenyl |
| 436 | phenyl(cBu)CH | 2,4-diCH$_3$-phenyl |
| 437 | 2-furanyl(cBu)CH | 2,4-diCH$_3$-phenyl |
| 438 | 3-furan(cBu)CH | 2,4-diCH$_3$-phenyl |
| 439 | 2-thienyl(cBu)CH | 2,4-diCH$_3$-phenyl |
| 440 | 3-thienyl(cBu)CH | 2,4-diCH$_3$-phenyl |
| 441 | 2-isoxazolyl(cBu)CH | 2,4-diCH$_3$-phenyl |
| 442 | 2-(5-CH$_3$-furanyl)(cBu)CH | 2,4-diCH$_3$-phenyl |
| 443 | 2-(4-CH$_3$-isoxazolyl)(cBu)CH | 2,4-diCH$_3$-phenyl |
| 444 | cBu—CH(CH$_3$) | 2,4-diCH$_3$-phenyl |
| 445 | 1-cBu—CH(CH$_2$CH$_3$) | 2,4-diCH$_3$-phenyl |
| 446 | 1-cBu—CH(CH$_2$CH$_2$CH$_3$) | 2,4-diCH$_3$-phenyl |
| 447 | 1-cBu—CH(CH$_2$OCH$_3$) | 2,4-diCH$_3$-phenyl |
| 448 | 1-cBu—CH(CH$_2$CH$_2$OCH$_3$) | 2,4-diCH$_3$-phenyl |
| 449 | (cPr)$_2$CH | 2-CH$_3$-4-(CH$_3$)$_2$N-phenyl |
| 450 | phenyl(cPr)CH | 2-CH$_3$-4-(CH$_3$)$_2$N-phenyl |
| 451 | 2-furanyl(cPr)CH | 2-CH$_3$-4-(CH$_3$)$_2$N-phenyl |
| 452 | 3-furan(cPr)CH | 2-CH$_3$-4-(CH$_3$)$_2$N-phenyl |
| 453 | 2-thienyl(cPr)CH | 2-CH$_3$-4-(CH$_3$)$_2$N-phenyl |
| 454 | 3-thienyl(cPr)CH | 2-CH$_3$-4-(CH$_3$)$_2$N-phenyl |
| 455 | 2-isoxazolyl(cPr)CH | 2-CH$_3$-4-(CH$_3$)$_2$N-phenyl |
| 456 | 2-(5-CH$_3$-furanyl)(cPr)CH | 2-CH$_3$-4-(CH$_3$)$_2$N-phenyl |
| 457 | 2-(4-CH$_3$-isoxazolyl)(cPr)CH | 2-CH$_3$-4-(CH$_3$)$_2$N-phenyl |
| 458 | cPr—CH(CH$_3$) | 2-CH$_3$-4-(CH$_3$)$_2$N-phenyl |
| 459 | 1-cPr—CH(CH$_2$CH$_3$) | 2-CH$_3$-4-(CH$_3$)$_2$N-phenyl |
| 460 | 1-cPr—CH(CH$_2$CH$_2$CH$_3$) | 2-CH$_3$-4-(CH$_3$)$_2$N-phenyl |
| 461 | 1-cPr—CH(CH$_2$OCH$_3$) | 2-CH$_3$-4-(CH$_3$)$_2$N-phenyl |
| 462 | 1-cPr—CH(CH$_2$CH$_2$OCH$_3$) | 2-CH$_3$-4-(CH$_3$)$_2$N-phenyl |
| 463 | (cBu)$_2$CH | 2-CH$_3$-4-(CH$_3$)$_2$N-phenyl |
| 464 | phenyl(cBu)CH | 2-CH$_3$-4-(CH$_3$)$_2$N-phenyl |
| 465 | 2-furanyl(cBu)CH | 2-CH$_3$-4-(CH$_3$)$_2$N-phenyl |
| 466 | 3-furan(cBu)CH | 2-CH$_3$-4-(CH$_3$)$_2$N-phenyl |
| 467 | 2-thienyl(cBu)CH | 2-CH$_3$-4-(CH$_3$)$_2$N-phenyl |
| 468 | 3-thienyl(cBu)CH | 2-CH$_3$-4-(CH$_3$)$_2$N-phenyl |
| 469 | 2-isoxazolyl(cBu)CH | 2-CH$_3$-4-(CH$_3$)$_2$N-phenyl |
| 470 | 2-(5-CH$_3$-furanyl)(cBu)CH | 2-CH$_3$-4-(CH$_3$)$_2$N-phenyl |
| 471 | 2-(4-CH$_3$-isoxazolyl)(cBu)CH | 2-CH$_3$-4-(CH$_3$)$_2$N-phenyl |
| 472 | cBu—CH(CH$_3$) | 2-CH$_3$-4-(CH$_3$)$_2$N-phenyl |
| 473 | 1-cBu—CH(CH$_2$CH$_3$) | 2-CH$_3$-4-(CH$_3$)$_2$N-phenyl |
| 474 | 1-cBu—CH(CH$_2$CH$_2$CH$_3$) | 2-CH$_3$-4-(CH$_3$)$_2$N-phenyl |

TABLE 1-continued

| | | |
|---|---|---|
| 475 | 1-cBu—CH(CH$_2$OCH$_3$) | 2-CH$_3$-4-(CH$_3$)$_2$N-phenyl |
| 476 | 1-cBu—CH(CH$_2$CH$_2$OCH$_3$) | 2-CH$_3$-4-(CH$_3$)$_2$N-phenyl |
| 477 | (cPr)$_2$CH | 2-MeO-4-CH$_3$-phenyl |
| 478 | phenyl(cPr)CH | 2-MeO-4-CH$_3$-phenyl |
| 479 | 2-furanyl(cPr)CH | 2-MeO-4-CH$_3$-phenyl |
| 480 | 3-furan(cPr)CH | 2-MeO-4-CH$_3$-phenyl |
| 481 | 2-thienyl(cPr)CH | 2-MeO-4-CH$_3$-phenyl |
| 482 | 3-thienyl(cPr)CH | 2-MeO-4-CH$_3$-phenyl |
| 483 | 2-isoxazolyl(cPr)CH | 2-MeO-4-CH$_3$-phenyl |
| 484 | 2-(5-CH$_3$-furanyl)(cPr)CH | 2-MeO-4-CH$_3$-phenyl |
| 485 | 2-(4-CH$_3$-isoxazolyl)(cPr)CH | 2-MeO-4-CH$_3$-phenyl |
| 486 | cPr—CH(CH$_3$) | 2-MeO-4-CH$_3$-phenyl |
| 487 | 1-cPr—CH(CH$_2$CH$_3$) | 2-MeO-4-CH$_3$-phenyl |
| 488 | 1-cPr—CH(CH$_2$CH$_2$CH$_3$) | 2-MeO-4-CH$_3$-phenyl |
| 489 | 1-cPr—CH(CH$_2$OCH$_3$) | 2-MeO-4-CH$_3$-phenyl |
| 490 | 1-cPr—CH(CH$_2$CH$_2$OCH$_3$) | 2-MeO-4-CH$_3$-phenyl |
| 491 | (cBu)$_2$CH | 2-MeO-4-CH$_3$-phenyl |
| 492 | phenyl(cBu)CH | 2-MeO-4-CH$_3$-phenyl |
| 493 | 2-furanyl(cBu)CH | 2-MeO-4-CH$_3$-phenyl |
| 494 | 3-furan(cBu)CH | 2-MeO-4-CH$_3$-phenyl |
| 495 | 2-thienyl(cBu)CH | 2-MeO-4-CH$_3$-phenyl |
| 496 | 3-thienyl(cBu)CH | 2-MeO-4-CH$_3$-phenyl |
| 497 | 2-isoxazolyl(cBu)CH | 2-MeO-4-CH$_3$-phenyl |
| 498 | 2-(5-CH$_3$-furanyl)(cBu)CH | 2-MeO-4-CH$_3$-phenyl |
| 499 | 2-(4-CH$_3$-isoxazolyl)(cBu)CH | 2-MeO-4-CH$_3$-phenyl |
| 500 | cBu—CH(CH$_3$) | 2-MeO-4-CH$_3$-phenyl |
| 501 | 1-cBu—CH(CH$_2$CH$_3$) | 2-MeO-4-CH$_3$-phenyl |
| 502 | 1-cBu—CH(CH$_2$CH$_2$CH$_3$) | 2-MeO-4-CH$_3$-phenyl |
| 503 | 1-cBu—CH(CH$_2$OCH$_3$) | 2-MeO-4-CH$_3$-phenyl |
| 504 | 1-cBu—CH(CH$_2$CH$_2$OCH$_3$) | 2-MeO-4-CH$_3$-phenyl |
| 505 | (cPr)$_2$CH | 2-MeO-4-CF$_3$-phenyl |
| 506 | phenyl(cPr)CH | 2-MeO-4-CF$_3$-phenyl |
| 507 | 2-furanyl(cPr)CH | 2-MeO-4-CF$_3$-phenyl |
| 508 | 3-furan(cPr)CH | 2-MeO-4-CF$_3$-phenyl |
| 509 | 2-thienyl(cPr)CH | 2-MeO-4-CF$_3$-phenyl |
| 510 | 3-thienyl(cPr)CH | 2-MeO-4-CF$_3$-phenyl |
| 511 | 2-isoxazolyl(cPr)CH | 2-MeO-4-CF$_3$-phenyl |
| 512 | 2-(5-CH$_3$-furanyl)(cPr)CH | 2-MeO-4-CF$_3$-phenyl |
| 513 | 2-(4-CH$_3$-isoxazolyl)(cPr)CH | 2-MeO-4-CF$_3$-phenyl |
| 514 | cPr—CH(CH$_3$) | 2-MeO-4-CF$_3$-phenyl |
| 515 | 1-cPr—CH(CH$_2$CH$_3$) | 2-MeO-4-CF$_3$-phenyl |
| 516 | 1-cPr—CH(CH$_2$CH$_2$CH$_3$) | 2-MeO-4-CF$_3$-phenyl |
| 517 | 1-cPr—CH(CH$_2$OCH$_3$) | 2-MeO-4-CF$_3$-phenyl |
| 518 | 1-cPr—CH(CH$_2$CH$_2$OCH$_3$) | 2-MeO-4-CF$_3$-phenyl |
| 519 | (cBu)$_2$CH | 2-MeO-4-CF$_3$-phenyl |
| 520 | phenyl(cBu)CH | 2-MeO-4-CF$_3$-phenyl |
| 521 | 2-furanyl(cBu)CH | 2-MeO-4-CF$_3$-phenyl |
| 522 | 3-furan(cBu)CH | 2-MeO-4-CF$_3$-phenyl |
| 523 | 2-thienyl(cBu)CH | 2-MeO-4-CF$_3$-phenyl |
| 524 | 3-thienyl(cBu)CH | 2-MeO-4-CF$_3$-phenyl |
| 525 | 2-isoxazolyl(cBu)CH | 2-MeO-4-CF$_3$-phenyl |
| 526 | 2-(5-CH$_3$-furanyl)(cBu)CH | 2-MeO-4-CF$_3$-phenyl |
| 527 | 2-(4-CH$_3$-isoxazolyl)(cBu)CH | 2-MeO-4-CF$_3$-phenyl |
| 528 | cBu—CH(CH$_3$) | 2-MeO-4-CF$_3$-phenyl |
| 529 | 1-cBu—CH(CH$_2$CH$_3$) | 2-MeO-4-CF$_3$-phenyl |
| 530 | 1-cBu—CH(CH$_2$CH$_2$CH$_3$) | 2-MeO-4-CF$_3$-phenyl |
| 531 | 1-cBu—CH(CH$_2$OCH$_3$) | 2-MeO-4-CF$_3$-phenyl |
| 532 | 1-cBu—CH(CH$_2$CH$_2$OCH$_3$) | 2-MeO-4-CF$_3$-phenyl |
| 533 | (cPr)$_2$CH | 2-MeO-4-Cl-phenyl |
| 534 | phenyl(cPr)CH | 2-MeO-4-Cl-phenyl |
| 535 | 2-furanyl(cPr)CH | 2-MeO-4-Cl-phenyl |
| 536 | 3-furan(cPr)CH | 2-MeO-4-Cl-phenyl |
| 537 | 2-thienyl(cPr)CH | 2-MeO-4-Cl-phenyl |
| 538 | 3-thienyl(cPr)CH | 2-MeO-4-Cl-phenyl |
| 539 | 2-isoxazolyl(cPr)CH | 2-MeO-4-Cl-phenyl |
| 540 | 2-(5-CH$_3$-furanyl)(cPr)CH | 2-MeO-4-Cl-phenyl |
| 541 | 2-(4-CH$_3$-isoxazolyl)(cPr)CH | 2-MeO-4-Cl-phenyl |
| 542 | cPr—CH(CH$_3$) | 2-MeO-4-Cl-phenyl |
| 543 | 1-cPr—CH(CH$_2$CH$_3$) | 2-MeO-4-Cl-phenyl |
| 544 | 1-cPr—CH(CH$_2$CH$_2$CH$_3$) | 2-MeO-4-Cl-phenyl |
| 545 | 1-cPr—CH(CH$_2$OCH$_3$) | 2-MeO-4-Cl-phenyl |
| 546 | 1-cPr—CH(CH$_2$CH$_2$OCH$_3$) | 2-MeO-4-Cl-phenyl |
| 547 | (cBu)$_2$CH | 2-MeO-4-Cl-phenyl |
| 548 | phenyl(cBu)CH | 2-MeO-4-Cl-phenyl |
| 549 | 2-furanyl(cBu)CH | 2-MeO-4-Cl-phenyl |
| 550 | 3-furan(cBu)CH | 2-MeO-4-Cl-phenyl |
| 551 | 2-thienyl(cBu)CH | 2-MeO-4-Cl-phenyl |
| 552 | 3-thienyl(cBu)CH | 2-MeO-4-Cl-phenyl |
| 553 | 2-isoxazolyl(cBu)CH | 2-MeO-4-Cl-phenyl |
| 554 | 2-(5-CH$_3$-furanyl)(cBu)CH | 2-MeO-4-Cl-phenyl |
| 555 | 2-(4-CH$_3$-isoxazolyl)(cBu)CH | 2-MeO-4-Cl-phenyl |
| 556 | cBu—CH(CH$_3$) | 2-MeO-4-Cl-phenyl |
| 557 | 1-cBu—CH(CH$_2$CH$_3$) | 2-MeO-4-Cl-phenyl |
| 558 | 1-cBu—CH(CH$_2$CH$_2$CH$_3$) | 2-MeO-4-Cl-phenyl |
| 559 | 1-cBu—CH(CH$_2$OCH$_3$) | 2-MeO-4-Cl-phenyl |
| 560 | 1-cBu—CH(CH$_2$CH$_2$OCH$_3$) | 2-MeO-4-Cl-phenyl |
| 561 | (cPr)$_2$CH | 2,4-diMeO-phenyl |
| 562 | phenyl(cPr)CH | 2,4-diMeO-phenyl |
| 563 | 2-furanyl(cPr)CH | 2,4-diMeO-phenyl |
| 564 | 3-furan(cPr)CH | 2,4-diMeO-phenyl |
| 565 | 2-thienyl(cPr)CH | 2,4-diMeO-phenyl |
| 566 | 3-thienyl(cPr)CH | 2,4-diMeO-phenyl |
| 567 | 2-isoxazolyl(cPr)CH | 2,4-diMeO-phenyl |
| 568 | 2-(5-CH$_3$-furanyl)(cPr)CH | 2,4-diMeO-phenyl |
| 569 | 2-(4-CH$_3$-isoxazolyl)(cPr)CH | 2,4-diMeO-phenyl |
| 570 | cPr—CH(CH$_3$) | 2,4-diMeO-phenyl |
| 571 | 1-cPr—CH(CH$_2$CH$_3$) | 2,4-diMeO-phenyl |
| 572 | 1-cPr—CH(CH$_2$CH$_2$CH$_3$) | 2,4-diMeO-phenyl |
| 573 | 1-cPr—CH(CH$_2$OCH$_3$) | 2,4-diMeO-phenyl |
| 574 | 1-cPr—CH(CH$_2$CH$_2$OCH$_3$) | 2,4-diMeO-phenyl |
| 575 | (cBu)$_2$CH | 2,4-diMeO-phenyl |
| 576 | phenyl(cBu)CH | 2,4-diMeO-phenyl |
| 577 | 2-furanyl(cBu)CH | 2,4-diMeO-phenyl |
| 578 | 3-furan(cBu)CH | 2,4-diMeO-phenyl |
| 579 | 2-thienyl(cBu)CH | 2,4-diMeO-phenyl |
| 580 | 3-thienyl(cBu)CH | 2,4-diMeO-phenyl |
| 581 | 2-isoxazolyl(cBu)CH | 2,4-diMeO-phenyl |
| 582 | 2-(5-CH$_3$-furanyl)(cBu)CH | 2,4-diMeO-phenyl |
| 583 | 2-(4-CH$_3$-isoxazolyl)(cBu)CH | 2,4-diMeO-phenyl |
| 584 | cBu—CH(CH$_3$) | 2,4-diMeO-phenyl |
| 585 | 1-cBu—CH(CH$_2$CH$_3$) | 2,4-diMeO-phenyl |
| 586 | 1-cBu—CH(CH$_2$CH$_2$CH$_3$) | 2,4-diMeO-phenyl |
| 587 | 1-cBu—CH(CH$_2$OCH$_3$) | 2,4-diMeO-phenyl |
| 588 | 1-cBu—CH(CH$_2$CH$_2$OCH$_3$) | 2,4-diMeO-phenyl |
| 589 | (cPr)$_2$CH | 2,4-diCl-6-CH$_3$-phenyl |
| 590 | phenyl(cPr)CH | 2,4-diCl-6-CH$_3$-phenyl |
| 591 | 2-furanyl(cPr)CH | 2,4-diCl-6-CH$_3$-phenyl |
| 592 | 3-furan(cPr)CH | 2,4-diCl-6-CH$_3$-phenyl |
| 593 | 2-thienyl(cPr)CH | 2,4-diCl-6-CH$_3$-phenyl |
| 594 | 3-thienyl(cPr)CH | 2,4-diCl-6-CH$_3$-phenyl |
| 595 | 2-isoxazolyl(cPr)CH | 2,4-diCl-6-CH$_3$-phenyl |
| 596 | 2-(5-CH$_3$-furanyl)(cPr)CH | 2,4-diCl-6-CH$_3$-phenyl |
| 597 | 2-(4-CH$_3$-isoxazolyl)(cPr)CH | 2,4-diCl-6-CH$_3$-phenyl |
| 598 | cPr—CH(CH$_3$) | 2,4-diCl-6-CH$_3$-phenyl |
| 599 | 1-cPr—CH(CH$_2$CH$_3$) | 2,4-diCl-6-CH$_3$-phenyl |
| 600 | 1-cPr—CH(CH$_2$CH$_2$CH$_3$) | 2,4-diCl-6-CH$_3$-phenyl |
| 601 | 1-cPr—CH(CH$_2$OCH$_3$) | 2,4-diCl-6-CH$_3$-phenyl |
| 602 | 1-cPr—CH(CH$_2$CH$_2$OCH$_3$) | 2,4-diCl-6-CH$_3$-phenyl |
| 603 | (cBu)$_2$CH | 2,4-diCl-6-CH$_3$-phenyl |
| 604 | phenyl(cBu)CH | 2,4-diCl-6-CH$_3$-phenyl |
| 605 | 2-furanyl(cBu)CH | 2,4-diCl-6-CH$_3$-phenyl |
| 606 | 3-furan(cBu)CH | 2,4-diCl-6-CH$_3$-phenyl |
| 607 | 2-thienyl(cBu)CH | 2,4-diCl-6-CH$_3$-phenyl |
| 608 | 3-thienyl(cBu)CH | 2,4-diCl-6-CH$_3$-phenyl |
| 609 | 2-isoxazolyl(cBu)CH | 2,4-diCl-6-CH$_3$-phenyl |
| 610 | 2-(5-CH$_3$-furanyl)(cBu)CH | 2,4-diCl-6-CH$_3$-phenyl |
| 611 | 2-(4-CH$_3$-isoxazolyl)(cBu)CH | 2,4-diCl-6-CH$_3$-phenyl |
| 612 | cBu—CH(CH$_3$) | 2,4-diCl-6-CH$_3$-phenyl |
| 613 | 1-cBu—CH(CH$_2$CH$_3$) | 2,4-diCl-6-CH$_3$-phenyl |
| 614 | 1-cBu—CH(CH$_2$CH$_2$CH$_3$) | 2,4-diCl-6-CH$_3$-phenyl |
| 615 | 1-cBu—CH(CH$_2$OCH$_3$) | 2,4-diCl-6-CH$_3$-phenyl |
| 616 | 1-cBu—CH(CH$_2$CH$_2$OCH$_3$) | 2,4-diCl-6-CH$_3$-phenyl |
| 617 | (cPr)$_2$CH | 2,4-diCl-5-F-phenyl |
| 618 | phenyl(cPr)CH | 2,4-diCl-5-F-phenyl |
| 619 | 2-furanyl(cPr)CH | 2,4-diCl-5-F-phenyl |
| 620 | 3-furan(cPr)CH | 2,4-diCl-5-F-phenyl |
| 621 | 2-thienyl(cPr)CH | 2,4-diCl-5-F-phenyl |
| 622 | 3-thienyl(cPr)CH | 2,4-diCl-5-F-phenyl |
| 623 | 2-isoxazolyl(cPr)CH | 2,4-diCl-5-F-phenyl |
| 624 | 2-(5-CH$_3$-furanyl)(cPr)CH | 2,4-diCl-5-F-phenyl |
| 625 | 2-(4-CH$_3$-isoxazolyl)(cPr)CH | 2,4-diCl-5-F-phenyl |
| 626 | cPr—CH(CH$_3$) | 2,4-diCl-5-F-phenyl |
| 627 | 1-cPr—CH(CH$_2$CH$_3$) | 2,4-diCl-5-F-phenyl |
| 628 | 1-cPr—CH(CH$_2$CH$_2$CH$_3$) | 2,4-diCl-5-F-phenyl |
| 629 | 1-cPr—CH(CH$_2$OCH$_3$) | 2,4-diCl-5-F-phenyl |
| 630 | 1-cPr—CH(CH$_2$CH$_2$OCH$_3$) | 2,4-diCl-5-F-phenyl |
| 631 | (cBu)$_2$CH | 2,4-diCl-5-F-phenyl |
| 632 | phenyl(cBu)CH | 2,4-diCl-5-F-phenyl |

TABLE 1-continued

| | | |
|---|---|---|
| 633 | 2-furanyl(cBu)CH | 2,4-diCl-5-F-phenyl |
| 634 | 3-furan(cBu)CH | 2,4-diCl-5-F-phenyl |
| 635 | 2-thienyl(cBu)CH | 2,4-diCl-5-F-phenyl |
| 636 | 3-thienyl(cBu)CH | 2,4-diCl-5-F-phenyl |
| 637 | 2-isoxazolyl(cBu)CH | 2,4-diCl-5-F-phenyl |
| 638 | 2-(5-CH$_3$-furanyl)(cBu)CH | 2,4-diCl-5-F-phenyl |
| 639 | 2-(4-CH$_3$-isoxazolyl)(cBu)CH | 2,4-diCl-5-F-phenyl |
| 640 | cBu—CH(CH$_3$) | 2,4-diCl-5-F-phenyl |
| 641 | 1-cBu—CH(CH$_2$CH$_3$) | 2,4-diCl-5-F-phenyl |
| 642 | 1-cBu—CH(CH$_2$CH$_2$CH$_3$) | 2,4-diCl-5-F-phenyl |
| 643 | 1-cBu—CH(CH$_2$OCH$_3$) | 2,4-diCl-5-F-phenyl |
| 644 | 1-cBu—CH(CH$_2$CH$_2$OCH$_3$) | 2,4-diCl-5-F-phenyl |
| 645 | (cPr)$_2$CH | 2,4-diCl-6-MeS-phenyl |
| 646 | phenyl(cPr)CH | 2,4-diCl-6-MeS-phenyl |
| 647 | 2-furanyl(cPr)CH | 2,4-diCl-6-MeS-phenyl |
| 648 | 3-furan(cPr)CH | 2,4-diCl-6-MeS-phenyl |
| 649 | 2-thienyl(cPr)CH | 2,4-diCl-6-MeS-phenyl |
| 650 | 3-thienyl(cPr)CH | 2,4-diCl-6-MeS-phenyl |
| 651 | 2-isoxazolyl(cPr)CH | 2,4-diCl-6-MeS-phenyl |
| 652 | 2-(5-CH$_3$-furanyl)(cPr)CH | 2,4-diCl-6-MeS-phenyl |
| 653 | 2-(4-CH$_3$-isoxazolyl)(cPr)CH | 2,4-diCl-6-MeS-phenyl |
| 654 | cPr—CH(CH$_3$) | 2,4-diCl-6-MeS-phenyl |
| 655 | 1-cPr—CH(CH$_2$CH$_3$) | 2,4-diCl-6-MeS-phenyl |
| 656 | 1-cPr—CH(CH$_2$CH$_2$CH$_3$) | 2,4-diCl-6-MeS-phenyl |
| 657 | 1-cPr—CH(CH$_2$OCH$_3$) | 2,4-diCl-6-MeS-phenyl |
| 658 | 1-cPr—CH(CH$_2$CH$_2$OCH$_3$) | 2,4-diCl-6-MeS-phenyl |
| 659 | (cBu)$_2$CH | 2,4-diCl-6-MeS-phenyl |
| 660 | phenyl(cBu)CH | 2,4-diCl-6-MeS-phenyl |
| 661 | 2-furanyl(cBu)CH | 2,4-diCl-6-MeS-phenyl |
| 662 | 3-furan(cBu)CH | 2,4-diCl-6-MeS-phenyl |
| 663 | 2-thienyl(cBu)CH | 2,4-diCl-6-MeS-phenyl |
| 664 | 3-thienyl(cBu)CH | 2,4-diCl-6-MeS-phenyl |
| 665 | 2-isoxazolyl(cBu)CH | 2,4-diCl-6-MeS-phenyl |
| 666 | 2-(5-CH$_3$-furanyl)(cBu)CH | 2,4-diCl-6-MeS-phenyl |
| 667 | 2-(4-CH$_3$-isoxazolyl)(cBu)CH | 2,4-diCl-6-MeS-phenyl |
| 668 | cBu—CH(CH$_3$) | 2,4-diCl-6-MeS-phenyl |
| 669 | 1-cBu—CH(CH$_2$CH$_3$) | 2,4-diCl-6-MeS-phenyl |
| 670 | 1-cBu—CH(CH$_2$CH$_2$CH$_3$) | 2,4-diCl-6-MeS-phenyl |
| 671 | 1-cBu—CH(CH$_2$OCH$_3$) | 2,4-diCl-6-MeS-phenyl |
| 672 | 1-cBu—CH(CH$_2$CH$_2$OCH$_3$) | 2,4-diCl-6-MeS-phenyl |
| 673 | (cPr)$_2$CH | 2,4-diCl-6-MeO-phenyl |
| 674 | phenyl(cPr)CH | 2,4-diCl-6-MeO-phenyl |
| 675 | 2-furanyl(cPr)CH | 2,4-diCl-6-MeO-phenyl |
| 676 | 3-furan(cPr)CH | 2,4-diCl-6-MeO-phenyl |
| 677 | 2-thienyl(cPr)CH | 2,4-diCl-6-MeO-phenyl |
| 678 | 3-thienyl(cPr)CH | 2,4-diCl-6-MeO-phenyl |
| 679 | 2-isoxazolyl(cPr)CH | 2,4-diCl-6-MeO-phenyl |
| 680 | 2-(5-CH$_3$-furanyl)(cPr)CH | 2,4-diCl-6-MeO-phenyl |
| 681 | 2-(4-CH$_3$-isoxazolyl)(cPr)CH | 2,4-diCl-6-MeO-phenyl |
| 682 | cPr—CH(CH$_3$) | 2,4-diCl-6-MeO-phenyl |
| 683 | 1-cPr—CH(CH$_2$CH$_3$) | 2,4-diCl-6-MeO-phenyl |
| 684 | 1-cPr—CH(CH$_2$CH$_2$CH$_3$) | 2,4-diCl-6-MeO-phenyl |
| 685 | 1-cPr—CH(CH$_2$OCH$_3$) | 2,4-diCl-6-MeO-phenyl |
| 686 | 1-cPr—CH(CH$_2$CH$_2$OCH$_3$) | 2,4-diCl-6-MeO-phenyl |
| 687 | (cBu)$_2$CH | 2,4-diCl-6-MeO-phenyl |
| 688 | phenyl(cBu)CH | 2,4-diCl-6-MeO-phenyl |
| 689 | 2-furanyl(cBu)CH | 2,4-diCl-6-MeO-phenyl |
| 690 | 3-furan(cBu)CH | 2,4-diCl-6-MeO-phenyl |
| 691 | 2-thienyl(cBu)CH | 2,4-diCl-6-MeO-phenyl |
| 692 | 3-thienyl(cBu)CH | 2,4-diCl-6-MeO-phenyl |
| 693 | 2-isoxazolyl(cBu)CH | 2,4-diCl-6-MeO-phenyl |
| 694 | 2-(5-CH$_3$-furanyl)(cBu)CH | 2,4-diCl-6-MeO-phenyl |
| 695 | 2-(4-CH$_3$-isoxazolyl)(cBu)CH | 2,4-diCl-6-MeO-phenyl |
| 696 | cBu—CH(CH$_3$) | 2,4-diCl-6-MeO-phenyl |
| 697 | 1-cBu—CH(CH$_2$CH$_3$) | 2,4-diCl-6-MeO-phenyl |
| 698 | 1-cBu—CH(CH$_2$CH$_2$CH$_3$) | 2,4-diCl-6-MeO-phenyl |
| 699 | 1-cBu—CH(CH$_2$OCH$_3$) | 2,4-diCl-6-MeO-phenyl |
| 700 | 1-cBu—CH(CH$_2$CH$_2$OCH$_3$) | 2,4-diCl-6-MeO-phenyl |
| 701 | (cPr)$_2$CH | 2,5-diCl-4-MeO-phenyl |
| 702 | phenyl(cPr)CH | 2,5-diCl-4-MeO-phenyl |
| 703 | 2-furanyl(cPr)CH | 2,5-diCl-4-MeO-phenyl |
| 704 | 3-furan(cPr)CH | 2,5-diCl-4-MeO-phenyl |
| 705 | 2-thienyl(cPr)CH | 2,5-diCl-4-MeO-phenyl |
| 706 | 3-thienyl(cPr)CH | 2,5-diCl-4-MeO-phenyl |
| 707 | 2-isoxazolyl(cPr)CH | 2,5-diCl-4-MeO-phenyl |
| 708 | 2-(5-CH$_3$-furanyl)(cPr)CH | 2,5-diCl-4-MeO-phenyl |
| 709 | 2-(4-CH$_3$-isoxazolyl)(cPr)CH | 2,5-diCl-4-MeO-phenyl |
| 710 | cPr—CH(CH$_3$) | 2,5-diCl-4-MeO-phenyl |
| 711 | 1-cPr—CH(CH$_2$CH$_3$) | 2,5-diCl-4-MeO-phenyl |
| 712 | 1-cPr—CH(CH$_2$CH$_2$CH$_3$) | 2,5-diCl-4-MeO-phenyl |
| 713 | 1-cPr—CH(CH$_2$OCH$_3$) | 2,5-diCl-4-MeO-phenyl |
| 714 | 1-cPr—CH(CH$_2$CH$_2$OCH$_3$) | 2,5-diCl-4-MeO-phenyl |
| 715 | (cBu)$_2$CH | 2,5-diCl-4-MeO-phenyl |
| 716 | phenyl(cBu)CH | 2,5-diCl-4-MeO-phenyl |
| 717 | 2-furanyl(cBu)CH | 2,5-diCl-4-MeO-phenyl |
| 718 | 3-furan(cBu)CH | 2,5-diCl-4-MeO-phenyl |
| 719 | 2-thienyl(cBu)CH | 2,5-diCl-4-MeO-phenyl |
| 720 | 3-thienyl(cBu)CH | 2,5-diCl-4-MeO-phenyl |
| 721 | 2-isoxazolyl(cBu)CH | 2,5-diCl-4-MeO-phenyl |
| 722 | 2-(5-CH$_3$-furanyl)(cBu)CH | 2,5-diCl-4-MeO-phenyl |
| 723 | 2-(4-CH$_3$-isoxazolyl)(cBu)CH | 2,5-diCl-4-MeO-phenyl |
| 724 | cBu—CH(CH$_3$) | 2,5-diCl-4-MeO-phenyl |
| 725 | 1-cBu—CH(CH$_2$CH$_3$) | 2,5-diCl-4-MeO-phenyl |
| 726 | 1-cBu—CH(CH$_2$CH$_2$CH$_3$) | 2,5-diCl-4-MeO-phenyl |
| 727 | 1-cBu—CH(CH$_2$OCH$_3$) | 2,5-diCl-4-MeO-phenyl |
| 728 | 1-cBu—CH(CH$_2$CH$_2$OCH$_3$) | 2,5-diCl-4-MeO-phenyl |
| 729 | (cPr)$_2$CH | 2,4,6-triCl-phenyl |
| 730 | phenyl(cPr)CH | 2,4,6-triCl-phenyl |
| 731 | 2-furanyl(cPr)CH | 2,4,6-triCl-phenyl |
| 732 | 3-furan(cPr)CH | 2,4,6-triCl-phenyl |
| 733 | 2-thienyl(cPr)CH | 2,4,6-triCl-phenyl |
| 734 | 3-thienyl(cPr)CH | 2,4,6-triCl-phenyl |
| 735 | 2-isoxazolyl(cPr)CH | 2,4,6-triCl-phenyl |
| 736 | 2-(5-CH$_3$-furanyl)(cPr)CH | 2,4,6-triCl-phenyl |
| 737 | 2-(4-CH$_3$-isoxazolyl)(cPr)CH | 2,4,6-triCl-phenyl |
| 738 | cPr—CH(CH$_3$) | 2,4,6-triCl-phenyl |
| 739 | 1-cPr—CH(CH$_2$CH$_3$) | 2,4,6-triCl-phenyl |
| 740 | 1-cPr—CH(CH$_2$CH$_2$CH$_3$) | 2,4,6-triCl-phenyl |
| 741 | 1-cPr—CH(CH$_2$OCH$_3$) | 2,4,6-triCl-phenyl |
| 742 | 1-cPr—CH(CH$_2$CH$_2$OCH$_3$) | 2,4,6-triCl-phenyl |
| 743 | (cBu)$_2$CH | 2,4,6-triCl-phenyl |
| 744 | phenyl(cBu)CH | 2,4,6-triCl-phenyl |
| 745 | 2-furanyl(cBu)CH | 2,4,6-triCl-phenyl |
| 746 | 3-furan(cBu)CH | 2,4,6-triCl-phenyl |
| 747 | 2-thienyl(cBu)CH | 2,4,6-triCl-phenyl |
| 748 | 3-thienyl(cBu)CH | 2,4,6-triCl-phenyl |
| 749 | 2-isoxazolyl(cBu)CH | 2,4,6-triCl-phenyl |
| 750 | 2-(5-CH$_3$-furanyl)(cBu)CH | 2,4,6-triCl-phenyl |
| 751 | 2-(4-CH$_3$-isoxazolyl)(cBu)CH | 2,4,6-triCl-phenyl |
| 752 | cBu—CH(CH$_3$) | 2,4,6-triCl-phenyl |
| 753 | 1-cBu—CH(CH$_2$CH$_3$) | 2,4,6-triCl-phenyl |
| 754 | 1-cBu—CH(CH$_2$CH$_2$CH$_3$) | 2,4,6-triCl-phenyl |
| 755 | 1-cBu—CH(CH$_2$OCH$_3$) | 2,4,6-triCl-phenyl |
| 756 | 1-cBu—CH(CH$_2$CH$_2$OCH$_3$) | 2,4,6-triCl-phenyl |
| 757 | (cPr)$_2$CH | 2-Cl-4-CH$_3$-5-F-phenyl |
| 758 | phenyl(cPr)CH | 2-Cl-4-CH$_3$-5-F-phenyl |
| 759 | 2-furanyl(cPr)CH | 2-Cl-4-CH$_3$-5-F-phenyl |
| 760 | 3-furan(cPr)CH | 2-Cl-4-CH$_3$-5-F-phenyl |
| 761 | 2-thienyl(cPr)CH | 2-Cl-4-CH$_3$-5-F-phenyl |
| 762 | 3-thienyl(cPr)CH | 2-Cl-4-CH$_3$-5-F-phenyl |
| 763 | 2-isoxazolyl(cPr)CH | 2-Cl-4-CH$_3$-5-F-phenyl |
| 764 | 2-(5-CH$_3$-furanyl)(cPr)CH | 2-Cl-4-CH$_3$-5-F-phenyl |
| 765 | 2-(4-CH$_3$-isoxazolyl)(cPr)CH | 2-Cl-4-CH$_3$-5-F-phenyl |
| 766 | cPr—CH(CH$_3$) | 2-Cl-4-CH$_3$-5-F-phenyl |
| 767 | 1-cPr—CH(CH$_2$CH$_3$) | 2-Cl-4-CH$_3$-5-F-phenyl |
| 768 | 1-cPr—CH(CH$_2$CH$_2$CH$_3$) | 2-Cl-4-CH$_3$-5-F-phenyl |
| 769 | 1-cPr—CH(CH$_2$OCH$_3$) | 2-Cl-4-CH$_3$-5-F-phenyl |
| 770 | 1-cPr—CH(CH$_2$CH$_2$OCH$_3$) | 2-Cl-4-CH$_3$-5-F-phenyl |
| 771 | (cBu)$_2$CH | 2-Cl-4-CH$_3$-5-F-phenyl |
| 772 | phenyl(cBu)CH | 2-Cl-4-CH$_3$-5-F-phenyl |
| 773 | 2-furanyl(cBu)CH | 2-Cl-4-CH$_3$-5-F-phenyl |
| 774 | 3-furan(cBu)CH | 2-Cl-4-CH$_3$-5-F-phenyl |
| 775 | 2-thienyl(cBu)CH | 2-Cl-4-CH$_3$-5-F-phenyl |
| 776 | 3-thienyl(cBu)CH | 2-Cl-4-CH$_3$-5-F-phenyl |
| 777 | 2-isoxazolyl(cBu)CH | 2-Cl-4-CH$_3$-5-F-phenyl |
| 778 | 2-(5-CH$_3$-furanyl)(cBu)CH | 2-Cl-4-CH$_3$-5-F-phenyl |
| 779 | 2-(4-CH$_3$-isoxazolyl)(cBu)CH | 2-Cl-4-CH$_3$-5-F-phenyl |
| 780 | cBu—CH(CH$_3$) | 2-Cl-4-CH$_3$-5-F-phenyl |
| 781 | 1-cBu—CH(CH$_2$CH$_3$) | 2-Cl-4-CH$_3$-5-F-phenyl |
| 782 | 1-cBu—CH(CH$_2$CH$_2$CH$_3$) | 2-Cl-4-CH$_3$-5-F-phenyl |
| 783 | 1-cBu—CH(CH$_2$OCH$_3$) | 2-Cl-4-CH$_3$-5-F-phenyl |
| 784 | 1-cBu—CH(CH$_2$CH$_2$OCH$_3$) | 2-Cl-4-CH$_3$-5-F-phenyl |
| 785 | (cPr)$_2$CH | 2-Cl-4-MeO-5-CH$_3$-phenyl |
| 786 | phenyl(cPr)CH | 2-Cl-4-MeO-5-CH$_3$-phenyl |
| 787 | 2-furanyl(cPr)CH | 2-Cl-4-MeO-5-CH$_3$-phenyl |
| 788 | 3-furan(cPr)CH | 2-Cl-4-MeO-5-CH$_3$-phenyl |
| 789 | 2-thienyl(cPr)CH | 2-Cl-4-MeO-5-CH$_3$-phenyl |
| 790 | 3-thienyl(cPr)CH | 2-Cl-4-MeO-5-CH$_3$-phenyl |

TABLE 1-continued

| # | | |
|---|---|---|
| 791 | 2-isoxazolyl(cPr)CH | 2-Cl-4-MeO-5-CH₃-phenyl |
| 792 | 2-(5-CH₃-furanyl)(cPr)CH | 2-Cl-4-MeO-5-CH₃-phenyl |
| 793 | 2-(4-CH₃-isoxazolyl)(cPr)CH | 2-Cl-4-MeO-5-CH₃-phenyl |
| 794 | cPr—CH(CH₃) | 2-Cl-4-MeO-5-CH₃-phenyl |
| 795 | 1-cPr—CH(CH₂CH₃) | 2-Cl-4-MeO-5-CH₃-phenyl |
| 796 | 1-cPr—CH(CH₂CH₂CH₃) | 2-Cl-4-MeO-5-CH₃-phenyl |
| 797 | 1-cPr—CH(CH₂OCH₃) | 2-Cl-4-MeO-5-CH₃-phenyl |
| 798 | 1-cPr—CH(CH₂CH₂OCH₃) | 2-Cl-4-MeO-5-CH₃-phenyl |
| 799 | (cBu)₂CH | 2-Cl-4-MeO-5-CH₃-phenyl |
| 800 | phenyl(cBu)CH | 2-Cl-4-MeO-5-CH₃-phenyl |
| 801 | 2-furanyl(cBu)CH | 2-Cl-4-MeO-5-CH₃-phenyl |
| 802 | 3-furan(cBu)CH | 2-Cl-4-MeO-5-CH₃-phenyl |
| 803 | 2-thienyl(cBu)CH | 2-Cl-4-MeO-5-CH₃-phenyl |
| 804 | 3-thienyl(cBu)CH | 2-Cl-4-MeO-5-CH₃-phenyl |
| 805 | 2-isoxazolyl(cBu)CH | 2-Cl-4-MeO-5-CH₃-phenyl |
| 806 | 2-(5-CH₃-furanyl)(cBu)CH | 2-Cl-4-MeO-5-CH₃-phenyl |
| 807 | 2-(4-CH₃-isoxazolyl)(cBu)CH | 2-Cl-4-MeO-5-CH₃-phenyl |
| 808 | cBu—CH(CH₃) | 2-Cl-4-MeO-5-CH₃-phenyl |
| 809 | 1-cBu—CH(CH₂CH₃) | 2-Cl-4-MeO-5-CH₃-phenyl |
| 810 | 1-cBu—CH(CH₂CH₂CH₃) | 2-Cl-4-MeO-5-CH₃-phenyl |
| 811 | 1-cBu—CH(CH₂OCH₃) | 2-Cl-4-MeO-5-CH₃-phenyl |
| 812 | 1-cBu—CH(CH₂CH₂OCH₃) | 2-Cl-4-MeO-5-CH₃-phenyl |
| 813 | (cPr)₂CH | 2-Cl-4-MeO-5-F-phenyl |
| 814 | phenyl(cPr)CH | 2-Cl-4-MeO-5-F-phenyl |
| 815 | 2-furanyl(cPr)CH | 2-Cl-4-MeO-5-F-phenyl |
| 816 | 3-furan(cPr)CH | 2-Cl-4-MeO-5-F-phenyl |
| 817 | 2-thienyl(cPr)CH | 2-Cl-4-MeO-5-F-phenyl |
| 818 | 3-thienyl(cPr)CH | 2-Cl-4-MeO-5-F-phenyl |
| 819 | 2-isoxazolyl(cPr)CH | 2-Cl-4-MeO-5-F-phenyl |
| 820 | 2-(5-CH₃-furanyl)(cPr)CH | 2-Cl-4-MeO-5-F-phenyl |
| 821 | 2-(4-CH₃-isoxazolyl)(cPr)CH | 2-Cl-4-MeO-5-F-phenyl |
| 822 | cPr—CH(CH₃) | 2-Cl-4-MeO-5-F-phenyl |
| 823 | 1-cPr—CH(CH₂CH₃) | 2-Cl-4-MeO-5-F-phenyl |
| 824 | 1-cPr—CH(CH₂CH₂CH₃) | 2-Cl-4-MeO-5-F-phenyl |
| 825 | 1-cPr—CH(CH₂OCH₃) | 2-Cl-4-MeO-5-F-phenyl |
| 826 | 1-cPr—CH(CH₂CH₂OCH₃) | 2-Cl-4-MeO-5-F-phenyl |
| 827 | (cBu)₂CH | 2-Cl-4-MeO-5-F-phenyl |
| 828 | phenyl(cBu)CH | 2-Cl-4-MeO-5-F-phenyl |
| 829 | 2-furanyl(cBu)CH | 2-Cl-4-MeO-5-F-phenyl |
| 830 | 3-furan(cBu)CH | 2-Cl-4-MeO-5-F-phenyl |
| 831 | 2-thienyl(cBu)CH | 2-Cl-4-MeO-5-F-phenyl |
| 832 | 3-thienyl(cBu)CH | 2-Cl-4-MeO-5-F-phenyl |
| 833 | 2-isoxazolyl(cBu)CH | 2-Cl-4-MeO-5-F-phenyl |
| 834 | 2-(5-CH₃-furanyl)(cBu)CH | 2-Cl-4-MeO-5-F-phenyl |
| 835 | 2-(4-CH₃-isoxazolyl)(cBu)CH | 2-Cl-4-MeO-5-F-phenyl |
| 836 | cBu—CH(CH₃) | 2-Cl-4-MeO-5-F-phenyl |
| 837 | 1-cBu—CH(CH₂CH₃) | 2-Cl-4-MeO-5-F-phenyl |
| 838 | 1-cBu—CH(CH₂CH₂CH₃) | 2-Cl-4-MeO-5-F-phenyl |
| 839 | 1-cBu—CH(CH₂OCH₃) | 2-Cl-4-MeO-5-F-phenyl |
| 840 | 1-cBu—CH(CH₂CH₂OCH₃) | 2-Cl-4-MeO-5-F-phenyl |
| 841 | (cPr)₂CH | 2-CH₃-4-MeO-5-Cl-phenyl |
| 842 | phenyl(cPr)CH | 2-CH₃-4-MeO-5-Cl-phenyl |
| 843 | 2-furanyl(cPr)CH | 2-CH₃-4-MeO-5-Cl-phenyl |
| 844 | 3-furan(cPr)CH | 2-CH₃-4-MeO-5-Cl-phenyl |
| 845 | 2-thienyl(cPr)CH | 2-CH₃-4-MeO-5-Cl-phenyl |
| 846 | 3-thienyl(cPr)CH | 2-CH₃-4-MeO-5-Cl-phenyl |
| 847 | 2-isoxazolyl(cPr)CH | 2-CH₃-4-MeO-5-Cl-phenyl |
| 848 | 2-(5-CH₃-furanyl)(cPr)CH | 2-CH₃-4-MeO-5-Cl-phenyl |
| 849 | 2-(4-CH₃-isoxazolyl)(cPr)CH | 2-CH₃-4-MeO-5-Cl-phenyl |
| 850 | cPr—CH(CH₃) | 2-CH₃-4-MeO-5-Cl-phenyl |
| 851 | 1-cPr—CH(CH₂CH₃) | 2-CH₃-4-MeO-5-Cl-phenyl |
| 852 | 1-cPr—CH(CH₂CH₂CH₃) | 2-CH₃-4-MeO-5-Cl-phenyl |
| 853 | 1-cPr—CH(CH₂OCH₃) | 2-CH₃-4-MeO-5-Cl-phenyl |
| 854 | 1-cPr—CH(CH₂CH₂OCH₃) | 2-CH₃-4-MeO-5-Cl-phenyl |
| 855 | (cBu)₂CH | 2-CH₃-4-MeO-5-Cl-phenyl |
| 856 | phenyl(cBu)CH | 2-CH₃-4-MeO-5-Cl-phenyl |
| 857 | 2-furanyl(cBu)CH | 2-CH₃-4-MeO-5-Cl-phenyl |
| 858 | 3-furan(cBu)CH | 2-CH₃-4-MeO-5-Cl-phenyl |
| 859 | 2-thienyl(cBu)CH | 2-CH₃-4-MeO-5-Cl-phenyl |
| 860 | 3-thienyl(cBu)CH | 2-CH₃-4-MeO-5-Cl-phenyl |
| 861 | 2-isoxazolyl(cBu)CH | 2-CH₃-4-MeO-5-Cl-phenyl |
| 862 | 2-(5-CH₃-furanyl)(cBu)CH | 2-CH₃-4-MeO-5-Cl-phenyl |
| 863 | 2-(4-CH₃-isoxazolyl)(cBu)CH | 2-CH₃-4-MeO-5-Cl-phenyl |
| 864 | cBu—CH(CH₃) | 2-CH₃-4-MeO-5-Cl-phenyl |
| 865 | 1-cBu—CH(CH₂CH₃) | 2-CH₃-4-MeO-5-Cl-phenyl |
| 866 | 1-cBu—CH(CH₂CH₂CH₃) | 2-CH₃-4-MeO-5-Cl-phenyl |
| 867 | 1-cBu—CH(CH₂OCH₃) | 2-CH₃-4-MeO-5-Cl-phenyl |
| 868 | 1-cBu—CH(CH₂CH₂OCH₃) | 2-CH₃-4-MeO-5-Cl-phenyl |
| 869 | (cPr)₂CH | 2,5-diCH₃-4-MeO-phenyl |
| 870 | phenyl(cPr)CH | 2,5-diCH₃-4-MeO-phenyl |
| 871 | 2-furanyl(cPr)CH | 2,5-diCH₃-4-MeO-phenyl |
| 872 | 3-furan(cPr)CH | 2,5-diCH₃-4-MeO-phenyl |
| 873 | 2-thienyl(cPr)CH | 2,5-diCH₃-4-MeO-phenyl |
| 874 | 3-thienyl(cPr)CH | 2,5-diCH₃-4-MeO-phenyl |
| 875 | 2-isoxazolyl(cPr)CH | 2,5-diCH₃-4-MeO-phenyl |
| 876 | 2-(5-CH₃-furanyl)(cPr)CH | 2,5-diCH₃-4-MeO-phenyl |
| 877 | 2-(4-CH₃-isoxazolyl)(cPr)CH | 2,5-diCH₃-4-MeO-phenyl |
| 878 | cPr—CH(CH₃) | 2,5-diCH₃-4-MeO-phenyl |
| 879 | 1-cPr—CH(CH₂CH₃) | 2,5-diCH₃-4-MeO-phenyl |
| 880 | 1-cPr—CH(CH₂CH₂CH₃) | 2,5-diCH₃-4-MeO-phenyl |
| 881 | 1-cPr—CH(CH₂OCH₃) | 2,5-diCH₃-4-MeO-phenyl |
| 882 | 1-cPr—CH(CH₂CH₂OCH₃) | 2,5-diCH₃-4-MeO-phenyl |
| 883 | (cBu)₂CH | 2,5-diCH₃-4-MeO-phenyl |
| 884 | phenyl(cBu)CH | 2,5-diCH₃-4-MeO-phenyl |
| 885 | 2-furanyl(cBu)CH | 2,5-diCH₃-4-MeO-phenyl |
| 886 | 3-furan(cBu)CH | 2,5-diCH₃-4-MeO-phenyl |
| 887 | 2-thienyl(cBu)CH | 2,5-diCH₃-4-MeO-phenyl |
| 888 | 3-thienyl(cBu)CH | 2,5-diCH₃-4-MeO-phenyl |
| 889 | 2-isoxazolyl(cBu)CH | 2,5-diCH₃-4-MeO-phenyl |
| 890 | 2-(5-CH₃-furanyl)(cBu)CH | 2,5-diCH₃-4-MeO-phenyl |
| 891 | 2-(4-CH₃-isoxazolyl)(cBu)CH | 2,5-diCH₃-4-MeO-phenyl |
| 892 | cBu—CH(CH₃) | 2,5-diCH₃-4-MeO-phenyl |
| 893 | 1-cBu—CH(CH₂CH₃) | 2,5-diCH₃-4-MeO-phenyl |
| 894 | 1-cBu—CH(CH₂CH₂CH₃) | 2,5-diCH₃-4-MeO-phenyl |
| 895 | 1-cBu—CH(CH₂OCH₃) | 2,5-diCH₃-4-MeO-phenyl |
| 896 | 1-cBu—CH(CH₂CH₂OCH₃) | 2,5-diCH₃-4-MeO-phenyl |
| 897 | (cPr)₂CH | 2-CH₃-4-MeO-5-F-phenyl |
| 898 | phenyl(cPr)CH | 2-CH₃-4-MeO-5-F-phenyl |
| 899 | 2-furanyl(cPr)CH | 2-CH₃-4-MeO-5-F-phenyl |
| 900 | 3-furan(cPr)CH | 2-CH₃-4-MeO-5-F-phenyl |
| 901 | 2-thienyl(cPr)CH | 2-CH₃-4-MeO-5-F-phenyl |
| 902 | 3-thienyl(cPr)CH | 2-CH₃-4-MeO-5-F-phenyl |
| 903 | 2-isoxazolyl(cPr)CH | 2-CH₃-4-MeO-5-F-phenyl |
| 904 | 2-(5-CH₃-furanyl)(cPr)CH | 2-CH₃-4-MeO-5-F-phenyl |
| 905 | 2-(4-CH₃-isoxazolyl)(cPr)CH | 2-CH₃-4-MeO-5-F-phenyl |
| 906 | cPr—CH(CH₃) | 2-CH₃-4-MeO-5-F-phenyl |
| 907 | 1-cPr—CH(CH₂CH₃) | 2-CH₃-4-MeO-5-F-phenyl |
| 908 | 1-cPr—CH(CH₂CH₂CH₃) | 2-CH₃-4-MeO-5-F-phenyl |
| 909 | 1-cPr—CH(CH₂OCH₃) | 2-CH₃-4-MeO-5-F-phenyl |
| 910 | 1-cPr—CH(CH₂CH₂OCH₃) | 2-CH₃-4-MeO-5-F-phenyl |
| 911 | (cBu)₂CH | 2-CH₃-4-MeO-5-F-phenyl |
| 912 | phenyl(cBu)CH | 2-CH₃-4-MeO-5-F-phenyl |
| 913 | 2-furanyl(cBu)CH | 2-CH₃-4-MeO-5-F-phenyl |
| 914 | 3-furan(cBu)CH | 2-CH₃-4-MeO-5-F-phenyl |
| 915 | 2-thienyl(cBu)CH | 2-CH₃-4-MeO-5-F-phenyl |
| 916 | 3-thienyl(cBu)CH | 2-CH₃-4-MeO-5-F-phenyl |
| 917 | 2-isoxazolyl(cBu)CH | 2-CH₃-4-MeO-5-F-phenyl |
| 918 | 2-(5-CH₃-furanyl)(cBu)CH | 2-CH₃-4-MeO-5-F-phenyl |
| 919 | 2-(4-CH₃-isoxazolyl)(cBu)CH | 2-CH₃-4-MeO-5-F-phenyl |
| 920 | cBu—CH(CH₃) | 2-CH₃-4-MeO-5-F-phenyl |
| 921 | 1-cBu—CH(CH₂CH₃) | 2-CH₃-4-MeO-5-F-phenyl |
| 922 | 1-cBu—CH(CH₂CH₂CH₃) | 2-CH₃-4-MeO-5-F-phenyl |
| 923 | 1-cBu—CH(CH₂OCH₃) | 2-CH₃-4-MeO-5-F-phenyl |
| 924 | 1-cBu—CH(CH₂CH₂OCH₃) | 2-CH₃-4-MeO-5-F-phenyl |
| 925 | (cPr)₂CH | 2,4,6-triCH₃-phenyl |
| 926 | phenyl(cPr)CH | 2,4,6-triCH₃-phenyl |
| 927 | 2-furanyl(cPr)CH | 2,4,6-triCH₃-phenyl |
| 928 | 3-furan(cPr)CH | 2,4,6-triCH₃-phenyl |
| 929 | 2-thienyl(cPr)CH | 2,4,6-triCH₃-phenyl |
| 930 | 3-thienyl(cPr)CH | 2,4,6-triCH₃-phenyl |
| 931 | 2-isoxazolyl(cPr)CH | 2,4,6-triCH₃-phenyl |
| 932 | 2-(5-CH₃-furanyl)(cPr)CH | 2,4,6-triCH₃-phenyl |
| 933 | 2-(4-CH₃-isoxazolyl)(cPr)CH | 2,4,6-triCH₃-phenyl |
| 934 | cPr—CH(CH₃) | 2,4,6-triCH₃-phenyl |
| 935 | 1-cPr—CH(CH₂CH₃) | 2,4,6-triCH₃-phenyl |
| 936 | 1-cPr—CH(CH₂CH₂CH₃) | 2,4,6-triCH₃-phenyl |
| 937 | 1-cPr—CH(CH₂OCH₃) | 2,4,6-triCH₃-phenyl |
| 938 | 1-cPr—CH(CH₂CH₂OCH₃) | 2,4,6-triCH₃-phenyl |
| 939 | (cBu)₂CH | 2,4,6-triCH₃-phenyl |
| 940 | phenyl(cBu)CH | 2,4,6-triCH₃-phenyl |
| 941 | 2-furanyl(cBu)CH | 2,4,6-triCH₃-phenyl |
| 942 | 3-furan(cBu)CH | 2,4,6-triCH₃-phenyl |
| 943 | 2-thienyl(cBu)CH | 2,4,6-triCH₃-phenyl |
| 944 | 3-thienyl(cBu)CH | 2,4,6-triCH₃-phenyl |
| 945 | 2-isoxazolyl(cBu)CH | 2,4,6-triCH₃-phenyl |
| 946 | 2-(5-CH₃-furanyl)(cBu)CH | 2,4,6-triCH₃-phenyl |
| 947 | 2-(4-CH₃-isoxazolyl)(cBu)CH | 2,4,6-triCH₃-phenyl |
| 948 | cBu—CH(CH₃) | 2,4,6-triCH₃-phenyl |

TABLE 1-continued

| | | |
|---|---|---|
| 949 | 1-cBu—CH(CH$_2$CH$_3$) | 2,4,6-triCH$_3$-phenyl |
| 950 | 1-cBu—CH(CH$_2$CH$_2$CH$_3$) | 2,4,6-triCH$_3$-phenyl |
| 951 | 1-cBu—CH(CH$_2$OCH$_3$) | 2,4,6-triCH$_3$-phenyl |
| 952 | 1-cBu—CH(CH$_2$CH$_2$OCH$_3$) | 2,4,6-triCH$_3$-phenyl |
| 953 | (cPr)$_2$CH | 3-pyridyl |
| 954 | phenyl(cPr)CH | 3-pyridyl |
| 955 | 2-furanyl(cPr)CH | 3-pyridyl |
| 956 | 3-furan(cPr)CH | 3-pyridyl |
| 957 | 2-thienyl(cPr)CH | 3-pyridyl |
| 958 | 3-thienyl(cPr)CH | 3-pyridyl |
| 959 | 2-isoxazolyl(cPr)CH | 3-pyridyl |
| 960 | 2-(5-CH$_3$-furanyl)(cPr)CH | 3-pyridyl |
| 961 | 2-(4-CH$_3$-isoxazolyl)(cPr)CH | 3-pyridyl |
| 962 | cPr—CH(CH$_3$) | 3-pyridyl |
| 963 | 1-cPr—CH(CH$_2$CH$_3$) | 3-pyridyl |
| 964 | 1-cPr—CH(CH$_2$CH$_2$CH$_3$) | 3-pyridyl |
| 965 | 1-cPr—CH(CH$_2$OCH$_3$) | 3-pyridyl |
| 966 | 1-cPr—CH(CH$_2$CH$_2$OCH$_3$) | 3-pyridyl |
| 967 | (cBu)$_2$CH | 3-pyridyl |
| 968 | phenyl(cBu)CH | 3-pyridyl |
| 969 | 2-furanyl(cBu)CH | 3-pyridyl |
| 970 | 3-furan(cBu)CH | 3-pyridyl |
| 971 | 2-thienyl(cBu)CH | 3-pyridyl |
| 972 | 3-thienyl(cBu)CH | 3-pyridyl |
| 973 | 2-isoxazolyl(cBu)CH | 3-pyridyl |
| 974 | 2-(5-CH$_3$-furanyl)(cBu)CH | 3-pyridyl |
| 975 | 2-(4-CH$_3$-isoxazolyl)(cBu)CH | 3-pyridyl |
| 976 | cBu—CH(CH$_3$) | 3-pyridyl |
| 977 | 1-cBu—CH(CH$_2$CH$_3$) | 3-pyridyl |
| 978 | 1-cBu—CH(CH$_2$CH$_2$CH$_3$) | 3-pyridyl |
| 979 | 1-cBu—CH(CH$_2$OCH$_3$) | 3-pyridyl |
| 980 | 1-cBu—CH(CH$_2$CH$_2$OCH$_3$) | 3-pyridyl |
| 981 | (cPr)$_2$CH | 2,6-diMeO-pyrid-3-yl |
| 982 | phenyl(cPr)CH | 2,6-diMeO-pyrid-3-yl |
| 983 | 2-furanyl(cPr)CH | 2,6-diMeO-pyrid-3-yl |
| 984 | 3-furan(cPr)CH | 2,6-diMeO-pyrid-3-yl |
| 985 | 2-thienyl(cPr)CH | 2,6-diMeO-pyrid-3-yl |
| 986 | 3-thienyl(cPr)CH | 2,6-diMeO-pyrid-3-yl |
| 987 | 2-isoxazolyl(cPr)CH | 2,6-diMeO-pyrid-3-yl |
| 988 | 2-(5-CH$_3$-furanyl)(cPr)CH | 2,6-diMeO-pyrid-3-yl |
| 989 | 2-(4-CH$_3$-isoxazolyl)(cPr)CH | 2,6-diMeO-pyrid-3-yl |
| 990 | cPr—CH(CH$_3$) | 2,6-diMeO-pyrid-3-yl |
| 991 | 1-cPr—CH(CH$_2$CH$_3$) | 2,6-diMeO-pyrid-3-yl |
| 992 | 1-cPr—CH(CH$_2$CH$_2$CH$_3$) | 2,6-diMeO-pyrid-3-yl |
| 993 | 1-cPr—CH(CH$_2$OCH$_3$) | 2,6-diMeO-pyrid-3-yl |
| 994 | 1-cPr—CH(CH$_2$CH$_2$OCH$_3$) | 2,6-diMeO-pyrid-3-yl |
| 995 | (cBu)$_2$CH | 2,6-diMeO-pyrid-3-yl |
| 996 | phenyl(cBu)CH | 2,6-diMeO-pyrid-3-yl |
| 997 | 2-furanyl(cBu)CH | 2,6-diMeO-pyrid-3-yl |
| 998 | 3-furan(cBu)CH | 2,6-diMeO-pyrid-3-yl |
| 999 | 2-thienyl(cBu)CH | 2,6-diMeO-pyrid-3-yl |
| 1000 | 3-thienyl(cBu)CH | 2,6-diMeO-pyrid-3-yl |
| 1001 | 2-isoxazolyl(cBu)CH | 2,6-diMeO-pyrid-3-yl |
| 1002 | 2-(5-CH$_3$-furanyl)(cBu)CH | 2,6-diMeO-pyrid-3-yl |
| 1003 | 2-(4-CH$_3$-isoxazolyl)(cBu)CH | 2,6-diMeO-pyrid-3-yl |
| 1004 | cBu—CH(CH$_3$) | 2,6-diMeO-pyrid-3-yl |
| 1005 | 1-cBu—CH(CH$_2$CH$_3$) | 2,6-diMeO-pyrid-3-yl |
| 1006 | 1-cBu—CH(CH$_2$CH$_2$CH$_3$) | 2,6-diMeO-pyrid-3-yl |
| 1007 | 1-cBu—CH(CH$_2$OCH$_3$) | 2,6-diMeO-pyrid-3-yl |
| 1008 | 1-cBu—CH(CH$_2$CH$_2$OCH$_3$) | 2,6-diMeO-pyrid-3-yl |
| 1009 | (cPr)$_2$CH | 2,6-diCH$_3$-pyrid-3-yl |
| 1010 | phenyl(cPr)CH | 2,6-diCH$_3$-pyrid-3-yl |
| 1011 | 2-furanyl(cPr)CH | 2,6-diCH$_3$-pyrid-3-yl |
| 1012 | 3-furan(cPr)CH | 2,6-diCH$_3$-pyrid-3-yl |
| 1013 | 2-thienyl(cPr)CH | 2,6-diCH$_3$-pyrid-3-yl |
| 1014 | 3-thienyl(cPr)CH | 2,6-diCH$_3$-pyrid-3-yl |
| 1015 | 2-isoxazolyl(cPr)CH | 2,6-diCH$_3$-pyrid-3-yl |
| 1016 | 2-(5-CH$_3$-furanyl)(cPr)CH | 2,6-diCH$_3$-pyrid-3-yl |
| 1017 | 2-(4-CH$_3$-isoxazolyl)(cPr)CH | 2,6-diCH$_3$-pyrid-3-yl |
| 1018 | cPr—CH(CH$_3$) | 2,6-diCH$_3$-pyrid-3-yl |
| 1019 | 1-cPr—CH(CH$_2$CH$_3$) | 2,6-diCH$_3$-pyrid-3-yl |
| 1020 | 1-cPr—CH(CH$_2$CH$_2$CH$_3$) | 2,6-diCH$_3$-pyrid-3-yl |
| 1021 | 1-cPr—CH(CH$_2$OCH$_3$) | 2,6-diCH$_3$-pyrid-3-yl |
| 1022 | 1-cPr—CH(CH$_2$CH$_2$OCH$_3$) | 2,6-diCH$_3$-pyrid-3-yl |
| 1023 | (cBu)$_2$CH | 2,6-diCH$_3$-pyrid-3-yl |
| 1024 | phenyl(cBu)CH | 2,6-diCH$_3$-pyrid-3-yl |
| 1025 | 2-furanyl(cBu)CH | 2,6-diCH$_3$-pyrid-3-yl |
| 1026 | 3-furan(cBu)CH | 2,6-diCH$_3$-pyrid-3-yl |
| 1027 | 2-thienyl(cBu)CH | 2,6-diCH$_3$-pyrid-3-yl |
| 1028 | 3-thienyl(cBu)CH | 2,6-diCH$_3$-pyrid-3-yl |
| 1029 | 2-isoxazolyl(cBu)CH | 2,6-diCH$_3$-pyrid-3-yl |
| 1030 | 2-(5-CH$_3$-furanyl)(cBu)CH | 2,6-diCH$_3$-pyrid-3-yl |
| 1031 | 2-(4-CH$_3$-isoxazolyl)(cBu)CH | 2,6-diCH$_3$-pyrid-3-yl |
| 1032 | cBu—CH(CH$_3$) | 2,6-diCH$_3$-pyrid-3-yl |
| 1033 | 1-cBu—CH(CH$_2$CH$_3$) | 2,6-diCH$_3$-pyrid-3-yl |
| 1034 | 1-cBu—CH(CH$_2$CH$_2$CH$_3$) | 2,6-diCH$_3$-pyrid-3-yl |
| 1035 | 1-cBu—CH(CH$_2$OCH$_3$) | 2,6-diCH$_3$-pyrid-3-yl |
| 1036 | 1-cBu—CH(CH$_2$CH$_2$OCH$_3$) | 2,6-diCH$_3$-pyrid-3-yl |
| 1037 | (cPr)$_2$CH | 2-CH$_3$-6-MeO-pyrid-3-yl |
| 1038 | phenyl(cPr)CH | 2-CH$_3$-6-MeO-pyrid-3-yl |
| 1039 | 2-furanyl(cPr)CH | 2-CH$_3$-6-MeO-pyrid-3-yl |
| 1040 | 3-furan(cPr)CH | 2-CH$_3$-6-MeO-pyrid-3-yl |
| 1041 | 2-thienyl(cPr)CH | 2-CH$_3$-6-MeO-pyrid-3-yl |
| 1042 | 3-thienyl(cPr)CH | 2-CH$_3$-6-MeO-pyrid-3-yl |
| 1043 | 2-isoxazolyl(cPr)CH | 2-CH$_3$-6-MeO-pyrid-3-yl |
| 1044 | 2-(5-CH$_3$-furanyl)(cPr)CH | 2-CH$_3$-6-MeO-pyrid-3-yl |
| 1045 | 2-(4-CH$_3$-isoxazolyl)(cPr)CH | 2-CH$_3$-6-MeO-pyrid-3-yl |
| 1046 | cPr—CH(CH$_3$) | 2-CH$_3$-6-MeO-pyrid-3-yl |
| 1047 | 1-cPr—CH(CH$_2$CH$_3$) | 2-CH$_3$-6-MeO-pyrid-3-yl |
| 1048 | 1-cPr—CH(CH$_2$CH$_2$CH$_3$) | 2-CH$_3$-6-MeO-pyrid-3-yl |
| 1049 | 1-cPr—CH(CH$_2$OCH$_3$) | 2-CH$_3$-6-MeO-pyrid-3-yl |
| 1050 | 1-cPr—CH(CH$_2$CH$_2$OCH$_3$) | 2-CH$_3$-6-MeO-pyrid-3-yl |
| 1051 | (cBu)$_2$CH | 2-CH$_3$-6-MeO-pyrid-3-yl |
| 1052 | phenyl(cBu)CH | 2-CH$_3$-6-MeO-pyrid-3-yl |
| 1053 | 2-furanyl(cBu)CH | 2-CH$_3$-6-MeO-pyrid-3-yl |
| 1054 | 3-furan(cBu)CH | 2-CH$_3$-6-MeO-pyrid-3-yl |
| 1055 | 2-thienyl(cBu)CH | 2-CH$_3$-6-MeO-pyrid-3-yl |
| 1056 | 3-thienyl(cBu)CH | 2-CH$_3$-6-MeO-pyrid-3-yl |
| 1057 | 2-isoxazolyl(cBu)CH | 2-CH$_3$-6-MeO-pyrid-3-yl |
| 1058 | 2-(5-CH$_3$-furanyl)(cBu)CH | 2-CH$_3$-6-MeO-pyrid-3-yl |
| 1059 | 2-(4-CH$_3$-isoxazolyl)(cBu)CH | 2-CH$_3$-6-MeO-pyrid-3-yl |
| 1060 | cBu—CH(CH$_3$) | 2-CH$_3$-6-MeO-pyrid-3-yl |
| 1061 | 1-cBu—CH(CH$_2$CH$_3$) | 2-CH$_3$-6-MeO-pyrid-3-yl |
| 1062 | 1-cBu—CH(CH$_2$CH$_2$CH$_3$) | 2-CH$_3$-6-MeO-pyrid-3-yl |
| 1063 | 1-cBu—CH(CH$_2$OCH$_3$) | 2-CH$_3$-6-MeO-pyrid-3-yl |
| 1064 | 1-cBu—CH(CH$_2$CH$_2$OCH$_3$) | 2-CH$_3$-6-MeO-pyrid-3-yl |
| 1065 | (cPr)$_2$CH | 4-CH$_3$-6-MeO-pyrid-3-yl |
| 1066 | phenyl(cPr)CH | 4-CH$_3$-6-MeO-pyrid-3-yl |
| 1067 | 2-furanyl(cPr)CH | 4-CH$_3$-6-MeO-pyrid-3-yl |
| 1068 | 3-furan(cPr)CH | 4-CH$_3$-6-MeO-pyrid-3-yl |
| 1069 | 2-thienyl(cPr)CH | 4-CH$_3$-6-MeO-pyrid-3-yl |
| 1070 | 3-thienyl(cPr)CH | 4-CH$_3$-6-MeO-pyrid-3-yl |
| 1071 | 2-isoxazolyl(cPr)CH | 4-CH$_3$-6-MeO-pyrid-3-yl |
| 1072 | 2-(5-CH$_3$-furanyl)(cPr)CH | 4-CH$_3$-6-MeO-pyrid-3-yl |
| 1073 | 2-(4-CH$_3$-isoxazolyl)(cPr)CH | 4-CH$_3$-6-MeO-pyrid-3-yl |
| 1074 | cPr—CH(CH$_3$) | 4-CH$_3$-6-MeO-pyrid-3-yl |
| 1075 | 1-cPr—CH(CH$_2$CH$_3$) | 4-CH$_3$-6-MeO-pyrid-3-yl |
| 1076 | 1-cPr—CH(CH$_2$CH$_2$CH$_3$) | 4-CH$_3$-6-MeO-pyrid-3-yl |
| 1077 | 1-cPr—CH(CH$_2$OCH$_3$) | 4-CH$_3$-6-MeO-pyrid-3-yl |
| 1078 | 1-cPr—CH(CH$_2$CH$_2$OCH$_3$) | 4-CH$_3$-6-MeO-pyrid-3-yl |
| 1079 | (cBu)$_2$CH | 4-CH$_3$-6-MeO-pyrid-3-yl |
| 1080 | phenyl(cBu)CH | 4-CH$_3$-6-MeO-pyrid-3-yl |
| 1081 | 2-furanyl(cBu)CH | 4-CH$_3$-6-MeO-pyrid-3-yl |
| 1082 | 3-furan(cBu)CH | 4-CH$_3$-6-MeO-pyrid-3-yl |
| 1083 | 2-thienyl(cBu)CH | 4-CH$_3$-6-MeO-pyrid-3-yl |
| 1084 | 3-thienyl(cBu)CH | 4-CH$_3$-6-MeO-pyrid-3-yl |
| 1085 | 2-isoxazolyl(cBu)CH | 4-CH$_3$-6-MeO-pyrid-3-yl |
| 1086 | 2-(5-CH$_3$-furanyl)(cBu)CH | 4-CH$_3$-6-MeO-pyrid-3-yl |
| 1087 | 2-(4-CH$_3$-isoxazolyl)(cBu)CH | 4-CH$_3$-6-MeO-pyrid-3-yl |
| 1088 | cBu—CH(CH$_3$) | 4-CH$_3$-6-MeO-pyrid-3-yl |
| 1089 | 1-cBu—CH(CH$_2$CH$_3$) | 4-CH$_3$-6-MeO-pyrid-3-yl |
| 1090 | 1-cBu—CH(CH$_2$CH$_2$CH$_3$) | 4-CH$_3$-6-MeO-pyrid-3-yl |
| 1091 | 1-cBu—CH(CH$_2$OCH$_3$) | 4-CH$_3$-6-MeO-pyrid-3-yl |
| 1092 | 1-cBu—CH(CH$_2$CH$_2$OCH$_3$) | 4-CH$_3$-6-MeO-pyrid-3-yl |
| 1093 | (cPr)$_2$CH | 4-CH$_3$-6-(CH$_3$)$_2$N-pyrid-3-yl |
| 1094 | phenyl(cPr)CH | 4-CH$_3$-6-(CH$_3$)$_2$N-pyrid-3-yl |
| 1095 | 2-furanyl(cPr)CH | 4-CH$_3$-6-(CH$_3$)$_2$N-pyrid-3-yl |
| 1096 | 3-furan(cPr)CH | 4-CH$_3$-6-(CH$_3$)$_2$N-pyrid-3-yl |
| 1097 | 2-thienyl(cPr)CH | 4-CH$_3$-6-(CH$_3$)$_2$N-pyrid-3-yl |
| 1098 | 3-thienyl(cPr)CH | 4-CH$_3$-6-(CH$_3$)$_2$N-pyrid-3-yl |
| 1099 | 2-isoxazolyl(cPr)CH | 4-CH$_3$-6-(CH$_3$)$_2$N-pyrid-3-yl |
| 1100 | 2-(5-CH$_3$-furanyl)(cPr)CH | 4-CH$_3$-6-(CH$_3$)$_2$N-pyrid-3-yl |
| 1101 | 2-(4-CH$_3$-isoxazolyl)(cPr)CH | 4-CH$_3$-6-(CH$_3$)$_2$N-pyrid-3-yl |
| 1102 | cPr—CH(CH$_3$) | 4-CH$_3$-6-(CH$_3$)$_2$N-pyrid-3-yl |
| 1103 | 1-cPr—CH(CH$_2$CH$_3$) | 4-CH$_3$-6-(CH$_3$)$_2$N-pyrid-3-yl |
| 1104 | 1-cPr—CH(CH$_2$CH$_2$CH$_3$) | 4-CH$_3$-6-(CH$_3$)$_2$N-pyrid-3-yl |
| 1105 | 1-cPr—CH(CH$_2$OCH$_3$) | 4-CH$_3$-6-(CH$_3$)$_2$N-pyrid-3-yl |
| 1106 | 1-cPr—CH(CH$_2$CH$_2$OCH$_3$) | 4-CH$_3$-6-(CH$_3$)$_2$N-pyrid-3-yl |

TABLE 1-continued

| | |
|---|---|
| 1107 (cBu)₂CH | 4-CH₃-6-(CH₃)₂N-pyrid-3-yl |
| 1108 phenyl(cBu)CH | 4-CH₃-6-(CH₃)₂N-pyrid-3-yl |
| 1109 2-furanyl(cBu)CH | 4-CH₃-6-(CH₃)₂N-pyrid-3-yl |
| 1110 3-furan(cBu)CH | 4-CH₃-6-(CH₃)₂N-pyrid-3-yl |
| 1111 2-thienyl(cBu)CH | 4-CH₃-6-(CH₃)₂N-pyrid-3-yl |
| 1112 3-thienyl(cBu)CH | 4-CH₃-6-(CH₃)₂N-pyrid-3-yl |
| 1113 2-isoxazolyl(cBu)CH | 4-CH₃-6-(CH₃)₂N-pyrid-3-yl |
| 1114 2-(5-CH₃-furanyl)(cBu)CH | 4-CH₃-6-(CH₃)₂N-pyrid-3-yl |
| 1115 2-(4-CH₃-isoxazolyl)(cBu)CH | 4-CH₃-6-(CH₃)₂N-pyrld-3-yl |
| 1116 cBu—CH(CH₃) | 4-CH₃-6-(CH₃)₂N-pyrid-3-yl |
| 1117 1-cBu—CH(CH₂CH₃) | 4-CH₃-6-(CH₃)₂N-pyrid-3-yl |
| 1118 1-cBu—CH(CH₂CH₂CH₃) | 4-CH₃-6-(CH₃)₂N-pyrid-3-yl |
| 1119 1-cBu—CH(CH₂OCH₃) | 4-CH₃-6-(CH₃)₂N-pyrid-3-yl |
| 1120 1-cBu—CH(CH₂CH₂OCH₃) | 4-CH₃-6-(CH₃)₂N-pyrid-3-yl |
| 1121 3-pentyl | 2,4,6-(CH₃)₃ phenyl |
| 1122 3-pentyl | 2,4-Cl₂-5-F-phenyl |
| 1123 3-pentyl | 2,4-(MEO)₂-phenyl |
| 1124 3-pentyl | 2,4-Cl₂-phenyl |
| 1 3-pentyl | 2,4-Cl₂-phenyl |

Table 1 shows compounds which may readily be prepared according to the procedures described herein in the synthetic schemes and text. The preferred compounds have a core of $e_4$ with the exception of Examples 95 and 1124, which have cores of $c_4$ and $f_4$ respectively. Example 1 has a melting point of 136–138° C.

Utility

Compounds of this invention are expected to have utility in the treatment of inbalances associated with abnormal levels of CRF in patients suffering from depression, affective disorders, and/or anxiety.

CRF-R1 Receptor Binding Assay for the Evaluation of Biological Activity

The following is a description of the isolation of cell membranes containing cloned human CRF-R1 receptors for use in the standard binding assay as well as a description of the assay itself.

Messenger RNA was isolated from human hippocampus. The mRNA was reverse transcribed using oligo (dt) 12–18 and the coding region was amplified by PCR from start to stop codons The resulting PCR fragment was cloned into the EcoRV site of PGEMV, from whence the insert was reclaimed using XhoI+XbaI and cloned into the XhoI+XbaI sites of vector pm3ar (which contains a CMV promoter, the SV40 't' splice and early poly A signals, an Epstein-Barr viral origin of replication, and a hygromycin selectable marker). The resulting expression vector, called phchCRFR was transfected in 293EBNA cells and cells retaining the episome were selected in the presence of 400 µM hygromycin. Cells surviving 4 weeks of selection in hygromycin were pooled, adapted to growth in suspension and used to generate membranes for the binding assay described below. Individual aliquots containing approximately 1×10⁸ of the suspended cells were then centrifuged to form a pellet and frozen.

For the binding assay a frozen pellet described above containing 293EBNA cells transfected with hCRFR1 receptors is homogenized in 10 ml of ice cold tissue buffer (50 mM HEPES buffer pH 7.0, containing 10 mM MgCl₂, 2 mM EGTA, 1 µg/l aprotinin, 1 µg/ml leupeptin and 1 µg/ml pepstatin). The homogenate is centrifuged at 40,000×g for 12 min and the resulting pellet rehomogenized in 10 ml of tissue buffer. After another centrifugation at 40,000×g for 12 min, the pellet is resuspended to a protein concentration of 360 µg/ml to be used in the assay.

Binding assays are performed in 96 well plates; each well having a 300 µl capacity. To each well is added 50 µl of test drug dilutions (final concentration of drugs range from $10^{-10}$–$10^{-5}$ M), 100 µl of $^{125}$I-ovine-CRF ($^{125}$I-o-CRF) (final concentration 150 pM) and 150 µl of the cell homogenate described above. Plates are then allowed to incubate at room temperature for 2 hours before filtering the incubate over GF/F filters (presoaked with 0.3% polyethyleneimine) using an appropriate cell harvester. Filters are rinsed 2 times with ice cold assay buffer before removing individual filters and assessing them for radioactivity on a gamma counter.

Curves of the inhibition of $^{125}$I-o-CRF binding to cell membranes at various dilutions of test drug are analyzed by the iterative curve fitting program LIGAND [P. J. Munson and D. Rodbard, Anal. Biochem. 107:220 (1980)], which provides Ki values for inhibition which are then used to assess biological activity.

A compound is considered to be active if it has a $K_i$ value of less than about 10000 nM for the inhibition of CRF.

Alternatively, tissues and cells which naturally express CRF receptors can be employed in binding assays analogous to those described above.

Inhibition of CRF-Stimulated Adenylate Cyclase Activity

Inhibition of CRF-stimulated adenylate cyclase activity can be performed as described by G. Battaglia et al. Synapse 1:572 (1987). Briefly, assays are carried out at 37° C. for 10 min in 200 ml of buffer containing 100 mM Tris-HCl (pH 7.4 at 37° C.), 10 mM MgCl₂, 0.4 mM EGTA, 0.1% BSAI 1 mM isobutylmethylxanthine (IBMX), 250 units/ml phosphocreatine kinase, 5 mM creatine phosphate, 100 mM guanosine 5'-triphosphate, 100 nM oCRF, antagonist peptides (concentration range $10^{-9}$ to $10^{-6m}$) and 0.8 mg original wet weight tissue (approximately 40–60 mg protein). Reactions are initiated by the addition of 1 mM ATP/[$^{32}$P] ATP (approximately 2–4 mCi/tube) and terminated by the addition of 100 ml of 50 mM Tris-HCL, 45 mM ATP and 2% sodium dodecyl sulfate. In order to monitor the recovery of CAMP, 1 µl of [³H]cAMP (approximately 40,000 dpm) is added to each tube prior to separation. The separation of [$^{32}$P]cAMP from [$^{32}$P]ATP is performed by sequential elution over Dowex and alumina columns.

In vivo Biological Assay

The in vivo activity of the compounds of the present invention can be assessed using any one of the biological assays available and accepted within the art. Illustrative of these tests include the Acoustic-Startle Assay, the Stair Climbing Test, and the Chronic Administration Assay. These and other models useful for the testing of compounds of the present invention have been outlined in C. W. Berridge and A. J. Dunn Brain Research Reviews 15:71 (1990). Compounds may be tested in any species of rodent or small mammal.

Dosage and Formulation

Compounds of this invention can be administered to treat these abnormalities by means that produce contact of the active agent with the agent's site of action in the body of a mammal. The compounds can be administered by any conventional means available for use in conjunction with pharmaceuticals either as individual therapeutic agent or in combination of therapeutic agents. They can be administered alone, but will generally be administered with a pharmaceutical carrier selected on the basis of the chosen route of administration and standard pharmaceutical practice.

The dosage administered will vary depending on the use and known factors such as pharmacodynamic character of the particular agent, and its mode and route of administration; the recipient's age, weight, and health; nature and extent of symptoms; kind of concurrent treatment; frequency of treatment; and desired effect. For use in the treatment of said diseases or conditions, the compounds of this invention can be orally administered daily at a dosage of the active ingredient of 0.002 to 200 mg/kg of body weight. Ordinarily, a dose of 0.01 to 10 mg/kg in divided doses one to four times a day, or in sustained release formulation will be effective in obtaining the desired pharmacological effect.

Dosage forms (compositions) suitable for administration contain from about 1 mg to about 100 mg of active ingredient per unit. In these pharmaceutical compositions, the active ingredient will ordinarily be present in an amount of about 0.5 to 95% by weight based on the total weight of the composition.

The active ingredient can be administered orally is solid dosage forms, such as capsules, tablets and powders; or in liquid forms such as elixirs, syrups, and/or suspensions. The compounds of this invention can also be administered parenterally in sterile liquid dose formulations.

Gelatin capsules can be used to contain the active ingredient and a suitable carrier such as but not limited to lactose, starch, magnesium stearate, steric acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract.

Liquid dose forms for oral administration can contain coloring or flavoring agents to increase patient acceptance.

In general, water, pharmaceutically acceptable oils, saline, aqueous dextrose (glucose), and related sugar solutions and glycols, such as propylene glycol or polyethylene glycol, are suitable carriers for parenteral solutions. Solutions for parenteral administration preferably contain a water soluble salt of the active ingredient, suitable stabilizing agents, and if necessary, butter substances. Antioxidizing agents, such as sodium bisulfite, sodium sulfite, or ascorbic acid, either alone or in combination, are suitable stabilizing agents. Also used are citric acid and its salts, and EDTA. In addition, parenteral solutions can contain preservatives such as benzalkonium chloride, methyl- or propyl-paraben, and chlorobutanol.

Suitable pharmaceutical carriers are described in "Remington's Pharmaceutical Sciences", A. Osol, a standard reference in the field.

Useful pharmaceutical dosage-forms for administration of the compounds of this invention can be illustrated as follows:

Capsules

A large number of units capsules are prepared by filling standard two-piece hard gelatin capsules each with 100 mg of powdered active ingredient, 150 mg lactose, 50 mg cellulose, and 6 mg magnesium stearate.

Soft Gelatin Capsules

A mixture of active ingredient in a digestible oil such as soybean, cottonseed oil, or olive oil is prepared and injected by means of a positive displacement was pumped into gelatin to form soft gelatin capsules containing 100 mg of the active ingredient. The capsules were washed and dried.

Tablets

A large number of tablets are prepared by conventional procedures so that the dosage unit was 100 mg active ingredient, 0.2 mg of colloidal silicon dioxide, 5 mg of magnesium stearate, 275 mg of microcrystalline cellulose, 11 mg of starch, and 98.8 mg lactose. Appropriate coatings may be applied to increase palatability or delayed adsorption.

The compounds of this invention may also be used as reagents or standards in the biochemical study of neurological function, dysfunction, and disease.

Obviously, numerous modifications and variations of the present invention are possible in light of the above teachings. It is therefore to be understood that within the scope of the appended claims, the invention may be practiced otherwise that as specifically described herein.

What is claimed as new and desired to be secured by Letter Patent of United States is:

1. A compound of formula (Ia):

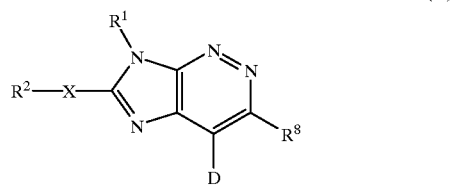

(Ia)

or a stereoisomer or pharmaceutically acceptable salt form thereof, wherein:

D is an aryl or heteroaryl group attached through an unsaturated carbon atom;

X is selected from the group CH—$R^9$, N—$R^{10}$, O, S(O)$_n$ and a bond;

n is 0, 1 or 2;

$R^1$ is selected from the group $C_{1-10}$ alkyl, $C_{2-10}$ alkenyl, $C_{2-10}$ alkynyl, $C_{3-8}$ cycloalkyl, $C_{3-6}$ cycloalkyl-$C_{1-6}$ alkyl, $C_{1-4}$ alkoxy-$C_{1-4}$ alkyl, —$SO_2$—$C_{1-10}$ alkyl, —$SO_2$—$R^{1a}$, and —$SO_2$—$R^{1b}$;

$R^1$ is substituted with 0–1 substituents selected from the group —CN, —S(O)$_n R^{14b}$, —COR$^{13a}$, —CO$_2 R^{13a}$, —NR$^{15a}$COR$^{13a}$, —N(COR$^{13a}$)$_2$, —NR$^{15a}$CONR$^{13a}R^{16a}$, —NR$^{15a}$CO$_2 R^{14b}$, —CONR$^{13a}R^{16a}$, 1-morpholinyl, 1-piperidinyl, 1-piperazinyl, and $C_{3-8}$ cycloalkyl, wherein 0–1 carbon atoms in the $C_{4-8}$ cycloalkyl is replaced by a group selected from the group —O—, —S(O)$_n$—, —NR$^{13a}$—, —NCO$_2 R^{14b}$—, —NCOR$^{14b}$— and —NSO$_2 R^{14b}$—, and wherein $N_4$ in 1-piperazinyl is substituted with 0–1 substituents selected from the group $R^{13a}$, CO$_2 R^{14b}$, COR$^{14b}$ and SO$_2 R^{14b}$;

$R^1$ is also substituted with 0–3 substituents independently selected at each occurrence from the group $R^{1a}$, $R^{1b}$, $R^{1c}$, $C_{1-6}$ alkyl, $C_{2-8}$ alkenyl, $C_{2-8}$ alkynyl, Br, Cl, F, I, $C_{1-4}$ haloalkyl, —OR$^{13a}$, —NR$^{13a}R^{16a}$, $C_{1-4}$ alkoxy-$C_{1-4}$ alkyl, and $C_{3-8}$ cycloalkyl which is substituted with 0–1 $R^9$ and in which 0–1 carbons of $C_{4-8}$ cycloalkyl is replaced by —O—;

provided that $R^1$ is other than a cyclohexyl-(CH$_2$)$_2$— group;

$R^{1a}$ is aryl and is selected from the group phenyl, naphthyl, indanyl and indenyl, each $R^{1a}$ being substituted with 0–1 —$OR^{17}$ and 0–5 substituents independently selected at each occurrence from the group $C_{1-6}$ alkyl, $C_{3-6}$ cycloalkyl, Br, Cl, F, I, $C_{1-4}$ haloalkyl, —CN, nitro, SH, —$S(O)_nR^{18}$, —$COR^{17}$, —$OC(O)R^{18}$, $NR^{15a}COR^{17}$, —$N(COR^{17})_2$, —$NR^{15a}CONR^{17a}R^{19a}$, —$NR^{15a}CO_2R^{18}$, —$NR^{17a}R^{19a}$, and —$CONR^{17a}R^{19a}$;

$R^{1b}$ is heteroaryl and is selected from the group pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, pyrazolyl, triazolyl, tetrazolyl, indazolyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, benzoxazolin-2-onyl, benzodioxolanyl and benzodioxane, each heteroaryl being substituted on 0–4 carbon atoms with a substituent independently selected at each occurrence from the group $C_{1-6}$ alkyl, $C_{3-6}$ cycloalkyl, Br, Cl, F, I, $C_{1-4}$ haloalkyl, —CN, nitro, —$OR^{17}$, SH, —$S(O)_mR^{18}$, —$COR^{17}$, —$OC(O)R^{18}$, $NR^{15a}COR^{17}$, —$N(COR^{17})_2$, —$NR^{15a}CONR^{17a}R^{19a}$, —$NR^{15a}CO_2R^{18}$, —$NR^{17a}R^{19a}$, and —$CONR^{17a}R^{19a}$, and each heteroaryl being substituted on any nitrogen atom with 0–1 substituents selected from the group $R^{15a}$, $CO_2R^{14b}$, $COR^{14b}$ and $SO_2R^{14b}$;

$R^{1c}$ is heterocyclyl and is a saturated or partially saturated heteroaryl, each heterocyclyl being substituted on 0–4 carbon atoms with a substituent independently selected at each occurrence from the group $C_{1-6}$ alkyl, $C_{3-6}$ cycloalkyl, Br, Cl, F, I, $C_{1-4}$ haloalkyl, —CN, nitro, —$OR^{13a}$, SH, —$S(O)_nR^{14b}$, —$COR^{13a}$, —$OC(O)R^{14b}$, —$NR^{15a}COR^{13a}$, —$N(COR^{13a})_2$, —$NR^{15a}CONR^{13a}R^{16a}$, —$NR^{15a}CO_2R^{14b}$, —$NR^{13a}R^{16a}$, and —$CONR^{13a}R^{16a}$ and each heterocyclyl being substituted on any nitrogen atom with 0–1 substituents selected from the group $R^{13a}$, $CO_2R^{14b}$, $COR^{14b}$ and $SO_2R^{14b}$ and wherein any sulfur atom is optionally monooxidized or dioxidized;

provided that $R^1$ is other than a —$(CH_2)_{1-4}$-aryl, —$(CH_2)_{1-4}$-heteroaryl, or —$(CH_2)_{1-4}$-heterocycle, wherein the aryl, heteroaryl, or heterocycle group is substituted or unsubstituted;

$R^2$ is selected from the group $C_{1-4}$ alkyl, $C_{3-8}$ cycloalkyl, $C_{2-4}$ alkenyl, and $C_{2-4}$ alkynyl and is substituted with 0–3 substituents selected from the group —CN, hydroxy, halo and $C_{1-4}$ alkoxy;

alternatively $R^2$, in the case where X is a bond, is selected from the group —CN, $CF_3$ and $C_2F_5$;

$R^8$ is independently selected at each occurrence from the group H, Br, Cl, F, I, —CN, $C_{1-4}$ alkyl, $C_{3-8}$ cycloalkyl, $C_{1-4}$ alkoxy, $C_{1-4}$ alkylthio, $C_{1-4}$ alkylsulfinyl, $C_{1-4}$ alkylsulfonyl, amino, $C_{1-4}$ alkylamino, $(C_{1-4}$ alkyl$)_2$amino and phenyl, each phenyl is substituted with 0–3 groups selected from the group $C_{1-7}$ alkyl, $C_{3-8}$ cycloalkyl, Br, Cl, F, I, $C_{1-4}$ haloalkyl, nitro, $C_{1-4}$ alkoxy, $C_{1-4}$ haloalkoxy, $C_{1-4}$ alkylthio, $C_{1-4}$ alkyl sulfinyl, $C_{1-4}$ alkylsulfonyl, $C_{1-6}$ alkylamino and $(C_{1-4}$ alkyl$)_2$amino; p1 $R^9$ and $R^{10}$ are independently selected at each occurrence from the group H, $C_{1-4}$ alkyl, $C_{3-6}$ cycloalkyl-$C_{1-4}$ alkyl and $C_{3-8}$ cycloalkyl;

$R^{13}$ is selected from the group H, $C_{1-4}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl, aryl, aryl$(C_{1-4}$ alkyl)—, heteroaryl and heteroaryl$(C_{1-4}$ alkyl)—;

$R^{13a}$ and $R^{16a}$ are independently selected at each occurrence from the group H, $C_{1-4}$ alkyl, $C_{1-4}$ haloalkyl, $C_{1-4}$ alkoxy-$C_{1-4}$ alkyl, $C_{3-6}$ cycloalkyl, and $C_{3-6}$ cycloalkyl-$C_{1-6}$ alkyl;

$R^{14}$ is selected from the group $C_{1-4}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl, aryl, aryl$(C_{1-4}$ alkyl)—, heteroaryl and heteroaryl$(C_{1-4}$ alkyl)— and benzyl, each benzyl being substituted on the aryl moiety with 0–1 substituents selected from the group $C_{1-4}$ alkyl, Br, Cl, F, I, $C_{1-4}$ haloalkyl, nitro, $C_{1-4}$ alkoxy $C_{1-4}$ haloalkoxy, and dimethylamino;

$R^{14a}$ is selected from the group $C_{1-4}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl and benzyl, each benzyl being substituted on the aryl moiety with 0–1 substituents selected from the group $C_{1-4}$ alkyl, Br, Cl, F, I, $C_{1-4}$ haloalkyl, nitro, $C_{1-4}$ alkoxy, $C_{1-4}$ haloalkoxy, and dimethylamino;

$R^{14b}$ is selected from the group $C_{1-4}$ alkyl, $C_{1-4}$ haloalkyl, $C_{1-4}$ alkoxy-$C_{1-4}$ alkyl, $C_{3-6}$ cycloalkyl, and $C_{3-6}$ cycloalkyl-$C_{1-6}$ alkyl;

$R^{15}$ is independently selected at each occurrence from the group H, $C_{1-4}$ alkyl, $C_{3-7}$ cycloalkyl, $C_{3-6}$ cycloalkyl-$C_{1-6}$ alkyl, phenyl and benzyl, each phenyl or benzyl being substituted on the aryl moiety with 0–3 groups chosen from the group $C_{1-4}$ alkyl, Br, Cl, F, I, $C_{1-4}$ haloalkyl, nitro, $C_{1-4}$ alkoxy, $C_{1-4}$ haloalkoxy, and dimethylamino;

$R^{15a}$ is independently selected at each occurrence from the group H, $C_{1-4}$ alkyl, $C_{3-7}$ cycloalkyl, and $C_{3-6}$ cycloalkyl-$C_{1-6}$ alkyl;

$R^{17}$ is selected at each occurrence from the group H, $C_{1-6}$ alkyl, $C_{3-10}$ cycloalkyl, $C_{3-6}$ cycloalkyl-$C_{1-6}$ alkyl, $C_{1-2}$ alkoxy-$C_{1-2}$ alkyl, $C_{1-4}$ haloalkyl, $R^{14}S(O)_n$—$C_{1-4}$ alkyl, and $R^{17b}R^{19b}N$—$C_{2-4}$ alkyl;

$R^{18}$ and $R^{19}$ are independently selected at each occurrence from the group H, $C_{1-6}$ alkyl, $C_{3-10}$ cycloalkyl, $C_{3-6}$ cycloalkyl-$C_{1-6}$ alkyl, $C_{1-2}$ alkoxy-$C_{1-2}$ alkyl, and $C_{1-4}$ haloalkyl;

alternatively, in an $NR^{17}R^{19}$ moiety, $R^{17}$ and $R^{19}$ taken together form 1-pyrrolidinyl, 1-morpholinyl, 1-piperidinyl or 1-piperazinyl, wherein $N_4$ in 1-piperazinyl is substituted with 0–1 substituents selected from the group $R^{13}$, $CO_2R^{14}$, $COR^{14}$ and $SO_2R^{14}$;

alternatively, in an $NR^{17b}R^{19b}$ moiety, $R^{17b}$ and $R^{19b}$ taken together form 1-pyrrolidinyl, 1-morpholinyl, 1-piperidinyl or 1-piperazinyl, wherein $N_4$ in 1-piperazinyl is substituted with 0–1 substituents selected from the group $R^{13}$, $CO_2R^{14}$, $COR^{14}$ and $SO_2R^{14}$;

$R^{17a}$ and $R^{19a}$ are independently selected at each occurrence from the group H, $C_{1-6}$ alkyl, $C_{3-10}$ cycloalkyl, $C_{3-6}$ cycloalkyl-$C_{1-6}$ alkyl and $C_{1-4}$ haloalkyl;

aryl is independently selected at each occurrence from the group phenyl, naphthyl, indanyl and indenyl, each aryl being substituted with 0–5 substituents independently selected at each occurrence from the group $C_{1-6}$ alkyl, $C_{3-6}$ cycloalkyl, methylenedioxy, $C_{1-4}$ alkoxy-$C_{1-4}$ alkoxy, —$OR^{17}$, Br, Cl, F, I, $C_{1-4}$ haloalkyl, —CN, —$NO_2$, SH, —$S(O)_nR^{18}$, —$COR^{17}$, —$CO_2R^{17}$, —OC (O)R$^{18}$, —NR$^{15}$COR$^{17}$, —N(COR$^{17}$)$_2$, —NR$^{15}$CONR$^{17}$R$^{19}$, —NR$^{15}$CO$_2$R$^{18}$, —NR$^{17}$R$^{19}$, and —CONR$^{17}$R$^{19}$ and up to 1 phenyl, each phenyl substituent being substituted with 0–4 substituents selected from the group C$_{1-3}$ alkyl, C$_{1-3}$ alkoxy, Br, Cl, F, I, —CN, dimethylamino, CF$_3$, C$_2$F$_5$, OCF$_3$, SO$_2$Me and acetyl;

heteroaryl is independently selected at each occurence from the group pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, triazolyl, tetrazolyl, indazolyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, benzoxazolin-2-on-yl, benzodioxolanyl and benzodioxane, each heteroaryl being substituted 0–4 carbon atoms with a substituent independently selected at each occurrence from the group C$_{1-6}$ alkyl, C$_{3-6}$ cycloalkyl, Br, Cl, F, I, C$_{1-4}$ haloalkyl, —CN, nitro, —OR$^{17}$, SH, —S(O)$_n$R$^{18}$, —COR$^{17}$, —CO$_2$R$^{17}$, —OC(O)R$^{18}$, —NR$^{15}$COR$^{17}$, —N(COR$^{17}$)$_2$, —NR$^{15}$CONR$^{17}$R$^{19}$, —NR$^{15}$CO$_2$R$^{18}$, —NR$^{17}$R$^{19}$, and —CONR$^{17}$R$^{19}$ and each heteroaryl being substituted on any nitrogen atom with 0–1 substituents selected from the group R$^{15}$, CO$_2$R$^{14a}$, COR$^{14a}$ and SO$_2$R$^{14a}$; and, provided that when D is imidazole or triazole, R$^1$ is other than unsubstituted C$_{1-6}$ linear or branched alkyl or C$_{3-6}$ cycloalkyl.

2. A pharmaceutical composition comprising a pharmaceutically acceptable carrier and a therapeutically effective amount of a compound of claim 1.

3. A method of treating affective disorder, anxiety, depression, headache, irritable bowel syndrome, post-traumatic stress disorder, supranuclear palsy, immune suppression, Alzheimer's disease, gastrointestinal diseases, anorexia nervosa, drug addiction, drug or alcohol withdrawal symptoms, inflammatory diseases, cardiovascular or heart-related diseases, human immunodeficiency virus infections, hemorrhagic stress, obesity, infertility, head and spinal cord traumas, epilepsy, stroke, ulcers, amyotrophic lateral sclerosis, hypoglycemia or a disorder the treatment of which can be effected or facilitated, by antagonizing CRF, in mammals, comprising: administering to the mammal in need of such treatment a therapeutically effective amount of a compound of claim 1.

4. A method of treating affective disorder, anxiety, depression, headache, irritable bowel syndrome, post-traumatic stress disorder, supranuclear palsy, immune suppression, Alzheimer's disease, gastrointestinal diseases, anorexia nervosa, drug addiction, drug or alcohol withdrawal symptoms, inflammatory diseases, cardiovascular or heart-related diseases, human immunodeficiency virus infections, hemorrhagic stress, obesity, infertility, head and spinal cord traumas, epilepsy, stroke, ulcers, amyotrophic lateral sclerosis, hypoglycemia or a disorder the treatment of which can be effected or facilitated by antagonizing CRF, in mammals, comprising: administering to the mammal in need of such treatment a therapeutically effective amount of a compound of formula (I):

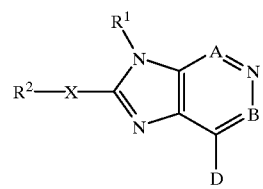

(I)

or a stereoisomer or pharmaceutically acceptable salt form thereof, wherein:

A is N or C—R$^7$;

B is N or C—R$^8$;

provided that when A is N that B must be C—R$^8$, and that when B is N that A must be C—R$^7$;

D is an aryl or heteroaryl group attached through an unsaturated carbon atom;

X is selected from the group CH—R$^9$, N—R$^{10}$, O, S(O)$_n$ and a bond;

n is 0, 1 or 2;

R$^1$ is selected from the group C$_{1-10}$ alkyl, C$_{2-10}$ alkenyl, C$_{2-10}$ alkynyl, C$_{3-8}$ cycloalkyl, C$_{3-6}$ cycloalkyl-C$_{1-6}$ alkyl, C$_{1-4}$ alkoxy-C$_{1-4}$ alkyl, —SO$_2$—C$_{1-10}$ alkyl, —SO$_2$—R$^{1a}$, and —SO$_2$—R$^{1b}$;

R$^1$ is substituted with 0–1 substituents selected from the group —CN, —S(O)$_n$R$^{14b}$, —COR$^{13a}$, —CO$_2$R$^{13a}$, —NR$^{15a}$COR$^{13a}$, —N(COR$^{13a}$)$_2$, —NR$^{15a}$CONR$^{13a}$R$^{16a}$, —NR$^{15a}$CO$_2$R$^{14b}$, —CONR$^{13a}$R$^{16a}$, 1-morpholinyl, 1-piperidinyl, 1-piperazinyl, and C$_{3-8}$ cycloalkyl, wherein 0–1 carbon atoms in the C$_{4-8}$ cycloalkyl is replaced by a group selected from the group —O—, —S(O)$_n$—, —NR$^{13a}$—, —NCO$_2$R$^{14b}$—, —NCOR$^{14b}$— and —NSO$_2$R$^{14b}$—, and wherein N$_4$ in 1-piperazinyl is substituted with 0–1 substituents selected from the group R$^{13a}$, CO$_2$R$^{14b}$, COR$^{14b}$ and SO$_2$R$^{14b}$;

R1 is also substituted with 0–3 substituents independently selected at each occurrence from the group R$^{1a}$, R$^{1b}$, R$^{1c}$, C$_{1-6}$ alkyl, C$_{2-8}$ alkenyl, C$_{2-8}$ alkynyl, Br, Cl, F, I, C$_{1-4}$ haloalkyl, —OR$^{13a}$, —NR$^{13a}$R$^{16a}$, C$_{1-4}$ alkoxy-C$_{1-4}$ alkyl, and C$_{3-8}$ cycloalkyl which is substituted with 0–1 R$^9$ and in which 0–1 carbons of C$_{4-8}$ cycloalkyl is replaced by —O—;

R$^{1a}$ is aryl and is selected from the group phenyl, naphthyl, indanyl and indenyl, each R$^{1a}$ being substituted with 0–5 substituents independently selected at each occurrence from the group C$_{1-6}$ alkyl, C$_{3-6}$ cycloalkyl, Br, Cl, F, I, C$_{1-4}$ haloalkyl, —CN, nitro, —OR$^{17}$, SH, —S(O)$_n$R$^{18}$, —COR$^{17}$, —OC(O)R$^{18}$, —NR$^{15a}$COR$^{17}$, —N(COR$^{17}$)$_2$, —NR$^{15a}$CONR$^{17a}$R$^{19a}$, —NR$^{15a}$CO$_2$R$^{18}$, —NR$^{17a}$R$^{19a}$, and —CONR$^{17a}$R$^{19a}$;

R$^{1b}$ is heteroaryl and is selected from the group pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, pyrazolyl, triazolyl, tetrazolyl, indazolyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, benzoxazolin-2-onyl, benzodioxolanyl and benzodioxane, each heteroaryl being substituted on 0–4 carbon atoms with a substituent independently selected at each occurrence from the group $C_{1-6}$ alkyl, $C_{3-6}$ cycloalkyl, Br, Cl, F, I, $C_{1-4}$ haloalkyl, —CN, nitro, —$OR^{17}$, SH, —$S(O)_mR^{18}$, —$COR^{17}$, —$OC(O)R^{18}$, —$NR^{15a}COR^{17}$, —$N(COR^{17})_2$, —$NR^{15a}CONR^{17a}R^{19a}$, —$NR^{15a}CO_2R^{18}$, —$NR^{17a}R^{19a}$, and —$CONR^{17a}R^{19a}$ and each heteroaryl being substituted on any nitrogen atom with 0–1 substituents selected from the group $R^{15a}$, $CO_2R^{14b}$, $COR^{14b}$ and $SO_2R^{14b}$;

$R^{1c}$ is heterocyclyl and is a saturated or partially saturated heteroaryl, each heterocyclyl being substituted on 0–4 carbon atoms with a substituent independently selected at each occurrence from the group $C_{1-6}$ alkyl, $C_{3-6}$ cycloalkyl, Br, Cl, F, I, $C_{1-4}$ haloalkyl, —CN, nitro, —$OR^{13a}$, SH, —$S(O)_nR^{14b}$, —$COR^{13a}$, —$OC(O)R^{14b}$, —$NR^{15a}COR^{13a}$, —$N(COR^{13a})_2$, —$NR^{15a}CONR^{13a}R^{16a}$, —$NR^{15a}CO_2R^{14b}$, —$NR^{13a}R^{16a}$, and —$CONR^{13a}R^{16a}$ and each heterocyclyl being substituted on any nitrogen atom with 0–1 substituents selected from the group $R^{13a}$, $CO_2R^{14b}$, $COR^{14b}$ and $SO_2R^{14b}$ and wherein any sulfur atom is optionally monooxidized or dioxidized;

$R^2$ is selected from the group $C_{1-4}$ alkyl, $C_{3-8}$ cycloalkyl, $C_{2-4}$ alkenyl, and $C_{2-4}$ alkynyl and is substituted with 0–3 substituents selected from the group —CN, hydroxy, halo and $C_{1-4}$ alkoxy;

alternatively $R^2$, in the case where X is a bond, is selected from the group —CN, $CF_3$ and $C_2F_5$;

$R^7$ and $R^8$ are independently selected at each occurrence from the group H, Br, Cl, F, I, —CN, $C_{1-4}$ alkyl, $C_{3-8}$ cycloalkyl, $C_{1-4}$ alkoxy, $C_{1-4}$ alkylthio, $C_{1-4}$ alkylsulfinyl, $C_{1-4}$ alkylsulfonyl, amino, $C_{1-4}$ alkylamino, ($C_{1-4}$ alkyl)$_2$amino and phenyl, each phenyl is substituted with 0–3 groups selected from the group $C_{1-7}$ alkyl, $C_{3-8}$ cycloalkyl, Br, Cl, F, I, $C_{1-4}$ haloalkyl, nitro, $C_{1-4}$ alkoxy, $C_{1-4}$ haloalkoxy, $C_{1-4}$ alkylthio, $C_{1-4}$ alkyl sulfinyl, $C_{1-4}$ alkylsulfonyl, $C_{1-6}$ alkylamino and ($C_{1-4}$ alkyl)$_2$amino;

$R^9$ and $R^{10}$ are independently selected at each occurrence from the group H, $C_{1-4}$ alkyl, $C_{3-6}$ cycloalkyl-$C_{1-4}$ alkyl and $C_{3-8}$ cycloalkyl;

$R^{13}$ is selected from the group H, $C_{1-4}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl, aryl, aryl($C_{1-4}$ alkyl)-, heteroaryl and heteroaryl($C_{1-4}$ alkyl)-;

$R^{13a}$ and $R^{16a}$ are independently selected at each occurrence from the group H, $C_{1-4}$ alkyl, $C_{1-4}$ haloalkyl, $C_{1-4}$ alkoxy-$C_{1-4}$ alkyl, $C_{3-6}$ cycloalkyl, and $C_{3-6}$ cycloalkyl-$C_{1-6}$ alkyl;

$R^{14}$ is selected from the group $C_{1-4}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl, aryl, aryl($C_{1-4}$ alkyl)—, heteroaryl and heteroaryl($C_{1-4}$ alkyl)— and benzyl, each benzyl being substituted on the aryl moiety with 0–1 substituents selected from the group $C_{1-4}$ alkyl, Br, Cl, F, I, $C_{1-4}$ haloalkyl, nitro, $C_{1-4}$ alkoxy $C_{1-4}$ haloalkoxy, and dimethylamino;

$R^{14a}$ is selected from the group $C_{1-4}$ alkyl, $C_{1-4}$ haloalkyl, $C_{1-4}$ alkoxy-$C_{1-4}$ alkyl, $C_{3-6}$ cycloalkyl, $C_{3-6}$ cycloalkyl-$C_{1-6}$ alkyl and benzyl, each benzyl being substituted on the aryl moiety with 0–1 substituents selected from the group $C_{1-4}$ alkyl, Br, Cl, F, I, $C_{1-4}$ haloalkyl, nitro, $C_{1-4}$ alkoxy, $C_{1-4}$ haloalkoxy, and dimethylamino;

$R^{14b}$ is selected from the group $C_{1-4}$ alkyl, $C_{1-4}$ haloalkyl, $C_{1-4}$ alkoxy-$C_{1-4}$ alkyl, $C_{3-6}$ cycloalkyl, and $C_{3-6}$ cycloalkyl-$C_{1-6}$ alkyl;

$R^{15}$ is independently selected at each occurrence from the group H, $C_{1-4}$ alkyl, $C_{3-7}$ cycloalkyl, $C_{3-6}$ cycloalkyl-$C_{1-6}$ alkyl, phenyl and benzyl, each phenyl or benzyl being substituted on the aryl moiety with 0–3 groups chosen from the group $C_{1-4}$ alkyl, Br, Cl, F, I, $C_{1-4}$ haloalkyl, nitro, $C_{1-4}$ alkoxy, $C_{1-4}$ haloalkoxy, and dimethylamino;

$R^{15a}$ is independently selected at each occurrence from the group H, $C_{1-4}$ alkyl, $C_{3-7}$ cycloalkyl, and $C_{3-6}$ cycloalkyl-$C_{1-6}$ alkyl;

$R^{17}$ is selected at each occurrence from the group H, $C_{1-6}$ alkyl, $C_{3-10}$ cycloalkyl, $C_{3-6}$ cycloalkyl-$C_{1-6}$ alkyl, $C_{1-2}$ alkoxy-$C_{1-2}$ alkyl, $C_{1-4}$ haloalkyl, $R^{14}S(O)_n$—$C_{1-4}$ alkyl, and $R^{17b}R^{19b}N$—$C_{2-4}$ alkyl;

$R^{18}$ and $R^{19}$ are independently selected at each occurrence from the group H, $C_{1-6}$ alkyl, $C_{3-10}$ cycloalkyl, $C_{3-6}$ cycloalkyl-$C_{1-6}$ alkyl, $C_{1-2}$ alkoxy-$C_{1-2}$ alkyl, and $C_{1-4}$ haloalkyl;

alternatively, in an $NR^{17}R^{19}$ moiety, $R^{17}$ and $R^{19}$ taken together form 1-pyrrolidinyl, 1-morpholinyl, 1-piperidinyl or 1-piperazinyl, wherein $N_4$ in 1-piperazinyl is substituted with 0–1 substituents selected from the group $R^{13}$, $CO_2R^{14}$, $COR^{14}$ and $SO_2R^{14}$;

alternatively, in an $NR^{17b}R^{19b}$ moiety, $R^{17b}$ and $R^{19b}$ taken together form 1-pyrrolidinyl, 1-morpholinyl, 1-piperidinyl or 1-piperazinyl, wherein $N_4$ in 1-piperazinyl is substituted with 0–1 substituents selected from the group $R^{13}$, $CO_2R^{14}$, $COR^{14}$ and $SO_2R^{14}$;

$R^{17a}$ and $R^{19a}$ are independently selected at each occurrence from the group H, $C_{1-6}$ alkyl, $C_{3-10}$ cycloalkyl, $C_{3-6}$ cycloalkyl-$C_{1-6}$ alkyl and $C_{1-4}$ haloalkyl;

aryl is independently selected at each occurrence from the group phenyl, naphthyl, indanyl and indenyl, each aryl being substituted with 0–5 substituents independently selected at each occurrence from the group $C_{1-6}$ alkyl, $C_{3-6}$ cycloalkyl, methylenedioxy, $C_{1-4}$ alkoxy-$C_{1-4}$ alkoxy, —$OR^{17}$, Br, Cl, F, I, $C_{1-4}$ haloalkyl, —CN, —$NO_2$, SH, —$S(O)_nR^{18}$, —$COR^{17}$, —$CO_2R^{17}$, —$OC(O)R^{18}$, —$NR^{15}COR^{17}$, —$N(COR^{17})_2$, —$NR^{15}CONR^{17}R^{19}$, —$NR^{15}CO_2R^{18}$, —$NR^{17}R^{19}$, and —$CONR^{17}R^{19}$ and up to 1 phenyl, each phenyl substituent being substituted with 0–4 substituents selected from the group $C_{1-3}$ alkyl, $C_{1-3}$ alkoxy, Br, Cl, F, I, —CN, dimethylamino, $CF_3$, $C_2F_5$, $OCF_3$, $SO_2Me$ and acetyl; and, heteroaryl is independently selected at each occurence from the group pyridyl, pyrimidinyl, triazinyl, furanyl, quinolinyl, isoquinolinyl, thienyl, imidazolyl, thiazolyl, indolyl, pyrrolyl, oxazolyl, benzofuranyl, benzothienyl, benzothiazolyl, benzoxazolyl, isoxazolyl, triazolyl, tetrazolyl, indazolyl, 2,3-dihydrobenzofuranyl, 2,3-dihydrobenzothienyl, 2,3-dihydrobenzothienyl-S-oxide, 2,3-dihydrobenzothienyl-S-dioxide, indolinyl, benzoxazolin-2-on-yl, benzodioxolanyl and benzodioxane, each heteroaryl being substituted 0–4 carbon atoms with a substituent independently selected at each occurrence from the group $C_{1-6}$ alkyl, $C_{3-6}$ cycloalkyl, Br, Cl, F, I, $C_{1-4}$ haloalkyl, —CN, nitro, —$OR^{17}$, SH, —$S(O)_mR^{18}$, —$COR^{17}$, —$CO_2R^{17}$, —$OC(O)R^{18}$, —$NR^{15}COR^{17}$, —$N(COR^{17})_2$, —$NR^{15}CONR^{17}R^{19}$, —$NR^{15}CO_2R^{18}$, —$NR^{17}R^{19}$, and —$CONR^{17}R^{19}$ and each heteroaryl being substituted on any nitrogen atom with 0–1 substituents selected from the group $R^{15}$, $CO_2R^{14a}$, $COR^{14a}$ and $SO_2R^{14a}$.

* * * * *